United States Patent
Connolly et al.

(10) Patent No.: US 10,413,545 B2
(45) Date of Patent: *Sep. 17, 2019

(54) IMIDAZOLIN-5-ONE DERIVATIVE USEFUL AS FASN INHIBITORS FOR THE TREATMENT OF CANCER

(71) Applicant: Janssen Pharmaceutica NV, Beerse (BE)

(72) Inventors: Peter J Connolly, New Providence, NJ (US); Tianbao Lu, Churchville, PA (US)

(73) Assignee: Janssen Pharmaceutica NV, Beerse (BE)

(*) Notice: Subject to any disclaimer, the term of this patent is extended or adjusted under 35 U.S.C. 154(b) by 0 days.

This patent is subject to a terminal disclaimer.

(21) Appl. No.: 15/631,167

(22) Filed: Jun. 23, 2017

(65) Prior Publication Data

US 2017/0290832 A1    Oct. 12, 2017

Related U.S. Application Data

(62) Division of application No. 14/573,012, filed on Dec. 17, 2014, now Pat. No. 9,718,813.

(60) Provisional application No. 61/916,844, filed on Dec. 17, 2013.

(51) Int. Cl.

| | | |
|---|---|---|
| *A61K 31/517* | (2006.01) | |
| *C07D 417/14* | (2006.01) | |
| *C07D 401/14* | (2006.01) | |
| *C07D 413/14* | (2006.01) | |
| *C07D 405/14* | (2006.01) | |
| *C07D 403/14* | (2006.01) | |
| *C07D 403/06* | (2006.01) | |
| *A61K 31/4178* | (2006.01) | |
| *A61K 31/423* | (2006.01) | |
| *A61K 31/428* | (2006.01) | |
| *A61K 31/4439* | (2006.01) | |
| *A61K 31/4709* | (2006.01) | |
| *A61K 31/4725* | (2006.01) | |
| *A61P 1/16* | (2006.01) | |
| *A61P 3/06* | (2006.01) | |
| *A61P 3/04* | (2006.01) | |
| *A61P 3/10* | (2006.01) | |

(52) U.S. Cl.
CPC ........ *A61K 31/517* (2013.01); *A61K 31/4178* (2013.01); *A61K 31/423* (2013.01); *A61K 31/428* (2013.01); *A61K 31/4439* (2013.01); *A61K 31/4709* (2013.01); *A61K 31/4725* (2013.01); *A61P 1/16* (2018.01); *A61P 3/04* (2018.01); *A61P 3/06* (2018.01); *A61P 3/10* (2018.01); *C07D 401/14* (2013.01); *C07D 403/06* (2013.01); *C07D 403/14* (2013.01); *C07D 405/14* (2013.01); *C07D 413/14* (2013.01); *C07D 417/14* (2013.01)

(58) Field of Classification Search
CPC .............. A61K 31/517; A61K 31/4178; A61K 31/423; A61K 31/428; C07D 417/14
See application file for complete search history.

(56) References Cited

FOREIGN PATENT DOCUMENTS

| JP | 2007-513973 A | 5/2007 |
|---|---|---|
| JP | 2013-520443 A | 6/2013 |

OTHER PUBLICATIONS

Menendez, Nature Reviews: Cancer, vol. 7, Oct. 2007, p. 763.*
Liu, Mol Cancer Ther 7(2), Feb. 2008, 263-270.*
Tian, Clin Oncol Cancer REs vol. 8, 1-9, 2011.*
Unger, Endocrinology, 144(12), 5159-5165, 2003.*
Cha, S.H., et al., "Long-term effect of a fatty acid synthase inhibitor on obese mice: food intake, hypothalamic neuropeptides, and UCP3", Biochem. and Biophys. Res. Commun., 2004, pp. 301-308, vol. 317.
Menendez, J.A., et al., "Fatty acid synthase and the lipogenic phenotype in cancer pathogenesis", Nature Rev Cancer, Oct. 2007, pp. 763-777, vol. 7.

(Continued)

Primary Examiner — D Margaret M Seaman

(57) ABSTRACT

The present invention is directed to imidazolin-5-one derivatives, pharmaceutical compositions containing them, and their use as FASN inhibitors, in for example, the treatment of cancer, obesity related disorders, and liver related disorders. Such compounds are represented by formula (I) as follows:

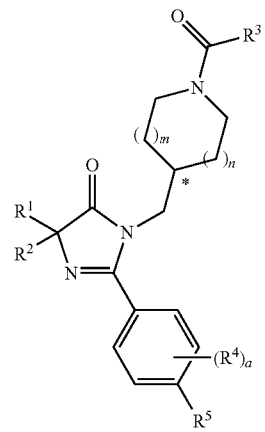

wherein $R^1$, $R^2$, $R^3$, $R^4$, $R^5$, m, n, and

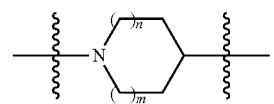

are defined herein.

4 Claims, No Drawings

(56) References Cited

OTHER PUBLICATIONS

Menendez, J.A. et al., "Fatty Acid Synthase: Association with Insulin resistance, Type 2 Diabetes, and Cancer", Clinical Chemistry, 2009, pp. 425-438 vol. 55(3).
Wu, M., et al., "Antidiabetic and antisteatotic effects of the selective fatty acid synthase (FAS) inhibitor platensimycin in mouse models of diabetes", PNAS, 2011, pp. 5378-5383, vol. 108(13).
Zaidi, N., et al., "Lipogenesis and lipolysis: The pathways exploited by the cancer cells to acquire fatty acids", Progress in Lipid Research, 2013, pp. 585-589, vol. 52.
International Search Report and Written Opinion for Application No. PCT/US2014/070271 dated Mar. 5, 2015.
Angeles, Thelma, S., et al., "Recent advances in targeting the fatty acid biosynthetic pathway using fatty acid synthase inhibitors", Expert Opinion on Drug Discovery, (2016) 11:12, 1187-1199.
Bandyopadhyay, Sucharita, et al., "FAS expression inversely correlates with PTEN level in prostate cancer and a PI 3-kinase inhibitor synergizes with FAS siRNA to induce apoptosis", Oncogene, (2005) 24: 5389-5395.
Bays, Nathan W., et al., "A Simplified Scintillation Proximity Assay for Fatty Acid Synthase Activity: Development and Comparison with Other FAS Activity Assays", Journal of Biomolecular Screening, (2009) 14: 636-642.
Jones, Suzanne F., et al., "Molecular Pathways: Fatty Acid Synthase", Clinical Cancer Research, (2015) 21(24): 5434-5438.
Kuhajda, Francis P, MD, "Fatty-Acid Synthase and Human Cancer: New Perspectives on Its Role in Tumor Biology", Elsevier Science Inc., Nutrition (2000) 16: 202-208.
Maier, et al., "Architecture of Mammalian Fatty Acid Synthase at 4.5 A Resolution", Science, (2006) 311: 1258-1262.
Menendez, Javier A., et al.,"Inhibition of fatty acid synthase (FAS) suppresses HER2/neu (erbB-2) oncogene overexpression in cancer cells", PNAS, (2004) 101, 29: 10715-10720.
Migita, Toshiro, et al., "Fatty Acid Synthase: A Metabolic Enzyme and Candidate Oncogene in Prostate Cancer", JNCI (2013) 11, 7: 519-532.
Mullen, Genevieve E., et al., "Progress in the development of fatty acid synthase inhibitors as anticancer targets", Bioorganic & Medicinal Chemistry Letters, Elsevier, ScienceDirect, (2015) 25: 4363-4369.
Portsmann, Thomas, et al., "PKB/Akt induces transcription of enzymes involved in cholstrerol and fatty acid biosynthesis via activation of SREBP", (2005) 24: 6465-6481.
Swinnen, Johannes V., et al., "Fatty acid synthase drives the synthesis of phospholipids partitioning into detergent-resistant membrane microdomains", Science Direct, Biochemical and Biophysical Research Communications (2003) 302: 898-903.
Swinnen, Johannes V., et al., "Stimulation of tumor-associated fatty acid synthase expression by growth factor activation of the sterol regulatory element-binding protein pathway", Oncogene (2000) 19: 5173-5181.
Van De Dande, Tine, et al., "Role of the Phosphatidylinositol 3'-Kinase/PTEN/Akt Kinase Pathway in the Overexpression of Fatty Acid Synthase in LNCaP Prostate Cancer Cells", (2002), 62: 642-646.

\* cited by examiner

IMIDAZOLIN-5-ONE DERIVATIVE USEFUL AS FASN INHIBITORS FOR THE TREATMENT OF CANCER

CROSS REFERENCE TO RELATED APPLICATIONS

The present application claims benefit of U.S. Non-Provisional application Ser. No. 14/573,012, filed on Dec. 17, 2014, currently pending, and U.S. Provisional Application No. 61/916,844, filed on Dec. 17, 2013, all of which are hereby incorporated by reference in their entirety.

FIELD OF THE INVENTION

The present invention is directed to imidazolin-5-one derivatives, pharmaceutical compositions containing them, and their use as FASN inhibitors, in for example, the treatment of cancer, obesity related disorders, and liver related disorders.

BACKGROUND OF THE INVENTION

Fatty acid synthase (FASN) is a key enzyme for the synthesis of long-chain fatty acids from acetyl-coenzyme A (CoA) and malonyl-CoA that uses reduced nicotinamide adenine dinucleotidephosphate as a cofactor. The final step in the de novo synthesis of fatty acids in mammalians is carried out by FASN, a 250 kDa protein containing 7 functional domains. Through an iterative enzymatic reaction, FASN produces palmitate starting from the substrates acetylCoA and malonylCo, using NADPH as a cofactor (See, MAIER, T., et al., "Architecture of mammalian fatty acid synthase at 4.5 Å resolution", *Science,* 2006, pp 1258-1262, Vol. 311).

FASN is minimally expressed in most normal human tissues except the liver and adipose tissue, where it is expressed at high levels. Except for these lipogenic tissues (such as liver, lactating breast, fetal lung, and adipose tissue), FASN has a low expression in normal cells which use fatty acids from the diet, while tumor cells largely depend on de novo fatty acid synthesis. FASN expression is highly up-regulated in various tumors, e.g. prostate, breast, colon, and lung cancer (See, SWINNEN, J. V., et al., "Stimulation of tumor-associated fatty acid synthase expression by growth factor activation of the sterol regulatory element-binding protein pathway". *Oncogene.* 2000, pp 5173-5181, Vol 19; KUHAJA, F. P., "Fatty-acid synthase and human cancer: new perspectives on its role in tumor biology", *Nutrition,* 2000, pp 202-208, Vol. 16).

FASN overexpression leads to growth and survival advantage to the tumors achieved through multiple mechanisms. Firstly, it provides lipids for membrane synthesis. Moreover, the more saturated lipid composition of the membranes increases resistance to chemotherapy. FASN also contributes to improved growth factor receptor expression in lipid rafts (See, SWINNEN, J. V., et al., "Fatty acid synthase drives the synthesis of phospholipids partitioning into detergent resistant membrane microdomains". *Biochem. Biophys. Res. Commun.,* 2000, pp 898-903, Vol, 302; MENENDEZ, J. A., et al., "Inhibition of fatty acid synthase (FAS) suppresses HER2/neu (erbB-2) oncogene overexpression in cancer cells", *Proc. Natl Acad, Sci. USA,* 2004, pp 10715-10720, Vol. 101), and improved cell signaling. Lastly, the NAPDPH consumption during palmitate synthesis in tumor cells keeps the redox balance in check.

In tumor cells, but not in normal cells, siRNA knock down or pharmacological inhibition of FASN results in apoptosis in vitro, and in a delayed tumor growth in vivo. The role of FASN as a potential oncogene has been further established in mouse models. Transgenic mouse models with FASN over expression in the prostate develop invasive prostate cancer in the presence of AR (See, MIGITA, eta., "Fatty Acid Synthase; A Metabolic Enzyme and Candidate Oncogene in Prostate Cancer", *J Natl. Cancer Inst.,* 2009, pp 519-532, Vol. 101). It has been proposed that FASN exerts its oncogenic effect by inhibiting the intrinsic pathway of apoptosis. Androgens and epidermal growth factor (EGF) up-regulate FASN expression and activity. In addition, FASN is also over expressed in androgen-independent prostate cancers most likely through activation of the PI3K/Akt pathway (See, BANDYOPADHYAY, S., et al., "FAS expression inversely correlates with PTEN level in prostate cancer and a PI-3 kinase inhibitor synergizes with FAS siRNA to induce apoptosis", *Oncogene,* 2005, pp 5389-5395, Vol. 24; VAN DE DANDE, T., et al., "Role of the phosphatidylinositol 3'-kinase/PTEN/Akt kinase pathway in the overexpression of fatty acid synthase in LNCaP prostate cancer cells", *Cancer Res.,* 2002, pp 642-646, Vol, 62; PORTSMANN, T., et al., "PKB/AKT induces transcription of enzymes involved in cholesterol and fatty acid biosynthesis via activation of SREBP", *Oncogene,* 2005, pp 6465-6481, Vol. 24). Thus, FASN is emerging as an important target for cancer therapy.

Since FASN expression is markedly increased in several human cancers compared with the corresponding normal tissue, and FASN over-expression in tumors has been associated with a poor prognosis, FASN inhibitors are viewed as potential therapeutics for the treatment of cancer. There remains a need for pharmaceutical agents for the treatment of a variety of cancers, including breast, prostate, head, neck, skin, lung, ovary, endometrium, thyroid, colon, rectum, esophagus, stomach, kidney, liver, bladder, pancreas, brain, blood, bone, and others.

FASN inhibitors have also shown promise in the treatment of other FASN-mediated diseases, disorders or conditions, such as obesity lack of appetite control and inflammatory conditions. Additionally, FASN has been implicated in diabetes and/or regulation of the general wellness of the liver, and therefore has potential in the treatment of obesity, Type II diabetes mellitus, Syndrome X and disorders of the liver; for the treatment of which there remains a need for pharmaceutical agents.

SUMMARY OF THE INVENTION

The present invention is directed to compounds of formula (I)

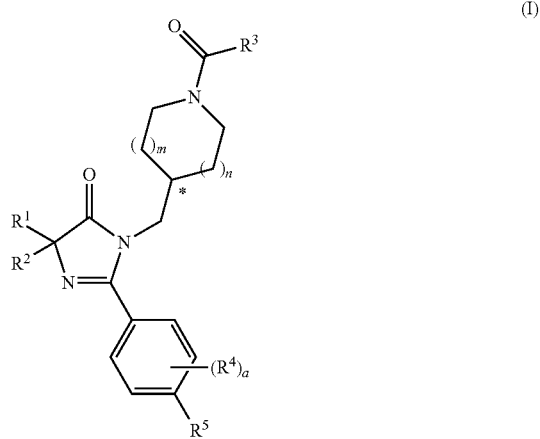

wherein

R¹ is $C_{1-4}$alkyl and fluorinated $C_{1-2}$alkyl;

R² is selected from the group consisting of $C_{1-4}$alkyl, fluorinated $C_{1-2}$alkyl, —($C_{1-4}$alkyl)-O—($C_{1-4}$alkyl), $C_{3-6}$cycloalkyl, phenyl and 5 to 6 membered heteroaryl; wherein the phenyl or 5 to 6 membered heteroaryl is optionally substituted with one to two substituents independently selected from the group consisting of halogen, $C_{1-4}$alkyl, fluorinated $C_{1-2}$alkyl, $C_{1-4}$alkoxy, fluorinated $C_1$-$C_2$alkoxy and cyano;

m is an integer from 0 to 1; and n is an integer from 0 to 1; provided that each of m and n are not 1;

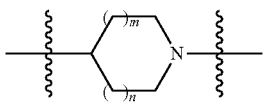

is selected from the group consisting of azetidin-3-yl, pyrrolidin-3-yl and piperidin-4-yl;

R³ is selected from the group consisting of $C_{1-4}$alkyl, fluorinated $C_{1-4}$alkyl, $C_{2-4}$alkenyl, $C_{3-6}$cycloalkyl, —($C_{1-4}$alkyl)-($C_{3-6}$cycloalkyl), 4 to 6 membered, saturated heterocyclyl, —($C_{1-4}$alkyl)-(4 to 6 membered, saturated heterocyclyl), 5 to 6 membered heteroaryl and —($C_{1-4}$alkyl)-(5 to 6 membered heteroaryl);

wherein the $C_{3-6}$cycloalkyl, 4 to 6 membered, saturated heterocyclyl or 5 to 6 membered heteroaryl, whether alone or as part of a substituent group, is optionally substituted with one to two substituents independently selected from the group consisting of halogen, hydroxy, cyano, $C_{1-4}$alkyl, fluorinated $C_{1-4}$alkyl, $C_{1-4}$alkoxy, fluorinated $C_{1-4}$alkoxy and $NR^AR^B$; wherein $R^A$ and $R^B$ are each independently selected from the group consisting of hydrogen and $C_{1-4}$alkyl;

a is an integer from 0 to 2;

each R⁴ is independently selected from the group consisting of hydroxy, halogen, $C_{1-4}$alkyl, fluorinated $C_{1-4}$alkyl, $C_{1-4}$alkoxy, fluorinated $C_{1-4}$alkoxy, cyano, and $NR^CR^D$; wherein $R^C$ and $R^D$ are each independently selected from the group consisting of hydrogen and $C_{1-4}$alkyl;

R⁵ is selected from the group consisting of aryl and heteroaryl; wherein the aryl or heteroaryl is optionally substituted with one to two substituents independently selected from the group consisting of hydroxy, halogen, cyano, nitro, $C_{1-4}$alkyl, fluorinated $C_{1-4}$alkyl, hydroxy substituted $C_{1-4}$alkyl, $C_{1-4}$alkoxy, fluorinated $C_{1-4}$alkoxy, $NR^ER^F$, —($C_{1-4}$alkyl)-$NR^ER^F$, —C(O)—($C_{1-4}$alkyl), —C(O)—$NR^ER^F$, —C(O)OH, —C(O)O—($C_{1-4}$alkyl), —$NR^E$—C(O)—($C_{1-4}$alkyl) and —$NR^E$—$SO_2$—($C_{1-4}$alkyl); wherein $R^E$ and $R^F$ are each independently selected from the group consisting of hydrogen and $C_{1-4}$alkyl;

alternatively, R⁵ is

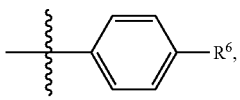

wherein —R⁶ is selected from the group consisting of phenyl and 5 to 6 membered heteroaryl; wherein the phenyl or 5 to 6 membered heteroaryl is optionally substituted with with one to two substituents independently selected from the group consisting of hydroxy, halogen, cyano, nitro, $C_{1-4}$alkyl, fluorinated $C_{1-4}$alkyl, hydroxy substituted $C_{1-4}$alkyl, $C_{1-4}$alkoxy, fluorinated $C_{1-4}$alkoxy, $NR^GR^H$, —C(O)—$NR^GR^H$, —C(O)OH, —C(O)O—($C_{1-4}$alkyl) and ($C_{1-4}$alkyl)-$NR^GR^H$; wherein $R^G$ and $R^H$ are each independently selected from the group consisting of hydrogen and $C_{1-4}$alkyl;

and stereoisomers, tautomers and pharmaceutically acceptable salts thereof.

The present invention is further directed to processes for the preparation of the compounds of formula (I), as described in more detail in the general synthesis schemes and examples, which follow herein. The present invention is further directed to a product prepared according to any of the processes as described in the general synthesis schemes and examples, which follow herein.

The present invention is further directed to intermediates in the synthesis of the compounds of formula (I), including, but not limited to, compounds of formula (XVIII), compounds of formula (XXI), compounds of formula (XXIII), compounds of formula (XXV), compounds of formula (XXVII), and compounds of formula (XXIX), as described in more detail herein.

Illustrative of the invention is a pharmaceutical composition comprising, consisting of and/or consisting essentially of a pharmaceutically acceptable carrier and the product prepared according to the process described herein. An illustration of the invention is a pharmaceutical composition made by mixing the product prepared according to the process described herein and a pharmaceutically acceptable carrier. Illustrating the invention is a process for making a pharmaceutical composition comprising, consisting of and/or consisting essentially of mixing the product prepared according to the process described herein and a pharmaceutically acceptable carrier.

Exemplifying the invention are methods of treating a disorder mediated by inhibition of fatty acid synthase (FASN) enzyme (selected from the group consisting of cancer, obesity and related disorders and liver related disorders, as herein defined) comprising, consisting of and/or consisting essentially of administering to a subject in need thereof a therapeutically effective amount of any of the compounds or pharmaceutical compositions described above.

In an embodiment, the present invention is directed to a compound of formula (I) for use as a medicament. In another embodiment, the present invention is directed to a compound of formula (I) for use in the treatment of a disorder mediated by inhibition of fatty acid synthase (FASN) enzyme (selected from the group consisting of cancer, obesity and related disorders and liver related disorders, as herein defined). In another embodiment, the present invention is directed to a composition comprising, consisting of and/or consisting essentially of a compound of formula (I) for the treatment of a disorder mediated by inhibition of fatty acid synthase (FASN) enzyme (selected from the group consisting of cancer, obesity and related disorders and liver related disorders, as herein defined).

Another example of the invention is the use of any of the compounds of formula (I) described herein in the preparation of a medicament for treating: (a) cancer, as herein defined, (b) obesity or related disorder, (c) liver related disorder, in a subject in need thereof.

In another example, the present invention is directed to a compound of formula (I) as described herein for use in a methods for treating a disorder selected from the group consisting of cancer, obesity and related disorders and liver related disorders, as herein defined, in a subject in need thereof.

DETAILED DESCRIPTION OF THE INVENTION

The present invention is directed to compounds of formula (I)

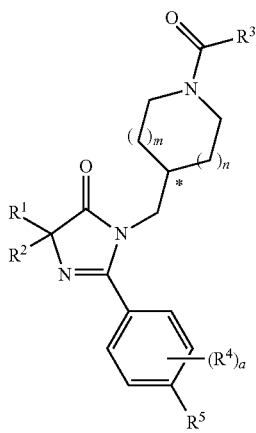

wherein $R^1$, $R^2$, $R^3$, $R^4$, $R^5$, a, m, n and

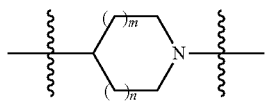

are as herein defined. The compounds of the present invention are FASN inhibitors useful in the treatment of, for example, cancer. More particularly, the compounds of formula (I) of the present invention are useful in the treatment of FASN-mediated disorders including, but not limited to, (a) cancer, as herein defined, (b) obesity and related disorders and (c) liver related disorders, as herein defined.

In an embodiment, the present invention is directed to methods for the treatment of cancer comprising, consisting of and/or consisting essentially of administering to a subjected in need thereof, a therapeutically effective amount of a compound of formula (I); wherein the cancer is selected from the group consisting of cancer of the breast, prostate, head, neck, skin, lung, ovary, endometrium, thyroid, colon, rectum, esophagus, stomach, kidney, liver, bladder, pancreas, brain, spinal cord, blood and bone. Preferably, the cancer is selected from the group consisting of breast, prostate, colon, lung, brain, spinal cord, ovary, endometrium, thyroid, kidney and stomach.

In another embodiment, the aforementioned cancer is selected from the group consisting of glioma, glioblastoma, leukemia, Bannayan-Zonana syndrome, Cowden disease, Lhermitte-Duclos disease, breast cancer, inflammatory breast cancer, Wilm's tumor, Ewing's sarcoma, Rhabdomyosarcoma, ependymoma, medulloblastoma, sarcoma, osteosarcoma, melanoma, giant cell tumor of bone and giant cell tumor of thyroid.

In another embodiment, the present invention is directed to methods for the treatment of obesity or a related disorder comprising, consisting of and/or consisting essentially of administering to a subjected in need thereof, a therapeutically effective amount of a compound of formula (I); wherein the obesity or related disorder is selected from the group consisting of obesity, overweight, weight gain, Type II diabetes mellitus, Syndrome X, and/appetite and/or satiety modulation. Preferably, the obesity or related disorders is selected from the group consisting of obesity, Type II diabetes mellitus, Syndrome X, and appetite and/or satiety modulation, more preferably obesity or Type II diabetes mellitus.

In another embodiment, the present invention is directed to methods for the treatment of an liver related disorder comprising, consisting of and/or consisting essentially of administering to a subjected in need thereof, a therapeutically effective amount of a compound of formula (I); wherein the liver related disorder is selected from the group consisting of dyslipidemia, elevated cholesterol levels, elevated LDL, decreased HDL, elevated triglicerides, fatty libver, non-alcoholic steatohepatitis (NASH), fatty liver or non-alcoholic fatty liver disease (NAFLD). Preferably, the liver related disorder is selected from the group consisting of dylipidemia and elevated cholestrol levels.

In an embodiment, the present invention is directed to a pharmaceutical composition comprising, consisting of and/or consisting essentially of a pharmaceutically acceptable carrier and a compound of formula (I). In another embodiment, the present invention is directed to a pharmaceutical composition made by mixing a compound of formula (I) and a pharmaceutically acceptable carrier. In another embodiment, the present invention is directed to a process for making a pharmaceutical composition comprising, consisting of and/or consisting essentially of mixing a compound of formula (I) and a pharmaceutically acceptable carrier.

In an embodiment, the present invention is directed to a method of treating a disorder mediated by inhibition of fatty acid synthase (FASN) enzyme, comprising, consisting of and/or consisting essentially of administering to a subject in need thereof a therapeutically effective amount of the compound of formula (I).

In another embodiment, the aforementioned disorder mediated by inhibition of fatty acid synthase (FASN) enzyme is cancer of the breast, prostate, head, neck, skin, lung, ovary, endometrium, thyroid, colon, rectum, esophagus, stomach, kidney, liver, bladder, pancreas, brain, spinal cord, blood or bone.

In another embodiment, the aforementioned he disorder mediated by inhibition of fatty acid synthase (FASN) enzyme is selected from the group consisting of obesity, overweight, weight gain, Type H diabetes mellitus, Syndrome X, and appetite or satiety modulation.

In another embodiment, the aforementioned disorder mediated by inhibition of fatty acid synthase (FASN) enzyme, is selected from the group consisting of dyslipidemia, elevated cholesterol levels, elevated LDL, decreased HDL, elevated triglicerides, fatty liver, non-alcoholic steatohepatitis (NASH), fatty liver and non-alcoholic fatty liver disease (NAFLD).

In an embodiment, the present invention is directed to a method of treating (a) cancer of the breast, prostate, head, neck, skin, lung, ovary, endometrium, thyroid, colon, rectum, esophagus, stomach, kidney, liver, bladder, pancreas, brain, spinal cord, blood or bone; (b) obesity or a related disorder selected from the group consisting of obesity, overweight, weight gain, Type II diabetes mellitus, Syndrome X, and appetite or satiety modulation; or (c) a liver related disorders selected from the group consisting of dyslipidemia, elevated cholesterol levels, elevated LDL, decreased HDL, elevated triglicerides, fatty liver, non-alcoholic steatohepatitis (NASH), fatty liver and non-alcoholic fatty liver disease (NAFLD); comprising, consisting of and/or consisting essentially of administering to a subject in need thereof, a therapeutically effective amount of the compound of formula (I).

In another embodiment, the present invention is directed to a method of treating (a) cancer of the breast, prostate, head, neck, skin, lung, ovary, endometrium, thyroid, colon, rectum, esophagus, stomach, kidney, liver, bladder, pancreas, brain, spinal cord, blood or bone; (b) obesity or a related disorder selected from the group consisting of obesity, overweight, weight gain, Type II diabetes mellitus, Syndrome X, and appetite or satiety modulation; or (c) a liver related disorders selected from the group consisting of dyslipidemia, elevated cholesterol levels, elevated LDL, decreased HDL, elevated triglicerides, fatty liver, non-alcoholic steatohepatitis (NASH), fatty liver and non-alcoholic fatty liver disease (NAFLD); comprising, consisting of and/or consisting essentially of administering to a subject in need thereof a therapeutically effective amount of a pharmaceutical composition comprising, consisting of and/or consisting essentially of a compound of formula (I).

In an embodiment, the present invention is directed to the use of a compound formula (I) for the preparation of a medicament for treating; (a) cancer of the breast, prostate, head, neck, skin, lung, ovary, endometrium, thyroid, colon, rectum, esophagus, stomach, kidney, liver, bladder, pancreas, brain, spinal cord, blood or bone; (b) obesity or a related disorder selected from the group consisting of obesity, overweight, weight gain, Type II diabetes mellitus, Syndrome X, and appetite or satiety modulation; or (c) a liver related disorders selected from the group consisting of dyslipidemia, elevated cholesterol levels, elevated LDL, decreased HDL, elevated triglicerides, fatty liver, non-alcoholic steatohepatitis (NASH), fatty liver and non-alcoholic fatty liver disease (NAFLD); in a subject in need thereof.

In another embodiment, the present invention is directed to the use of a compound of formula (I), for use in a method for treating a disorder selected from the group consisting of (a) cancer of the breast, prostate, head, neck, skin, lung, ovary, endometrium, thyroid, colon, rectum, esophagus, stomach, kidney, liver, bladder, pancreas, brain, spinal cord, blood or bone; (b) obesity or a related disorder selected from the group consisting of obesity, overweight, weight gain, Type II diabetes mellitus, Syndrome X, and appetite or satiety modulation; or (c) a liver related disorders selected from the group consisting of dyslipidemia, elevated cholesterol levels, elevated LDL, decreased HDL, elevated triglicerides, fatty liver, non-alcoholic steatohepatitis (NASH), fatty liver and non-alcoholic fatty liver disease (NAFLD); in a subject in need thereof.

In another embodiment, the present invention is directed to a compound of formula (I) for use as a medicament. In another embodiment, the present invention is directed to a compound of formula (I) (as in, for example, claim 1) for use in the treatment of a disorder mediated by inhibition of fatty acid synthase (FASN) enzyme. In another embodiment, the present invention is directed to a compound of formula (I), for use in the treatment of a disorder mediated by inhibition of fatty acid synthase (FASN) enzyme, selected from the group consisting of cancer of the breast, prostate, head, neck, skin, lung, ovary, endometrium, thyroid, colon, rectum, esophagus, stomach, kidney, liver, bladder, pancreas, brain, spinal cord, blood or bone. In another embodiment, the present invention is directed to a compound of formula (I), for use in the treatment of a disorder mediated by inhibition of fatty acid synthase (FASN) enzyme, selected from the group consisting of (a) obesity and related disorders and (b) liver related disorders.

In an embodiment, the present invention is directed to a composition comprising, consisting of and/or consisting essentially of compound of formula (I), for use in the treatment of a disorder mediated by inhibition of fatty acid synthase (FASN) enzyme.

In another embodiment, the present invention is directed to a composition comprising, consisting of and/or consisting essentially of compound of formula (I) for use in the treatment of a disorder mediated by inhibition of fatty acid synthase (FASN) enzyme selected from the group consisting of (a) cancer of the breast, prostate, head, neck, skin, lung, ovary, endometrium, thyroid, colon, rectum, esophagus, stomach, kidney, liver, bladder, pancreas, brain, spinal cord, blood or bone; (b) obesity or a related disorder selected from the group consisting of obesity, overweight, weight gain, Type II diabetes mellitus, Syndrome X, and appetite or satiety modulation; and (c) a liver related disorders selected from the group consisting of dyslipidemia, elevated cholesterol levels, elevated LDL, decreased HDL, elevated triglicerides, fatty liver, non-alcoholic steatohepatitis (NASH), fatty liver and non-alcoholic fatty liver disease (NAFLD).

In an embodiment, the present invention is directed to compounds of formula (I) wherein $R^1$ is selected from the group consisting of $C_{1-2}$alkyl and fluorinated $C_{1-2}$alkyl. In another embodiment, the present invention is directed to compounds of formula (I) wherein $R^1$ is $C_{1-2}$alkyl and trifluoromethyl. In another embodiment, the present invention is directed to compounds of formula (I) wherein $R^1$ is selected from the group consisting of methyl and trifluoromethyl. In another embodiment, the present invention is directed to compounds of formula (I) wherein $R^1$ is selected from the group consisting of $C_{1-2}$alkyl. In another embodiment, the present invention is directed to compounds of formula (I) wherein $R^1$ is methyl.

In an embodiment, the present invention is directed to compounds of formula (I) wherein $R^2$ is selected from the group consisting of $C_{1-2}$alkyl, trifluoromethyl, —($C_{1-2}$alkyl)-O—($C_{1-4}$alkyl), $C_{3-6}$cycloalkyl and phenyl; wherein the phenyl is optionally substituted with one to two substituents independently selected from the group consisting of halogen, $C_{1-4}$alkyl, fluorinated $C_{1-2}$alkyl, $C_{1-4}$alkoxy, fluorinated $C_{1-2}$alkoxy and cyano. In another embodiment, the present invention is directed to compounds of formula (I) wherein $R^2$ is selected from the group consisting of $C_{1-2}$alkyl, —($C_{1-2}$alkyl)-O—($C_{1-2}$alkyl), $C_{3-5}$cycloalkyl and phenyl.

In another embodiment, the present invention is directed to compounds of formula (I) wherein $R^2$ is selected from the group consisting of methyl, methoxy-methyl-, cyclopropyl and phenyl. In another embodiment, the present invention is directed to compounds of formula (I) wherein $R^2$ is selected from the group consisting of methyl, methoxy-methyl-, cyclopropyl and phenyl. In another embodiment, the present invention is directed to compounds of formula (I) wherein $R^2$ is selected from the group consisting of methyl and phenyl. In another embodiment, the present invention is directed to compounds of formula (I) wherein $R^2$ is methyl.

In an embodiment, the present invention is directed to compounds of formula (I) wherein m is 0. In another embodiment, the present invention is directed to compounds of formula (I) wherein m is 1. In an embodiment, the present invention is directed to compounds of formula (I) wherein n is 0. In another embodiment, the present invention is directed to compounds of formula (I) wherein n is 1.

In an embodiment, the present invention is directed to compounds of formula (I) wherein m is 0 and n is 0. In an embodiment, the present invention is directed to compounds of formula (I) wherein m is 1 and n is 1. In an embodiment, the present invention is directed to compounds of formula (I) wherein m is 1 and n is 0 or alternatively, m is 0 and n is 1.

In an embodiment, the present invention is directed to compounds of formula (I) wherein

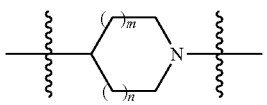

is selected from the group consisting of azetidin-3-yl, pyrrolidin-3-yl, pyrrolidin-3R-yl and pyrrolidin-3S-yl. In another embodiment, the present invention is directed to compounds of formula (I) wherein

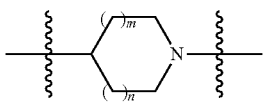

is selected from the group consisting of azetidin-3-yl, pyrrolidin-3-yl and pyrrolidin-3R-yl. In another embodiment, the present invention is directed to compounds of formula (I) wherein

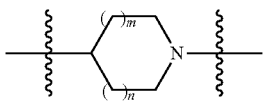

is selected from the group consisting of azetidin-3-yl and pyrrolidin-3R-yl.

In an embodiment, the present invention is directed to compounds of formula (I) wherein

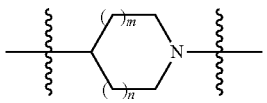

is other than azetidin-3-yl (i.e., wherein one or both of m and n are 1). In another embodiment, the present invention is directed to compounds of formula (I) wherein m is an integer from 0 to 1, n is an integer from 0 to 1, provided that when m is 1, then n is 0, and provided further that when n is 1, then m is 0.

In an embodiment, the present invention is directed to compounds of formula (I) wherein $R^3$ is selected from the group consisting of $C_{1-2}$alkyl, fluorinated $C_{1-2}$alkyl, $C_{3-5}$cycloalkyl, —($C_{1-2}$alkyl)-($C_{3-5}$cycloalkyl), 4 to 5 membered, oxygen-containing saturated heterocyclyl, —($C_{1-2}$alkyl)-(4 to 5 membered, oxygen-containing saturated heterocyclyl), 5 membered heteroaryl and —($C_{1-2}$alkyl)-(5 membered heteroaryl); wherein the $C_{3-5}$cycloalkyl, 4 to 6 membered, saturated heterocyclyl or 5 to 6 membered heteroaryl, whether alone or as part of a substituent group, is optionally substituted with one to two substituents independently selected from the group consisting of halogen, hydroxy, cyano, $C_{1-4}$alkyl, fluorinated $C_{1-2}$alkyl, $C_{1-4}$alkoxy, fluorinated $C_{1-2}$alkoxy and $NR^AR^B$; wherein $R^A$ and $R^B$ are each independently selected from the group consisting of hydrogen and $C_{1-2}$alkyl. In another embodiment, the present invention is directed to compounds of formula (I) wherein $R^3$ is selected from the group consisting of $C_{3-5}$cycloalkyl; wherein the $C_{3-5}$cycloalkyl is optionally substituted with a substituted selected from the group consisting of halogen, hydroxy and $C_{1-2}$alkyl.

In another embodiment, the present invention is directed to compounds of formula (I) wherein $R^3$ is selected from the group consisting of cyclopropyl, 1-fluoro-1-cyclopropyl, 1-methyl-1-cyclopropyl and 1-hydroxy-1-cyclopropyl. In another embodiment, the present invention is directed to compounds of formula (I) wherein $R^3$ is selected from the group consisting of cyclopropyl, 1-fluoro-1-cyclopropyl, 1-methyl-1-cyclopropyl and 1-hydroxy-1-cyclopropyl. In another embodiment, the present invention is directed to compounds of formula (I) wherein $R^3$ is selected from the group consisting of cyclopropyl, 1-methyl-1-cyclopropyl and 1-hydroxy-1-cyclopropyl.

In another embodiment, the present invention is directed to compounds of formula (I) wherein $R^3$ is selected from the group consisting of 4 to 5 membered, oxygen-containing saturated heterocyclyl.

In an embodiment, the present invention is directed to compounds of formula (I) wherein $R^3$ is selected from the group 4 to 6 membered, saturated heterocyclyl and 5 to 6 membered heteroaryl, wherein the 4 to 6 membered, saturated heterocyclyl or 5 to 6 membered heteroaryl contains at least one, preferably one to two, more preferably one nitrogen as part of the ring structure.

In an embodiment, the present invention is directed to compounds of formula (I) wherein a is an integer from 0 to 1. In another embodiment, the present invention is directed to compounds of formula (I) wherein a is an integer from 1 to 2. In another embodiment, the present invention is directed to compounds of formula (I) wherein a is 1.

In an embodiment, the present invention is directed to compounds of formula (I) wherein each $R^4$ is independently selected from the group consisting of hydroxy, halogen, $C_{1-2}$alkyl, trifluoromethyl, $C_{1-2}$alkoxy, trifluoromethoxy, cyano, and $NR^CR^D$; wherein $R^C$ and $R^D$ are each independently selected from the group consisting of hydrogen and $C_{1-2}$alkyl. In another embodiment, the present invention is directed to compounds of formula (I) wherein $R^4$ is selected from the group consisting of halogen and $C_{1-2}$alkyl. In another embodiment, the present invention is directed to compounds of formula (I) wherein $R^4$ is selected from the group consisting of 2-fluoro and 2-methyl. In another embodiment, the present invention is directed to compounds of formula (I) wherein $R^4$ is 2-fluoro.

In an embodiment, the present invention is directed to compounds of formula (I) wherein $R^5$ is selected from the group consisting of aryl and heteroaryl; wherein the aryl or heteroaryl is optionally substituted with one to two substituents independently selected from the group consisting of hydroxy, halogen, cyano, nitro, $C_{1-4}$alkyl, fluorinated $C_{1-4}$alkyl, hydroxy substituted $C_{1-4}$alkyl, $C_{1-4}$alkoxy, fluorinated $C_{1-4}$alkoxy, $NR^E R^F$, —($C_{1-4}$alkyl)-$NR^E R^F$, —C(O)—($C_{1-4}$alkyl), —C(O)—$NR^E R^F$, —C(O)OH, —C(O)O—($C_{1-4}$alkyl), —$NR^E$—C(O)—($C_{1-4}$alkyl) and $NR^E$—$SO_3$—($C_{1-4}$alkyl); wherein $R^E$ and $R^F$ are each independently selected from the group consisting of hydrogen and $C_{1-4}$alkyl.

In another embodiment, the present invention is directed to compounds of formula (I) wherein $R^5$ is

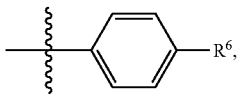

wherein —$R^6$ is selected from the group consisting of phenyl and 5 to 6 membered heteroaryl; wherein the phenyl or 5 to 6 membered heteroaryl is optionally substituted with one to two substituents independently selected from the group consisting of hydroxy, halogen, cyano, nitro, $C_{1-4}$alkyl, fluorinated $C_{1-4}$alkyl, hydroxy substituted $C_{1-4}$alkyl, $C_{1-4}$alkoxy, fluorinated $C_{1-4}$alkoxy, $NR^G R^H$, —C(O)—$NR^G R^H$, —C(O)OH, —C(O)O—($C_{1-4}$alkyl) and —($C_{1-4}$alkyl)-$NR^G R^H$; wherein $R^G$ and $R^H$ are each independently selected from the group consisting of hydrogen and $C_{1-4}$alkyl.

In an embodiment, the present invention is directed to compounds of formula (I) wherein $R^5$ is selected from the group consisting of aryl and heteroaryl; wherein the aryl or heteroaryl is optionally substituted with one to two substituents independently selected from the group consisting of hydroxy, halogen, cyano, nitro, $C_{1-2}$alkyl, trifluoromethyl, hydroxy substituted $C_{1-2}$alkyl, $C_{1-2}$alkoxy, trifluoromethoxy, $NR^E R^F$, —($C_{1-2}$alkyl)-$NR^E R^F$, —C(O)—($C_{1-4}$alkyl), —C(O)—$NR^E R^F$, —C(O)OH, —C(O)O—($C_{1-4}$alkyl), —$NR^E$—C(O)—($C_{1-4}$alkyl) and —$NR^E$—$SO_2$—($C_{1-4}$alkyl); wherein $R^E$ and $R^F$ are each independently selected from the group consisting of hydrogen and $C_{1-2}$alkyl. In another embodiment, the present invention is directed to compounds of formula (I) wherein $R^5$ is selected from the group consisting of naphthyl and bicyclic heteroaryl; wherein the naphthyl or bicyclic heteroaryl is optionally substituted with a substituent selected from the group consisting of halogen, $C_{1-2}$alkyl and cyano.

In another embodiment, the present invention is directed to compounds of formula (I) wherein $R^5$ is selected from the group consisting of 6-fluoro-naphth-2-yl, 6-cyano-naphth-2-yl, 8-fluoro-naphth-2-yl, indol-3-yl, indol-5-yl, indazol-3-yl, 1-methyl-indazol-5-yl, indazolin-3-yl, benzofur-5-yl, benzoxazol-2-yl, benzthiazol-2-yl, benzimidazol-2-yl, 1-methyl-benzimidazol-5-yl, quinolin-3-yl, quinolin-5-yl, quinolin-6-yl, quinolin-7-yl, isoquinolin-5-yl, isoquinolin-6-yl and quinazolin-7-yl. In another embodiment, the present invention is directed to compounds of formula (I) wherein $R^5$ is selected from the group consisting of 6-fluoro-naphth-2-yl, 8-fluoro-naphth-2-yl, indol-3-yl, indol-5-yl, indazol-3-yl, indazolin-3-yl, benzo-fur-5-yl, benzoxazol-2-yl, benzthiazol-2-yl, benzimidazol-2-yl, 1-methyl-benzimidazol-5-yl, quinolin-3-yl, quinolin-5-yl, quinolin-6-yl, quinolin-7-yl, isoquinolin-5-yl, isoquinolin-6-yl and quinazolin-7-yl. In another embodiment, the present invention is directed to compounds of formula (I) wherein $R^5$ is selected from the group consisting of 6-fluoro-naphth-2-yl, 8-fluoro-naphth-2-yl, 6-cyano-napthy-2-yl, indol-3-yl, indol-5-yl, indazol-3-yl, 1-methyl-indazol-5-yl, benzofur-5-yl, benzoxazol-2-yl, benzthiazol-2-yl, benzimidazol-2-yl, 1-methyl-benzimidazol-5-yl, quinolin-3-yl, quinolin-5-yl, quinolin-7-yl, isoquinolin-6-yl and quinazolin-7-yl. In another embodiment, the present invention is directed to compounds of formula (I) wherein $R^5$ is selected from the group consisting of 6-fluoro-naphth-2-yl, 8-fluoro-naphth-2-yl, 6-cyano-napthy-2-yl, indol-3-yl, indol-5-yl, 1-methyl-indazol-5-yl, benzofur-5-yl, benzoxazol-2-yl, benzthiazol-2-yl, 1-methyl-benzimidazol-5-yl, quinolin-5-yl, quinolin-7-yl, isoquinolin-6-yl and quinazolin-7-yl.

In another embodiment, the present invention is directed to compounds of formula (I) wherein $R^5$ is selected from the group consisting of 6-fluoro-naphth-2-yl, 8-fluoro-naphth-2-yl, 6-cyano-napthy-2-yl, indol-3-yl, indol-5-yl, 1-methyl-indazol-5-yl, benzofur-5-yl, 1-methyl-benzimidazol-5-yl, quinolin-7-yl and isoquinolin-6-yl. In another embodiment, the present invention is directed to compounds of formula (I) wherein $R^5$ is selected from the group consisting of 6-fluoro-naphth-2-yl, 8-fluoro-naphth-2-yl, 6-cyano-napthy-2-yl, indol-5-yl, 1-methyl-benzimidazol-5-yl, quinolin-7-yl and isoquinolin-6-yl. In another embodiment, the present invention is directed to compounds of formula (I) wherein $R^5$ is selected from the group consisting of 6-fluoro-naphth-2-yl, 8-fluoro-naphth-2-yl and 1-methyl-benzimidazol-5-yl.

In another embodiment, the present invention is directed to compounds of formula (I) wherein $R^5$ is selected from the group consisting of bicyclic heteroaryl; wherein the bicyclic heteroaryl is optionally substituted with one to two substituents independently selected from the group consisting of hydroxy, halogen, cyano, nitro, $C_{1-4}$alkyl, fluorinated $C_{1-4}$alkyl, hydroxy substituted $C_{1-4}$alkyl, $C_{1-4}$alkoxy, fluorinated $C_{1-4}$alkoxy, $NR^E R^F$, —($C_{1-4}$alkyl)-$NR^E R^F$, —C(O)—($C_{1-4}$alkyl), —C(O)—$NR^E R^F$, —C(O)OH, —C(O)O—($C_{1-4}$alkyl), —$NR^E$—C(O)—($C_{1-4}$alkyl) and —$NR^E$—$SO_2$—($C_{1-4}$alkyl); wherein $R^E$ and $R^F$ are each independently selected from the group consisting of hydrogen and $C_{1-4}$alkyl.

In an embodiment, the present invention is directed to compounds of formula (I) wherein alternatively, $R^5$ is

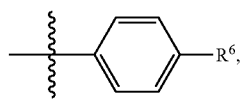

wherein $R^6$ is selected from the group consisting of phenyl and 5 to 6 membered heteroaryl; wherein the phenyl or 5 to 6 membered heteroaryl is optionally substituted with with one to two substituents independently selected from the group consisting of hydroxy, halogen, cyano, nitro, $C_{1-2}$alkyl, trifluoromethyl, hydroxy substituted $C_{1-2}$alkyl, $C_{1-4}$alkoxy, trifluoromethoxy, $NR^G R^H$, —C(O)—$NR^G R^H$, —C(O)OH, —C(O)O—($C_{1-4}$alkyl) and ($C_{1-2}$alkyl)-$NR^G R^H$; wherein $R^G$ and $R^H$ are each independently selected from the group consisting of hydrogen and $C_{1-2}$alkyl.

In another embodiment, the present invention is directed to compounds of formula (I) wherein $R^5$ is

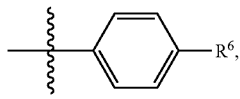

wherein $R^6$ is selected from the group consisting of 5 to 6 membered, nitrogen containing heteroaryl; wherein the 5 to 6 membered heteroaryl is optionally substituted with a substituted selected from the group consisting of $C_{1-2}$alkyl.

In another embodiment, the present invention is directed to compounds of formula (I) wherein $R^5$ is

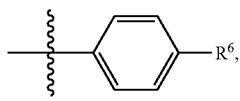

wherein $R^6$ is selected from the group consisting of pyrid-4-yl and 1-methyl-pyrazol-4-yl. In another embodiment, the present invention is directed to compounds of formula (I) wherein $R^5$ is

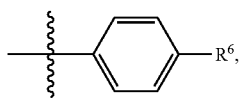

wherein $R^6$ is pyrid-4-yl.

In an embodiment, the present invention is directed to compounds of formula (I) selected from the group consisting of 1-((1-(cyclopropanecarbonyl)azetidin-3-yl)methyl)-2-(2-fluoro-4-(6-fluoronaphthalen-2-yl)phenyl)-4,4-dimethyl-1-H-imidazol-5(4H)-one; 2-(2-fluoro-4-(6-fluoronaphthalen-2-yl)phenyl)-1-((1-(1-hydroxycyclopropanecarbonyl)azetidin-3-yl)methyl)-4,4-dimethyl-1H-imidazol-5(4H)-one; (R)-1-((1-(cyclopropanecarbonyl)pyrrolidin-3-yl)methyl)-2-(2-fluoro-4-(6-fluoronaphthalen-2-yl)phenyl)-4,4-dimethyl-1H-imidazol-5(4H)-one; 1-((1-(cyclopropanecarbonyl)azetidin-3-yl)methyl)-2-(2-fluoro-4-(8-fluoronaphthalen-2-yl)phenyl)-4,4-dimethyl-1H-imidazol-5(4H)-one; 2-(2-fluoro-4-(6-fluoronaphthalen-2-yl)phenyl)-4,4-dimethyl-1-((1-(1-methylcyclopropanecarbonyl)azetidin-3-yl)methyl)-1H-imidazol-5(4H)-one; (R)-1-((1-(cyclopropanecarbonyl)pyrrolidin-3-yl)methyl)-4,4-dimethyl-2-(4'-(pyridin-4-yl)-[1,1'-biphenyl]-4-yl)-1H-imidazol-5(4H)-one; (R)-2-(2-fluoro-4-(6-fluoronaphthalen-2-yl)phenyl)-4,4-dimethyl-1-((1-(1-methylcyclopropanecarbonyl)pyrrolidin-3-yl)methyl)-1H-imidazol-5(4H)-one; (R)-1-((1-(cyclopropanecarbonyl)pyrrolidin-3-yl)methyl)-2-(4-(6-fluoronaphthalen-2-yl)phenyl)-4,4-dimethyl-1H-imidazol-5(4H)-one; (R)-4,4-dimethyl-2-(2-methyl-4-(1-methyl-1H-indazol-5-yl)phenyl)-1-((1-(1-methylcyclopropanecarbonyl)pyrrolidin-3-yl)methyl)-1H-imidazol-5(4H)-one, (R)-1-((1-(cyclopropanecarbonyl)pyrrolidin-3-yl)methyl)-2-(3-fluoro-4'-(1-methyl-1H-pyrazol-4-yl)-[1,1'-biphenyl]-4-yl)-4,4-dimethyl-1H-imidazol-5(4H)-one; and stereoisomers, tautomers and pharmaceutically acceptable salts thereof.

In another embodiment, the present invention is directed to compounds of formula (I) selected from the group consisting of 1-((1-(cyclopropanecarbonyl)azetidin-3-yl)methyl)-2-(2-fluoro-4-(6-fluoronaphthalen-2-yl)phenyl)-4,4-dimethyl-1H-imidazol-5(4H)-one; 2-(2-fluoro-4-(6-fluoronaphthalen-2-yl)phenyl)-1-((1-(1-hydroxycyclopropanecarbonyl)azetidin-3-yl)methyl)-4,4-dimethyl-1H-imidazol-5(4H)-one; (R)-1-((1-(cyclopropanecarbonyl)pyrrolidin-3-yl)methyl)-2-(2-fluoro-4-(6-fluoronaphthalen-2-yl)phenyl)-4,4-dimethyl-1H-imidazol-5(4H)-one: 1-((1-(cyclopropanecarbonyl)azetidin-3-yl)methyl)-2-(2-fluoro-4-(8-fluoronaphthalen-2-yl)phenyl)-4,4-dimethyl-1H-imidazol-5(4H)-one; 2-(2-fluoro-4-(6-fluoronaphthalen-2-yl)phenyl)-4,4-dimethyl-1-((1-(1-methylcyclopropanecarbonyl)azetidin-3-yl)methyl)-1H-imidazol-5(4H)-one; and stereoisomers, tautomers and pharmaceutically acceptable salts thereof.

Additional embodiments of the present invention, include those wherein the substituents selected for one or more of the variables defined herein (e.g. $R^1$, $R^2$, $R^3$, $R^4$, $R^5$, $L^1$, a, m, n,

etc.) are independently selected to be any individual substituent or any subset of substituents selected from the complete list as defined herein.

In additional embodiments, the present invention is directed to any single compound or subset of compounds, selected from the representative compounds listed in Table 1, below.

In an embodiment, the present invention is directed to compounds of formula (I) which, when tested according to the procedure as described in Biological Example 1, which follows herein, exhibit a $pIC_{50}$ of greater than about 5.0, preferably greater than about 6.0, more preferably greater than about 6.5, more preferably greater than about 7.0, more preferably greater than about 7.5.

Representative compounds of formula (I) of the present invention are as listed in Table 1, below. Unless otherwise noted, wherein a stereogenic center is present in the listed compound, the compound was prepared as a mixture of stereo-configurations. Where a stereogenic center is present, the S- and R-designations are intended to indicate that the exact stereo-configuration of the center was been determined.

TABLE 1

Representative Compounds of Formula (I)

| ID No. | R² | | R³ | (R⁴)ₐ | R⁵ |
|---|---|---|---|---|---|
| 1 | methyl | pyrrolidin-3R-yl | cyclopropyl | a = 0 | indol-5-yl |
| 2 | methyl | pyrrolidin-3R-yl | cyclopropyl | a = 0 | 1-methyl-indazol-5-yl |
| 3 | methyl | pyrrolidin-3R-yl | cyclopropyl | a = 0 | benzofur-5-yl |
| 4 | methyl | pyrrolidin-3R-yl | 1-fluoro-cycloprop-1-yl | a = 0 | benzofur-5-yl |
| 5 | methyl | pyrrolidin-3R-yl | cyclopropyl | a = 0 | benzofur-5-yl |
| 6 | phenyl | pyrrolidin-3R-yl | cyclopropyl | a = 0 | 1-methyl-indazol-5-yl |
| 7 | phenyl | pyrrolidin-3R-yl | cyclopropyl | a = 0 | indol-5-yl |
| 8 | methoxy-methyl- | pyrrolidin-3R-yl | cyclopropyl | a = 0 | benzofur-5-yl |
| 9 | cyclo-propyl | pyrrolidin-3R-yl | cyclopropyl | a = 0 | benzofur-5-yl |
| 10 | methoxy-methyl- | azetidin-3-yl | cyclopropyl | a = 0 | 1-methyl-indazol-5-yl |
| 11 | methyl | pyrrolidin-3R-yl | cyclopropyl | a = 0 | benzoxazol-2-yl |
| 12 | methyl | azetidin-3-yl | cyclopropyl | a = 0 | benzoxazol-2-yl |
| 13 | methyl | pyrrolidin-3R-yl | cyclopropyl | a = 0 | benzthiazol-2-yl |
| 14 | methyl | azetidin-3-yl | cyclopropyl | a = 0 | benzthiazol-2-yl |
| 15 | methyl | pyrrolidin-3R-yl | cyclopropyl | a = 0 | 4-(pyrid-4-yl)-phenyl |
| 16 | methyl | pyrrolidin-3R-yl | cyclopropyl | a = 0 | 4-(1-methyl-pyrazol-4-yl)-phenyl |
| 17 | methyl | azetidin-3-yl | cyclopropyl | a = 0 | 4-(1-methyl-pyrazol-4-yl)-phenyl |
| 18 | methyl | azetidin-3-yl | cyclopropyl | a = 0 | quinolin-5-yl |
| 19 | methyl | azetidin-3-yl | cyclopropyl | a = 0 | quinolin-3-yl |
| 20 | methyl | azetidin-3-yl | cyclopropyl | 2-fluoro | quinolin-3-yl |
| 21 | methyl | azetidin-3-yl | cyclopropyl | 2-fluoro | isoquinolin-5-yl |
| 22 | methyl | azetidin-3-yl | cyclopropyl | 2-fluoro | 4-(pyrid-4-yl)-phenyl |
| 23 | methyl | pyrrolidin-3R-yl | cyclopropyl | a = 0 | quinolin-7-yl |
| 24 | methyl | azetidin-3-yl | cyclopropyl | a = 0 | quinolin-7-yl |
| 25 | methyl | pyrrolidin-3R-yl | cyclopropyl | a = 0 | quinolin-3-yl |
| 26 | methyl | azetidin-3-yl | cyclopropyl | a = 0 | 4-(pyrid-4-yl)-phenyl |
| 27 | methyl | azetidin-3-yl | cyclopropyl | a = 0 | isoquinolin-6-yl |
| 28 | methyl | pyrrolidin-3R-yl | cyclopropyl | a = 0 | isoquinolin-6-yl |
| 29 | methyl | azetidin-3-yl | cyclopropyl | a = 0 | 6-fluoro-naphth-2-y |
| 30 | methyl | pyrrolidin-3R-yl | cyclopropyl | a = 0 | 6-fluoro-naphth-2-yl |
| 31 | methyl | pyrrolidin-3R-yl | cyclopropyl | a = 0 | quinolin-5-yl |
| 32 | methyl | pyrrolidin-3R-yl | cyclopropyl | 2-fluoro | 1-methyl-indazol-5-yl |
| 33 | methyl | azetidin-3-yl | cyclopropyl | 2-fluoro | 4-(1-methyl-pyrazol-4-yl)-phenyl |
| 34 | methyl | azetidin-3-yl | cyclopropyl | 2-fluoro | benzthiazol-2-yl |
| 35 | methyl | pyrrolidin-3R-yl | cyclopropyl | a = 0 | indazol-3-yl |

TABLE 1-continued

Representative Compounds of Formula (I)

| ID No. | R² | | R³ | (R⁴)ₐ | R⁵ |
|---|---|---|---|---|---|
| 36 | methyl | azetidin-3-yl | cyclopropyl | a = 0 | quinazolin-7-yl |
| 37 | methyl | pyrrolidin-3R-yl | cyclopropyl | 2-fluoro | quinolin-6-yl |
| 38 | methyl | azetidin-3-yl | cyclopropyl | 2-fluoro | quinolin-6-yl |
| 39 | methyl | azetidin-3-yl | cyclopropyl | 2-fluoro | quinolin-7-yl |
| 40 | methyl | azetidin-3-yl | cyclopropyl | a = 0 | 8-fluoro-naphth-2-yl |
| 41 | methyl | pyrrolidin-3R-yl | cyclopropyl | a = 0 | 8-fluoro-naphth-2-yl |
| 42 | methyl | pyrrolidin-3R-yl | cyclopropyl | a = 0 | quinazolin-7-yl |
| 43 | methyl | azetidin-3-yl | cyclopropyl | 2-fluoro | quinazolin-7-yl |
| 44 | methyl | pyrrolidin-3R-yl | cyclopropyl | 2-fluoro | quinazolin-7-yl |
| 45 | methyl | pyrrolidin-3R-yl | cyclopropyl | 2-fluoro | 4-(1-methyl-pyrazol-4-yl)-phenyl |
| 46 | methyl | pyrrolidin-3R-yl | cyclopropyl | 2-fluoro | 4-(pyrid-4-yl)-phenyl |
| 47 | methyl | pyrrolidin-3R-yl | cyclopropyl | 2-fluoro | quinolin-5-yl |
| 48 | methyl | pyrrolidin-3R-yl | cyclopropyl | 2-fluoro | quinolin-3-yl |
| 49 | methyl | pyrrolidin-3R-yl | cyclopropyl | 2-fluoro | quinolin-7-yl |
| 50 | methyl | pyrrolidin-3R-yl | cyclopropyl | 2-fluoro | benzthiazol-2-yl |
| 51 | methyl | pyrrolidin-3R-yl | cyclopropyl | 2-fluoro | benzoxazol-2-yl |
| 52 | methyl | azetidin-3-yl | cyclopropyl | 2-fluoro | benzoxazol-2-yl |
| 53 | methyl | pyrrolidin-3R-yl | cyclopropyl | 2-fluoro | 1-methyl-indazol-5-yl |
| 54 | methyl | azetidin-3-yl | cyclopropyl | 2-fluoro | 6-fluoro-naphth-2-yl |
| 55 | methyl | azetidin-3-yl | cyclopropyl | 2-fluoro | 8-fluoro-naphth-2-yl |
| 56 | methyl | azetidin-3-yl | cyclopropyl | 2-fluoro | isoquinolin-6-yl |
| 57 | methyl | pyrrolidin-3R-yl | cyclopropyl | 2-fluoro | indazol-3-yl |
| 58 | methyl | azetidin-3-yl | cyclopropyl | 2-fluoro | indazol-3-yl |
| 59 | methyl | azetidin-3-yl | cyclopropyl | a = 0 | indol-3-yl |
| 60 | methyl | azetidin-3-yl | cyclopropyl | 2-fluoro | benzimidazol-2-yl |
| 61 | methyl | pyrrolidin-3R-yl | cyclopropyl | 2-fluoro | benzimidazol-2-yl |
| 62 | methyl | azetidin-3-yl | cyclopropyl | 2-fluoro | indol-3-yl |
| 63 | methyl | pyrrolidin-3R-yl | cyclopropyl | 2-fluoro | indol-3-yl |
| 64 | methyl | pyrrolidin-3R-yl | cyclopropyl | a = 0 | quinolin-6-yl |
| 65 | methyl | pyrrolidin-3R-yl | cyclopropyl | a = 0 | indol-3-yl |
| 66 | methyl | pyrrolidin-3R-yl | cyclopropyl | 2-fluoro | 6-fluoro-naphth-2-yl |
| 67 | methyl | pyrrolidin-3R-yl | cyclopropyl | 2-fluoro | 8-fluoro-naphth-2-yl |
| 68 | methyl | pyrrolidin-3R-yl | cyclopropyl | 2-fluoro | isoquinolin-6-yl |
| 69 | methyl | azetidin-3-yl | 1-methyl-cycloprop-1-yl | 2-fluoro | 1-methyl-indazol-5-yl |
| 70 | methyl | azetidin-3-yl | 1-methyl-cycloprop-1-yl | 2-fluoro | 4-(1-methyl-pyrazol-4-yl)-phenyl |
| 71 | methyl | pyrrolidin-3R-yl | cyclopropyl | a = 0 | benzimidazol-2-yl |
| 72 | methyl | azetidin-3-yl | 1-methyl-cycloprop-1-yl | 2-fluoro | 6-fluoro-naphth-2-yl |
| 73 | methyl | pyrrolidin-3R-yl | 1-methyl-cycloprop-1-yl | 2-fluoro | 1-methyl-indazol-5-yl |

TABLE 1-continued

Representative Compounds of Formula (I)

| ID No. | R² | | R³ | (R⁴)ₐ | R⁵ |
|---|---|---|---|---|---|
| 74 | methyl | pyrrolidin-3R-yl | 1-methyl-cycloprop-1-yl | 2-fluoro | 4-(1-methyl-pyrazol-4-yl)-phenyl |
| 75 | methyl | pyrrolidin-3R-yl | 1-methyl-cycloprop-1-yl | 2-fluoro | 6-fluoro-naphth-2-yl |
| 76 | methyl | pyrrolidin-3R-yl | 1-hydroxy-cycloprop-1-yl | 2-fluoro | 1-methyl-indazol-5-yl |
| 77 | methyl | azetidin-3-yl | 1-methyl-cycloprop-1-yl | 2-methyl | 1-methyl-indazol-5-yl |
| 78 | methyl | azetidin-3-yl | 1-hydroxy-cycloprop-1-yl | 2-fluoro | 1-methyl-indazol-5-yl |
| 79 | methyl | azetidin-3-yl | 1-hydroxy-cycloprop-1-yl | 2-fluoro | 6-fluoro-naphth-2-yl |
| 80 | methyl | pyrrolidin-3R-yl | 1-methyl-cycloprop-1-yl | 2-fluoro | 1-methyl-indazol-5-yl |
| 81 | methyl | azetidin-3-yl | 1-hydroxy-cycloprop-1-yl | 2-fluoro | 4-(1-methyl-pyrazol-4-yl)-phenyl |
| 82 | methyl | azetidin-3-yl | 1-methyl-cycloprop-1-yl | 2-methyl | 6-fluoro-naphth-2-yl |
| 83 | methyl | azetidin-3-yl | 1-methyl-cycloprop-1-yl | 2-methyl | 1-methyl-benzimidazol-5-yl |
| 84 | methyl | pyrrolidin-3R-yl | 1-methyl-cycloprop-1-yl | 2-methyl | 4-(1-methyl-pyrazol-4-yl)-phenyl |
| 85 | methyl | pyrrolidin-3R-yl | 1-methyl-cycloprop-1-yl | 2-methyl | 1-methyl-benzimidazol-5-yl |
| 86 | methyl | pyrrolidin-3R-yl | 1-methyl-cycloprop-1-yl | 2-methyl | 6-fluoro-naphth-2-yl |
| 87 | methyl | azetidin-3-yl | 1-methyl-cycloprop-1-yl | 2-methyl | 4-(1-methyl-pyrazol-4-yl)-phenyl |
| 88 | methyl | pyrrolidin-3R-yl | 1-hydroxy-cycloprop-1-yl | 2-fluoro | 6-fluoro-naphth-2-yl |
| 89 | methyl | pyrrolidin-3R-yl | 1-hydroxy-cycloprop-1-yl | 2-fluoro | 1-methyl-benzimidazol-5-yl |
| 90 | methyl | pyrrolidin-3R-yl | 1-methyl-cycloprop-1-yl | 2-fluoro | 1-methyl-benzimidazol-5-yl |
| 91 | methyl | azetidin-3-yl | 1-hydroxy-cycloprop-1-yl | 2-methyl | 1-methyl-benzimidazol-5-yl |
| 92 | methyl | pyrroliclin-3R-yl | 1-hydroxy-cycloprop-1-yl | 2-fluoro | 1-methyl-benzimidazol-5-yl |
| 93 | methyl | azetidin-3-yl | 1-methyl-cycloprop-1-yl | 2-fluoro | 1-methyl-benzimidazol-5-yl |
| 94 | methyl | azetidin-3-yl | 1-hydroxy-cycloprop-1-yl | 2-fluoro | 1-methyl-benzimidazol-5-yl |
| 95 | methyl | pyrrolidin-3R-yl | 1-hydroxy-cycloprop-1-yl | 2-fluoro | 4-(1-methyl-pyrazol-4-yl)-phenyl |
| 96 | methyl | azetidin-3-yl | cyclopropyl | 2-methyl | 6-cyano-naphth-2-yl |
| 97 | methyl | azetidin-3-yl | cyclopropyl | 2-fluoro | 6-cyano-naphth-2-yl |

TABLE 1-continued

Representative Compounds of Formula (I)

| ID No. | R² | 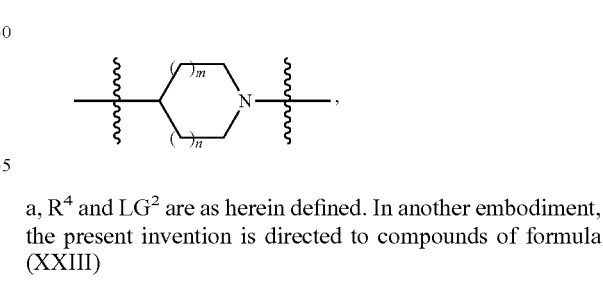 | R³ | (R⁴)ₐ | R⁵ |
|---|---|---|---|---|---|
| 98 | methyl | azetidin-3-yl | cyclopropyl | a = 0 | quinolin-6-yl |
| 99 | methyl | azetidin-3-yl | cyclopropyl | a = 0 | indazolin-3-yl |

The present invention is further directed to intermediates in the synthesis of the compounds of formula (I), as described in more detail herein. In an embodiment, the present invention is directed to compound of formula (XVIII)

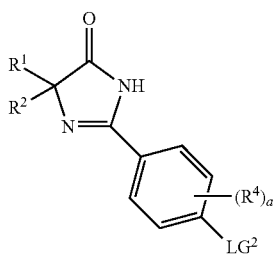

(XVIII)

wherein $R^1$, $R^2$, a, $R^4$ and $LG^2$ are as herein defined. In another embodiment, the present invention is directed to compounds of formula (XXI)

(XXI)

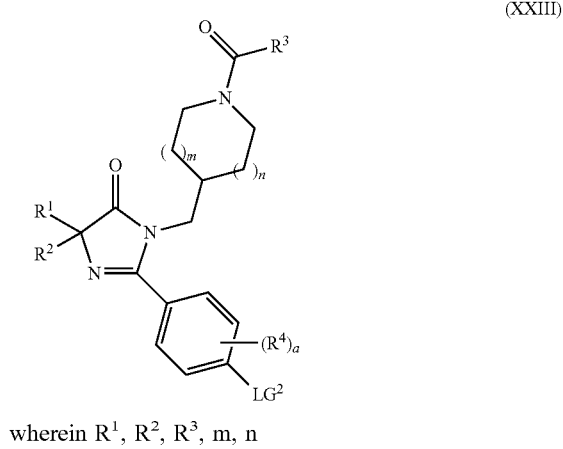

wherein $R^1$, $R^2$, m, n $$\text{\char"007B}\!\!\!\begin{array}{c}\text{\scriptsize(\ )}_m\\ \diagdown\\ \diagup\\ \text{\scriptsize(\ )}_n\end{array}\!\!\text{N}\!\!\text{\char"007D}\!\!\text{,}$$

a, $R^4$ and $LG^2$ are as herein defined. In another embodiment, the present invention is directed to compounds of formula (XXIII)

(XXIII)

wherein $R^1$, $R^2$, $R^3$, m, n $$\text{\char"007B}\!\!\!\begin{array}{c}\text{\scriptsize(\ )}_m\\ \diagdown\\ \diagup\\ \text{\scriptsize(\ )}_n\end{array}\!\!\text{N}\!\!\text{\char"007D}\!\!\text{,}$$

a, $R^4$ and $LG^2$ are as herein defined. In another embodiment, the present invention is directed to compounds of formula (XXV)

(XXV)

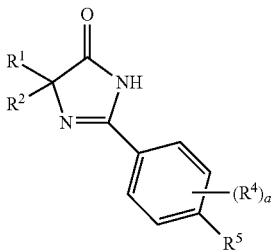

wherein $R^1$, $R^2$, a, $R^4$ and $R^5$ are as herein defined. In another embodiment, the present invention is directed to compounds of formula (XXVII)

(XXVII)

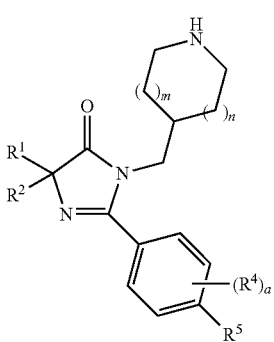

wherein $R^1$, $R^2$, m, n,

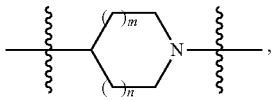

a, $R^4$ and $R^5$ are as herein defined.

Definitions

As used herein, unless otherwise noted, the term "halogen" means chloro, bromo, fluoro and iodo. Preferably, the halogen is bromo, chloro or fluoro.

As used herein, unless otherwise noted, the term "oxo" when used to define a substituent group means an oxygen atom which is bound to a chain or ring carbon atom through a double bond (i.e. =O).

As used herein, the term "$C_{X-Y}$alkyl" whether used alone or as part of a substituent group, means any straight and branched carbon chain composition of between X and Y carbon atoms. For example, "$C_{1-6}$alkyl" means any straight or branched carbon chain composition of between 1 and 6 carbon atoms, including, but not limited to methyl, ethyl, propyl, isopropyl, butyl, isobutyl, sec-butyl, t-butyl, n-pentyl, n-hexyl, and the like.

One skilled in the art will recognize that the term "—($C_{X-Y}$alkyl)-" shall denote any $C_{X-Y}$alkyl carbon chain as herein defined, wherein said $C_{X-Y}$alkyl chain is divalent and is bound through two points of attachment, preferably through two terminal carbon atoms. For example, "—($C_{1-4}$alkyl)-" includes, but is not limited to —CH$_2$—, —CH$_2$CH$_2$—, —CH(CH$_3$)—, —CH$_2$CH$_2$CH$_2$—, —CH$_2$CH(CH$_3$)—, —CH$_2$CH$_2$CH$_2$CH$_2$—, CH$_2$CH(CH$_3$)CH$_2$—, and the like.

As used herein, unless otherwise noted, the term "fluorinated $C_{X-Y}$alkyl" means any $C_{X-Y}$alkyl group as defined above substituted with at least one fluoro atom. For example, the term "fluorinated $C_{1-4}$alkyl" includes, but is not limited to —CF$_3$, —CH$_2$—CF$_3$, —CF$_2$—CF$_2$—CF$_2$—CF$_3$, and the like.

As used herein, unless otherwise noted, the term "hydroxy substituted $C_{X-Y}$alkyl" means $C_{X-Y}$alkyl group as defined above substituted with at least one hydroxy group. Preferably, the $C_{X-Y}$alkyl group is substituted with one hydroxy group. Preferably, the $C_{X-Y}$alkyl group is substituted with a hydroxy group at the terminal carbon. For example, the term "hydroxy substituted $C_{1-4}$alkyl" includes, but is not limited to, —CH$_2$(OH), —CH$_2$—CH$_2$(OH), —CH$_2$—CH(OH)—CH$_2$, and the like.

As used herein, the term "$C_{X-Y}$alkenyl" whether used alone or as part of a substituent group, means any straight and branched carbon chain composition of between X and Y carbon atoms having at least one unsaturated double bond. For example, "$C_{2-4}$alkyl" means any straight or branched carbon chain composition of between 2 and 4 carbon atoms having at least one double bond. Suitably examples include, but are not limited to, —CH=CH$_2$, —CH$_2$—CH=CH$_2$, —CH=CH$_2$—CH$_3$, —CH$_2$—CH$_2$—CH=CH$_2$, —CH$_2$—CH=CH—CH$_3$, and the like.

As used herein, unless otherwise noted, "$C_{X-Y}$alkoxy" wherein X and Y are integers, shall denote an oxygen ether radical of the above described straight or branched chain $C_{X-Y}$alkyl groups. For example, the term "$C_{1-4}$alkoxy" includes, but is not limited to methoxy, ethoxy, n-propoxy, sec-butoxy, t-butoxy, n-hexyloxy and the like.

As used herein, unless otherwise noted, the term "fluorinated $C_{X-Y}$alkoxy" wherein X and Y are integers means any oxygen ether radical as defined above substituted with at least one fluoro atom. For example, the term "fluorinated $C_{1-4}$alkoxy" includes, but is not limited to —OCF$_3$, —OCH$_2$—CF$_3$, —OCF$_2$—CF$_2$—CF$_2$—CF$_3$, and the like.

As used herein, unless otherwise noted, the term "$C_{X-Y}$cycloalkyl" wherein X and Y are integers means any stable saturated ring system having between X and Y carbon ring atoms. For example, the term "$C_{1-8}$cycloalkyl" means any stable 3 to 8 membered saturated ring structure, including cyclopropyl, cyclobutyl, cyclopentyl, cyclohexyl, cycloheptyl and cyclooctyl.

As used herein, unless otherwise noted, "aryl" means any carbocylic aromatic ring structure as phenyl, naphthyl, and the like. Preferably, the aryl is phenyl or naphthyl, more preferably phenyl.

As used herein, unless otherwise noted, "heteroaryl" shall denote any five or six membered monocyclic aromatic ring structure containing at least one heteroatom selected from the group consisting of O, N and S, optionally containing one to three additional heteroatoms independently selected from the group consisting of O, N and S; or any nine or ten membered bicyclic aromatic ring structure containing at least one heteroatom selected from the group consisting of O, N and S, optionally containing one to four additional heteroatoms independently selected from the group consisting of O, N and S; and wherein the heteroaryl contains one of more S heteroatom(s), said S heteroatom(s) are each independently optionally substituted with one to two oxo groups. The heteroaryl group may be attached at any heteroatom or carbon atom of the ring such that the result is a stable structure. Examples of suitable heteroaryl groups include, but are not limited to, pyrrolyl, furyl, thienyl, oxazolyl, imidazolyl, purazolyl, isoxazolyl, isothiazolyl, triazolyl, thiadiazolyl, tetrazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like.

As used herein, unless otherwise noted, the term "5 to 6 membered heteroaryl" shall denote any five or six membered monocyclic aromatic ring structure containing at least one heteroatom selected from the group consisting of O, N and S, optionally containing one to three additional heteroatoms independently selected from the group consisting of O, N and S; wherein the 5 to 6 membered heteroaryl contains one of more S heteratom(s), said S heteroatom(s) are each independently optionally substituted with one to two oxo groups. The 5 to 6 membered heteroaryl may be attached at any heteroatom or carbon atom of the ring such that the result is a stable structure. Suitable examples include, but are not limited to, pyrrolyl, furyl, thienyl, oxazolyl, thiazolyl, imidazolyl, purazolyl, isoxazolyl, isothiazolyl, triazolyl, thiadiazolyl, tetrazolyl, pyridyl, pyridazinyl, pyrimidinyl, pyrazinyl, pyranyl, furazanyl, and the like. Preferred 5 to 6 membered heteroaryl include one or more selected from the group consisting of pyrrolyl, furanyl, thienyl, oxazolyl, thiazolyl, imidazolyl, pyrazolyl, triazolyl, tetrazolyl, pyridyl, pyrimidinyl, pyrazonyl, and pyranyl.

As used herein, unless otherwise noted, the term "5 to 6 membered, nitrogen containing heteroaryl" shall denote any five or six membered monocyclic aromatic ring structure containing at least one N heteroatom, optionally containing one to three additional heteroatoms independently selected from the group consisting of O, N and S; wherein the 5 to 6 membered, nitrogen containing heteroaryl contains one of more S heteratom(s), said S heteroatom(s) are each independently optionally substituted with one to two oxo groups. The 5 to 6 membered, nitrogen containing heteroaryl may be attached at any heteroatom or carbon atom of the ring such that the result is a stable structure. Suitably examples include, but are not limited to pyrrolyl, oxazolyl, thiazolyl, imidazolyl, pyrazolyl, triazolyl, pyridyl, pyridazinyl, pyrimidinyl, pyrazinyl, triazinyl, and the like. Preferred 5 to 6 membered, nitrogen containing heteroaryl include one or more selected from the group consisting of pyrrolyl, imidazolyl, pyrazolyl, pyridyl, pyridazinyl, pyrimidinyl and pyrazinyl.

As used herein, unless otherwise noted the term "bicyclic heteroaryl" shall denote any nine or ten membered bicyclic aromatic ring structure containing at least one heteroatom selected from the group consisting of O, N and S, optionally containing one to four additional heteroatoms independently selected from the group consisting of O, N and S; and wherein the heteroaryl contains one of more S heteratom(s), said S heteroatom(s) are each independently optionally substituted with one to two oxo groups. The bicyclic heteroaryl group may be attached at any heteroatom or carbon atom of the ring such that the result is a stable structure. Examples of suitable bicyclic heteroaryl groups include, but are not limited to, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like.

As used herein, the term "heterocyclyl" shall denote any four to eight membered monocyclic, saturated or partially unsaturated ring structure containing at least one heteroatom selected from the group consisting of O, N and S, optionally containing one to three additional heteroatoms independently selected from the group consisting of O, N and S; or a nine to ten membered saturated, partially unsaturated or partially aromatic (e.g. benzo-fused) bicyclic ring system containing at least one heteroatom selected from the group consisting of O, N and S, optionally containing one to four additional heteroatoms independently selected from the group consisting of O, N and S; and wherein the heterocyclcyl contains one of more S heteratom(s), said S heteroatom(s) are each independently optionally substituted with one to two oxo groups. The heterocyclyl group may be attached at any heteroatom or carbon atom of the ring such that the result is a stable structure. Suitably examples include, but are not limited to, pyrrolinyl, pyrrolidinyl, dioxalanyl, imidazolinyl, imidazolidinyl, pyrazolinyl, pyrazolidinyl, piperidinyl, 1,4-dioxanyl, morpholinyl, 1,4-dithianyl, thiomorpholinyl, piperazinyl, trithianyl, azepanyl, 1,4-diazepanyl, 1,4-oxazepnayl, indolinyl, isoindolinyl, chromenyl, 3,4-methylenedioxyphenyl, 2,3-dihydrobenzofuranyl, tetrahydrofuranyl, and the like. Preferred heterocycloalkyl groups include one or more selected from the group consisting of pyrrolidinyl, dioxaklanyl, imidazolidinyl, pyrazolinyl, pyrazolidinyl, piperidinyl, morpholinyl, piperazinyl, azepanyl, 1,4-diazepanyl, 1,4-oxazepanyl, indolinyl, 2,3-dihydro-furanyl and tetrahydro-furanyl.

As used herein, unless otherwise noted, the term "4 to 6 membered saturated heterocyclyl" shall denote any 4 to 6 membered monocyclic, saturated ring structure containing at least one heteroatom selected from the group consisting of O, S and N, optionally containing one to three additional heteroatoms independently selected from the group consisting of O, S and N; and wherein the 4 to 6 membered saturated heterocyclyl contains one or more S heteroatom(s), said S heteroatom(s) are each independently, optionally substituted with one to two oxo groups. The 4 to 6 membered saturated heterocyclyl group may be attached at any heteroatom or carbon atom of the ring such that the result is a stable structure. Suitable examples include, but are not limited to Suitably examples include, but are not limited to, pyrrolidinyl, dioxolanyl, imidazolidinyl, pyrazolidinyl, piperidinyl, 1,4-dioxanyl, morpholinyl, 1,4-dithianyl, thiomorpholinyl, piperazinyl, azepanyl, 1,4-diazepanyl, 1.4-oxazapanyl, and the like. Preferably, the 4 to 6 membered saturated heterocyclyl include one or more selected from the group consisting of pyrrolidinyl, dioxolanyl, piperidinyl, 1,4-dioxanyl, morpholinyl, piperazinyl, azepanyl, 1,4-diazepanyl and 1,4-oxazapanyl.

When a particular group is "substituted" (e.g., $C_{X-Y}$alkyl, $C_{X-Y}$cycloalkyl, aryl, heteroaryl, heterocyclyl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Furthermore, it is intended that within the scope of the present invention, any element, in particular when mentioned in relation to a compound of formula (I), shall comprise all isotopes and isotopic mixtures of said element, either naturally occurring or synthetically produced, either with natural abundance or in an isotopically enriched form. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive. Radiolabelled compounds of formula (I) may comprise a radioactive isotope selected from the group of 3H, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^3H$, $^{11}C$ and $^{18}F$.

Unless otherwise denoted through use of a "-" symbol, under standard nomenclature used throughout this disclosure, the terminal portion of the designated side chain is described first, followed by the adjacent functionality toward the point of attachment. Thus, for example, a "phenyl$C_1$-$C_6$alkylaminocarbonyl$C_1$-$C_6$alkyl" substituent refers to a group of the formula

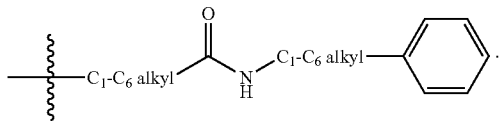

Abbreviations used in the specification, particularly the Schemes and Examples, are as follows:
AcOH or HOAc=Acetic acid
ATP=Adenosine Triphosphate
Boc or BOC=tert-Butoxycarbonyl
BSA=Bovine Serum Albumin
Cbz=Carboxybenzyl
CDI=Carbonyldiimidazole
CoA=Acetyl Coenzyme A
DCE=Dichloroethane
DCM=Dichloromethane
DIPEA or DIEA=Diisopropylethylamine
DMAP=4-N,N-Dimethylaminopyridine
DME=Dimethyl Ether
DMF=N,N-Dimethylformamide
DMSO=Dimethylsulfoxide
DTT=Dithiothreitol
EDAC or EDCI=1-Ethyl-3-(3-dimethylaminopropyl) carbodiimide
EDTA=Ethylenediaminetetraacetic acid
EGF=Epidermal Growth Factor
$Et_3N$ or TEA=Triethylamine
EtOAc=Ethyl acetate
FASN=Fatty Acid Synthase
FBS=Fetal Bovine Serum
FCS=Fetal Calf Serum
HATU=o-(7-Azabenzotriazol-1-yl)-N,N,N',N'-tetramethyluronium hexafluorophosphate
HBTU=2-(1H-Benzotriazole-1-yl)-1,1,3,3-Tetramethyluronium hexafluorophosphate
HEPES N-2-Hydroxyethylpiperazine-N'-2-Ethanesulfonic Acid (Buffer)
hFASN=Human fatty Acid Synthase
HDL=High Density Lipoprotein
HPLC=High Performance Liquid Chromatography
LDL=Low Density Lipoprotein
LHMDS=Lithium Bis(trimethylsilyl)amide
LRS=Lipid-Reduced Serum
MaCoA=Malonyl Coenzyme A
MEM=Eagle's minimum essential medium
Mesylate=Methanesulfonate
Mesyl=Methanesulfonyl
MS-Cl=Mesyl Chloride
MTT=Methyl Thiazolyl Tetrazolium
NADPH=Nicotinamide adenine dinucleotide phosphate
NAFLD=Non-alcoholic Fatty Liver Disease
NASH=Non-alcoholic Steatohepatitis
NMP=1-Methyl-2-pyrrolidinone
NMR=Nuclear Magnetic Resonance
PBS=Phosphate-buffered Saline
Pd/C=Palladium on Carbon Catalyst
$Pd_2(OAc)_2$=Palladium(II)acetate
$Pd_2(dba)_2$=Bis(dibenzylidene acetone)dipalladium(0)
Pd(dppf)=Palladium diphenylphosphinoferrocene
$Pd(PPh_3)_4$=Tetrakistriphenylphosphine palladium (0)
$PPh_3$=Triphenylphosphine
±SEM=±Standard Error of Measurement
SPE=Solid-phase Extraction
t-BOC or Boc=Tert-Butoxycarbonyl
t-BuOK=Potassium tert-Butoxide
TEA=Triethylamine
TFA=Trifluoroacetic Acid
THF=Tetrahydrofuran
THP=Tetrahydropyranyl
TMS=Trimethylsilyl
TMS-Cl=Trimethylsilyl chloride
Tosylate=p-Toluenesulfonate
Tosyl=p-Toluenesulfonyl
Triflate or OTf=Trifluoromethanesulfonate
Triflyl=Trifluoromethanesulfonyl As used herein, unless otherwise noted, the term "isolated form" means that the compound is present in a form which is separate from any solid mixture with another compound(s), solvent system or biological environment. In an embodiment of the present invention, the compound of formula (I) is present in an isolated form.

As used herein, unless otherwise noted, the term "substantially pure form" means that the mole percent of impurities in the isolated compound is less than about 5 mole percent, preferably less than about 2 mole percent, more preferably, less than about 0.5 mole percent, most preferably, less than about 0.1 mole percent. In an embodiment of the present invention, the compound of formula (I) is present as a substantially pure form.

As used herein, unless otherwise noted, the term "substantially free of a corresponding salt form(s)" when used to described the compound of formula (I) means that mole percent of the corresponding salt form(s) in the isolated base of formula (I) is less than about 5 mole percent, preferably less than about 2 mole percent, more preferably, less than about 0.5 mole percent, most preferably less than about 0.1 mole percent. In an embodiment of the present invention, the compound of formula (I) is present in a form which is substantially free of corresponding salt form(s).

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; (d) delay or avoidance of the development of the disorder or condition; and/or the delay or avoidance of the progression of the disorder or condition.

One skilled in the art will recognize that wherein the present invention is directed to methods of prevention, a subject in need of thereof (i.e., a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (co-morbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product including the specified ingredients in the specified amounts, as well as any product which results, directly or indirectly, from combinations of the specified ingredients in the specified amounts.

As more extensively provided in this written description, terms such as "reacting" and "reacted" are used herein in reference to a chemical entity that is any one of: (a) the actually recited form of such chemical entity, and (b) any of the forms of such chemical entity in the medium which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

Examples of suitable solvents, bases, reaction temperatures, and other reaction parameters and components are provided in the detailed descriptions which follow herein. One skilled in the art will recognize that the listing of said examples is not intended, and should not be construed, as limiting in any way the invention set forth in the claims which follow thereafter. One skilled in the art will further recognize that wherein a reaction step of the present invention may be carried out in a variety of solvents or solvent systems, said reaction step may also be carried out in a mixture of the suitable solvents or solvent systems.

As used herein, unless otherwise noted, the term "leaving group" means a charged or uncharged atom or group which departs during a substitution or displacement reaction. Suitable examples include, but are not limited to, Br, Cl, I, mesylate, tosylate, triflate, and the like.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*. John Wiley & Sons, 1991. The protecting groups may be removed at a convenient subsequent stage using methods known from the art.

As used herein, unless otherwise noted, the term "nitrogen protecting group" means a group which may be attached to a nitrogen atom to protect said nitrogen atom from participating in a reaction and which may be readily removed following the reaction. Suitable nitrogen protecting groups include, but are not limited to carbamates groups of the formula —C(O)O—R wherein R is for example methyl, ethyl, t-butyl, benzyl, phenylethyl, $CH_2=CH—CH_2—$, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts. *Protective Groups in Organic Synthesis*, John Wiley & Sons, 1991.

As used herein, unless otherwise noted, the term "oxygen protecting group" means a group which may be attached to a oxygen atom to protect said oxygen atom from participating in a reaction and which may be readily removed following the reaction. Suitable oxygen protecting groups include, but are not limited to, acetyl, benzoyl, t-butyl-dimethylsilyl, trimethylsilyl (TMS), methoxymethyl (MOM), tetrahydropyranyl (THP), and the like. Other suitable oxygen protecting groups may be found in texts such as T. W. Greene & P. G. M. Wuts, *Protective Groups in Organic Synthesis*, John Wiley & Sons, 1991.

Where the processes for the preparation of the compounds according to the invention yield rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows $$[(Rmoles-Smoles)/(Rmoles+Smoles)]\times 100\%$$

where Rmoles and Smoles are the R and S mole fractions in the mixture such that Rmoles+Smoles=1. The enantiomeric excess may alternatively be calculated from the specific rotations of the desired enantiomer and the prepared mixture as follows:

$$ee=([\alpha-obs]/[\alpha-max])\times 100.$$

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in *Design of Prodrugs*, ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

General Synthetic Schemes

Compounds of formula (I) may be prepared according to the process outlined in Scheme 1, below.

yield the corresponding compound of formula (XIII), wherein $Q^1$ is hydrogen or $PG^1$, respectively.

Alternatively, a suitably substituted compound of formula (XI), wherein $A^1$ is $C_{1-2}$alkyl, a known compound or compound prepared by known methods, is reacted with $NH_3$ or a suitably substituted compound of formula (XII), wherein $PG^1$ is a suitably selected nitrogen protecting group such as Boc, Cbz, benzyl, 1-phenylethyl, and the like; in the pres-

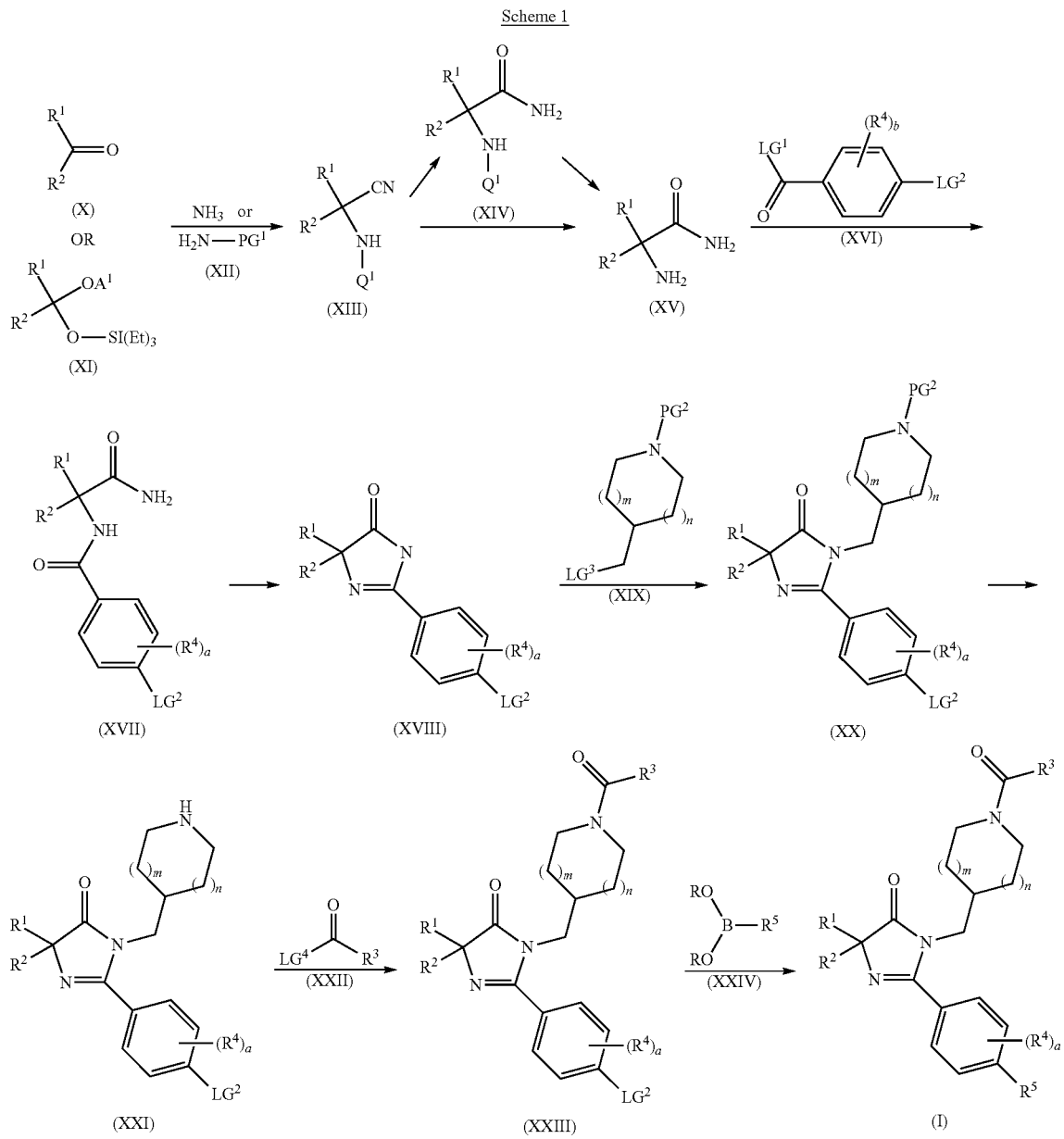

Scheme 1

Accordingly, a suitably substituted compound of formula (X), a known compound or compound prepared by known methods, is reacted with $NH_3$ or with a suitably substituted compound of formula (XII), wherein $PG^1$ is a suitably selected nitrogen protecting group such as Boc, Cbz, benzyl, 1-phenethyl, and the like; in the presence of a suitably selected source of cyanide, such as KCN, NaCN, TMS-CN, and the like; in a suitably selected solvent or mixture of solvents such as methanol, ethanol, water, and the like; to ence of a suitably selected source of cyanide, such as TMS-CN, and the like; in a suitably selected solvent or mixture of solvents such as glacial HOAc, and the like; to yield the corresponding compound of formula (XIII), wherein $Q^1$ is hydrogen or $PG^1$, respectively.

The compound of formula (XIII) is reacted to yield the corresponding compound of formula (XV), through a one-step or two step reaction.

Wherein the compound of formula (XIII) $Q^1$ is hydrogen, the compound of formula (XIII) is reacted with hydrogen peroxide, in the presence of a suitably selected inorganic base such as $K_2CO_3$, $Na_2CO_3$, and the like; in a suitably selected solvent such as DMSO, DMF, NMP, and the like; to yield the corresponding compound of formula (XV). Alternatively, the compound of formula (XIII) wherein $Q^1$ is hydrogen is reacted with a suitably selected acid such as conc. aq. $H_2SO_4$, and the like; in a suitably selected solvent such as DCM, and the like; to yield the corresponding compound of formula (XV).

Wherein the compound of formula (XIII) $Q^1$ is $PG^1$, the compound of formula (XIII) is reacted with is reacted with hydrogen peroxide, in the presence of a suitably selected inorganic base such as $K_2CO_3$, $Na_2CO_3$, and the like; in a suitably selected solvent such as DMSO, DMF, NMP, and the like; to yield the corresponding compound of formula (XIV), wherein $Q^1$ is $PG^1$. Alternatively, the compound of formula (XIII) wherein $Q^1$ is $PG^1$, is reacted with a suitably selected acid such as conc. aq. $H_2SO_4$, and the like; in a suitably selected solvent such as DCM, and the like; to yield the corresponding compound of formula (XIV), wherein $Q^1$ is $PG^1$. The compound of formula (XIV) is then de-protected according to known methods to remove the $PG^1$ group and yield the corresponding compound of formula (XV). For example, wherein $PG^1$ is benzyl, the compound of formula (XIV) is de-protected by reacting with hydrogen in the presence of a suitable selected catalyst such as Pd/C, and the like.

The compound of formula (XV) is reacted with a suitably substituted compound of formula (XVI), wherein $LG^1$ is a suitably selected leaving group such as Cl, Br, OH, and the like, and wherein $LG^2$ is a suitably selected leaving group such as Cl, Br, OH, triflate, $B(OH)_2$, $B(OC_{1-2}alkyl)_2$,

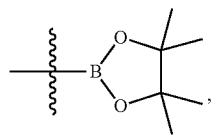 [SMILES: *B1OC(C)(C)C(C)(C)O1]

and the like, a known compound or compound prepared by known methods; to yield the corresponding compound of formula (XVII).

More particularly, wherein $LG^1$ is Cl, Br, and the like, the compound of formula (XV) is reacted with the compound of formula (XVI), in the presence of a suitably selected organic base such as pyridine, TEA, DIPEA, and the like; optionally in the presence of DMAP, and the like; in a suitably selected solvent such as DCM, DCE, THF, and the like; to yield the corresponding compound of formula (XVII). Alternatively, wherein $LG^1$ is OH, and the like, the compound of formula (XV) is reacted with the compound of formula (XVI), in the presence of a suitably selected coupling reagent such as HATU, HBTU, CDI, EDAC, and the like, in the presence of a suitably selected organic base such as pyridine, TEA, DIPEA, and the like; in a suitably selected organic solvent such as NMP, DMF, DCM, DCE, and the like, to yield the corresponding compound of formula (XVII).

The compound of formula (XVII) is reacted (to effect ring closure) with a suitably selected base such as t-BuOK, NaOH, $NaOCH_3$, LHMDS, and the like; in a suitably selected organic solvent or mixture of solvents such as methanol, ethanol, water, 1,4-dioxane, and the like, and wherein the base in LHMDS, in a suitably selected organic solvent such as THF, and the like; to yield the corresponding compound of formula (XVIII).

The compound of formula (XVIII) is reacted with a suitably substituted compound of formula (XIX), wherein $PG^2$ is a suitably selected nitrogen protecting group such as Boc, benzyl, Cbz, benzoyl, and the like, and wherein $LG^3$ is a suitably selected leaving group such as Br, I, Cl, mesylate, tosylate, triflate, and the like, a known compound or compound prepared by known methods; in the presence of a suitably selected base such as $K_2CO_3$, $Na_2CO_3$, NaH, and the like; in a suitably selected solvent such as DMF, DMP, THF, 1,4-doxane, and the like; to yield the corresponding compound of formula (XX).

The compound of formula (XX) is then de-protected according to known methods to yield the corresponding compound of formula (XXI). For example, wherein $PG^2$ is Boc, the compound of formula (XXI) is de-protected by reacting with a suitably selected acid, in a suitably selected organic solvent, for example reacting with HCl in 1,4-dioxane, or reacting with TFA in DCM.

The compound of formula (XXI) is reacted with a suitably substituted compound of formula (XXII), wherein $LG^4$ is a suitably selected leaving group such as Cl, Br, and the like, a known compound or compound prepared by known methods, in the presence of a suitably selected organic base such as pyridine, TEA, DIPEA, and the like; optionally in the presence of DMAP, and the like; in a suitably selected solvent such as DCM, DCE, THF, and the like; to yield the corresponding compound of formula (XXIII). Alternatively, the compound of formula (XXI) is reacted with a suitably substituted compound of formula (XXII), wherein $LG^4$ is a suitably selected leaving group such as OH, and the like; in the presence of a suitably selected coupling reagent such as HATU, HBTU, CDI, EDAC, and the like, in the presence of a suitably selected organic base such as pyridine, TEA, DIPEA, and the like; in a suitably selected organic solvent such as NMP, DMF, DCM, DCE, and the like; to yield the corresponding compound of formula (XXIII).

The compound of formula (XXIII) is reacted with a suitably substituted compound of formula (XXIV), wherein the two R groups are each H, are each the same $C_{1-2}$alkyl or are taken together as $-C(CH_3)_2-C(CH_3)_2-$ to form a ring (i.e. to form the

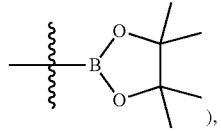

a known compound or compound prepared by known methods, under Suzuki coupling conditions, more particularly, in the presence of a suitably selected catalysts or catalyst system, such as $Pd(PPh_3)_4$, $Pd_2(dba)_3$, Pd(dppf), a mixture of $Pd(OAc)_2$ and $PPh_3$, and the like; in the presence of a suitably selected inorganic base such as $K_2CO_3$, $Cs_2CO_3$, $Na_2CO_3$, and the like; in a suitably selected solvent such as DME, 1,4-dioxane, and the like, preferably mixed with water; to yield the corresponding compound of formula (I).

Alternatively, wherein the compound of formula (XXIII), $LG^2$ is OH, the compound of formula (XXIII) may be reacted with triflic anhydride, in the presence of a suitably selected base such as TEA, pyridine, and the like, in a suitably selected solvent such as DCM, DCE, and the like; to convert the $LG^2$ leaving group from OH to triflate; and then reacting the resulting compound with a suitably substituted compound of formula (XXIV), as described above; to yield the corresponding compound of formula (I).

One skilled in the art will recognize that the $R^5$ substituent group may alternatively be incorporated into the desired compound of formula (I) by reacting a compound of formula (XXIII), wherein the LG² group is replaced with a group of the formula —B(OR)₂ (wherein the two R groups are each H, are each the same C₁₋₂alkyl or are taken together as —C(CH₃)₂—C(CH₃)₂— to form a ring (i.e. to form the

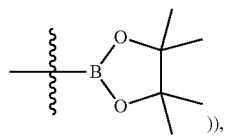 [SMILES: *B1OC(C)(C)C(C)(C)O1]

with a suitably substituted compound of formula (XXIV), wherein the —B(OR)₂ substituent is replaced with a suitably selected leaving group such as Cl, Br, triflate, and the like; under Suzuki coupling conditions, more particularly, in the presence of a suitably selected catalysts or catalyst system, such as Pd(PPh₃)₄, Pd₂(dba)₃, Pd(dppf), a mixture of Pd(OAc)₂ and PPh₃, and the like; in the presence of a suitably selected inorganic base such as K₂CO₃, Cs₂CO₃, Na₂CO₃, and the like; in a suitably selected solvent such as DME, 1,4-dioxane, and the like, preferably mixed with water.

Compounds of formula (I) may alternatively be prepared according to the process as outlined in Scheme 2, below.

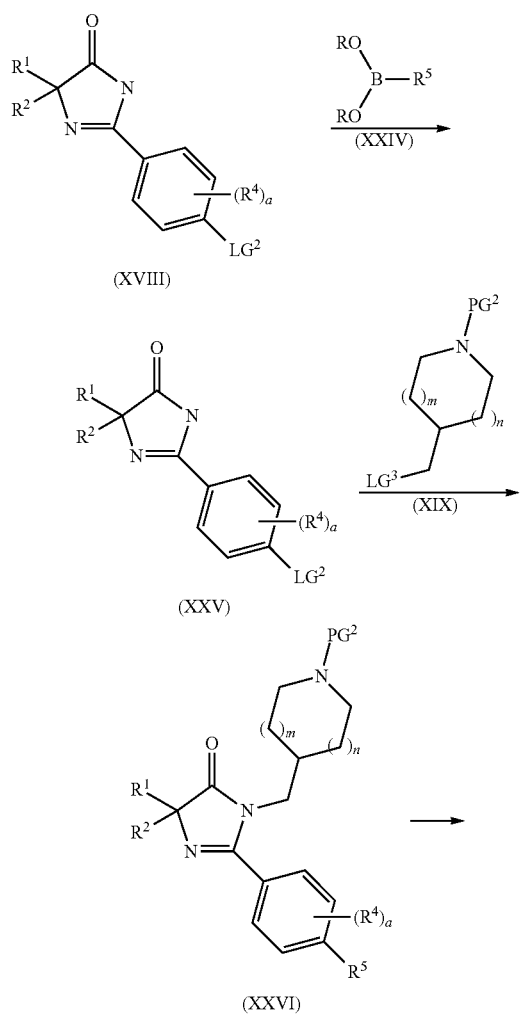

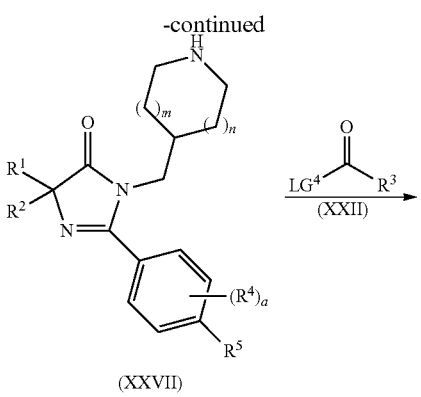

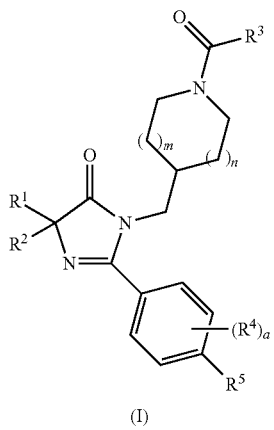

Accordingly, a suitably substituted compound of formula (XVIII), prepared for example as outlined in Scheme 1 above, is reacted with a suitably substituted compound of formula (XXIV), wherein the two R groups are each H, are each the same C₁₋₂alkyl or are taken together as —C(CH₃)₂—C(CH₃)₂— to form a ring (i.e. to form the

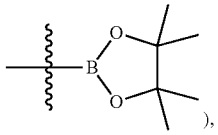

a known compound or compound prepared by known methods, under Suzuki coupling conditions, more particularly, in the presence of a suitably selected catalysts or catalyst system, such as Pd(PPh₃)₄, Pd₂(dba)₃, Pd(dppf), a mixture of Pd(OAc)₂ and PPh₃, and the like; in the presence of a suitably selected inorganic base such as K₂CO₃, Cs₂CO₃, Na₂CO₃, and the like; in a suitably selected solvent such as DME, 1,4-dioxane, and the like, preferably mixed with water; to yield the corresponding compound of formula (XV).

The compound of formula (XV) is reacted with a suitably substituted compound of formula (XIX), wherein PG² is a suitably selected nitrogen protecting group such as Boc, benzyl, Cbz, benzoyl, and the like, and wherein LG³ is a suitably selected leaving group such as Br, I, Cl, mesylate, tosylate, triflate, and the like, a known compound or compound prepared by known methods; in the presence of a suitably selected base such as K₂CO₃, Na₂CO₃, NaH, and the like; in a suitably selected solvent such as DMF, DMP, THF, 1,4-doxane, and the like; to yield the corresponding compound of formula (XXVI).

The compound of formula (XXVI) is de-protected according to known methods to yield the corresponding compound of formula (XXVII). For example, wherein PG² is Boc, the compound of formula (XXVI) is de-protected by reacting with a suitably selected acid, in a suitably selected organic solvent, for example reacting with HCl in 1,4-dioxane, or reacting with TFA in DCM.

The compound of formula (XXVII) is reacted with a suitably substituted compound of formula (XXII), wherein the like, in the presence of a suitably selected organic base such as pyridine, TEA, DIPEA, and the like; in a suitably selected organic solvent such as NMP, DMF, DCM, OCE, and the like; to yield the corresponding compound of formula (I).

Compounds of formula (I) may alternatively be prepared according to the process as outlined in Scheme 3, below.

Scheme 3

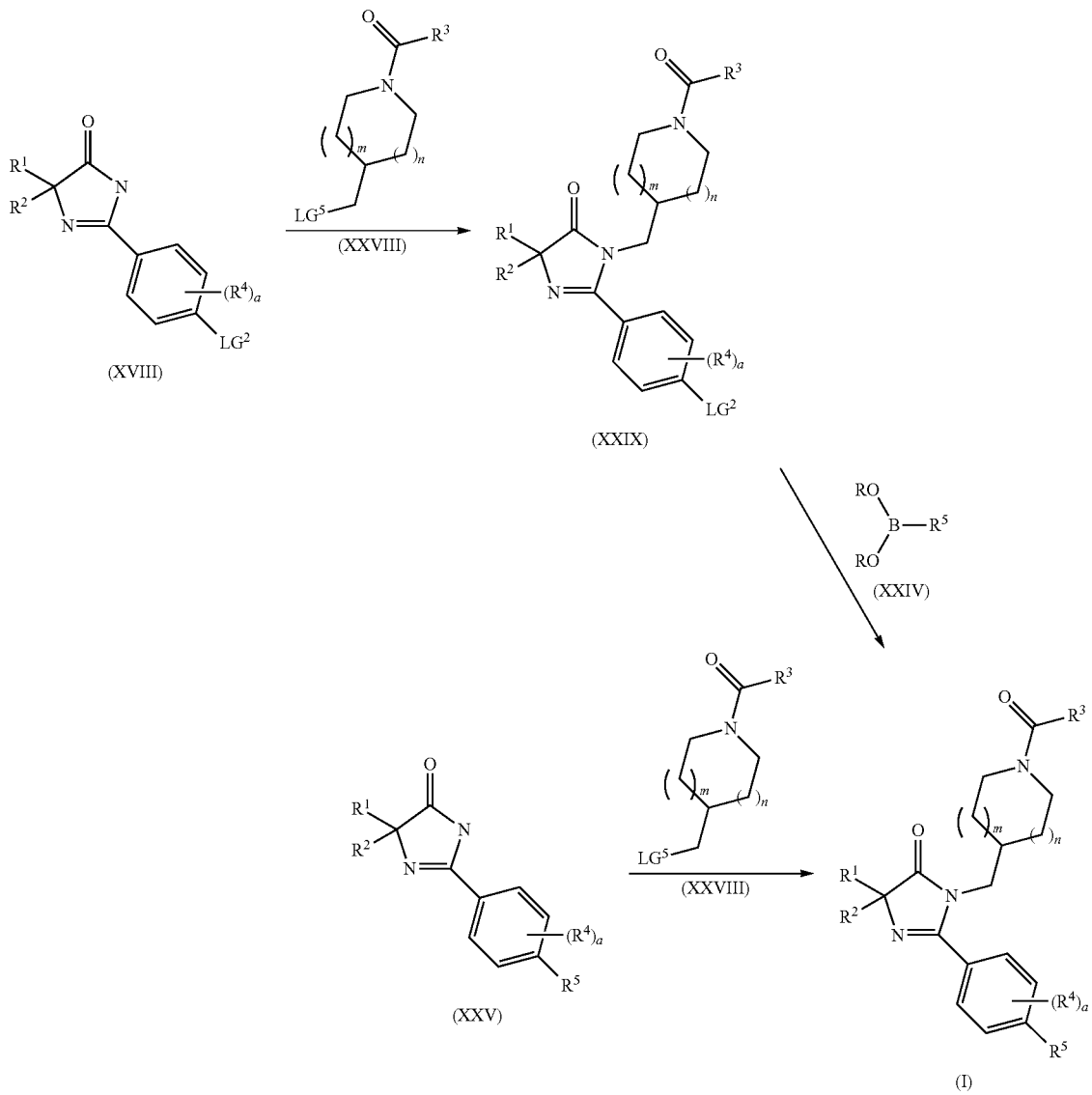

LG⁴ is a suitably selected leaving group such as Cl, Br, and the like, a known compound or compound prepared by known methods, in the presence of a suitably selected organic base such as pyridine, TEA, DIPEA, and the like; optionally in the presence of DMAP, and the like; in a suitably selected solvent such as DCM, DCE, THF, and the like; to yield the corresponding compound of formula (I). Alternatively, the compound of formula (XXVII) is reacted with a suitably substituted compound of formula (XXII), wherein LG⁴ is a suitably selected leaving group such as OH, and the like; in the presence of a suitably selected coupling reagent such as HATU, HBTU, CDI, EDAC, and Accordingly, a suitably substituted compound of formula (XVIII), prepared for example as outlined in Scheme 1 above, is reacted with a suitably substituted compound of formula (XXVIII), wherein LG⁵ is a suitably selected leaving group such as Cl, Br, I, mesylate, tosylate triflate, and the like, a known compound, a compound prepared by known methods, or a compound prepared for example as described in Scheme 4 which follows herein; in the presence of a suitably selected base such as K₂CO₃, Na₂CO₃, NaH, and the like; in a suitably selected solvent such as DMF, DMP, THF, 1,4-doxane, and the like; to yield the corresponding compound of formula (XXIX), The compound of formula (XXIX) is reacted with a suitably substituted compound of formula (XXIV), wherein the two R groups are each H, are each the same $C_{1-2}$alkyl or are taken together as —C(CH$_3$)$_2$—C(CH$_3$)$_2$— to form a ring (i.e. to form the

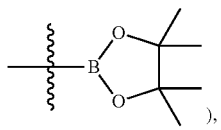 [SMILES: *B1OC(C)(C)C(C)(C)O1]

), a known compound or compound prepared by known methods, under Suzuki coupling conditions, more particularly, in the presence of a suitably selected catalysts or catalyst system, such as Pd(PPh$_3$)$_4$, Pd$_2$(dba)$_3$, Pd(dppf), a mixture of Pd(OAc)$_2$ and PPh$_3$, and the like; in the presence of a suitably selected inorganic base such as K$_2$CO$_3$, Cs$_2$CO$_3$, Na$_2$CO$_3$, and the like; in a suitably selected solvent such as DME, 1,4-dioxane, and the like, preferably mixed with water; to yield the corresponding compound of formula (I).

Alternatively, a suitably substituted compound of formula (XXV), prepared for example as described in Scheme 2 above, is reacted with a suitably substituted compound of formula (XXVIII), wherein LG$^5$ is a suitably selected leaving group such as Cl, Br, I, mesylate, tosylate, triflate, and the like, a known compound, a compound prepared by known methods, or a compound prepared for example as described in Scheme 4 which follows herein; in the presence of a suitably selected base such as K$_2$CO$_3$, Na$_2$CO$_3$, NaH, and the like; in a suitably selected solvent such as DMF, DMP, THF, 1,4-doxane, and the like; to yield the corresponding compound of formula (I).

The compound of formula (XXVIII) may be prepared for example, according to the process outlined in Scheme 4, below.

Accordingly, a suitably substituted compound of formula (XXX), a known compound or compound prepared by known methods (for example, by de-protecting the corresponding known, nitrogen-protected compound), is reacted with a suitably substituted compound of formula (XXII), wherein LG$^4$ is a suitably selected leaving group such as Cl, Br, and the like, a known compound or compound prepared by known methods, in the presence of a suitably selected organic base such as pyridine, TEA, DIPEA, and the like; optionally in the presence of DMAP, and the like; in a suitably selected solvent such as DCM, DCE, THF, and the like; to yield the corresponding compound of formula (XXXI). Alternatively, the compound of formula (XXX) is reacted with a suitably substituted compound of formula (XXII), wherein LG$^4$ is a suitably selected leaving group such as OH, and the like; in the presence of a suitably selected coupling reagent such as HATU, HBTU, CDI, EDAC, and the like, in the presence of a suitably selected organic base such as pyridine, TEA, DIPEA, and the like; in a suitably selected organic solvent such as NMP, DMF, DCM, DCE, and the like; to yield the corresponding compound of formula (XXXI).

The compound of formula (XXXI) is reacted with a suitably selected source of chlorine, such as POCl$_3$, SOCl$_2$, and the like; or suitably selected source of bromine, such as PBr$_3$, POBr$_3$, CBr$_4$ in combination with PPh$_3$, and the like; or suitably selected source of iodine, such as I$_2$ in the presence of PPh$_3$; or suitably selected source of mesylate, such as MsCl, and the like; or other suitable selected source of any other suitable LG$^5$ leaving group; according to known methods; to yield the corresponding compound of formula (XXVIII).

Compounds of formula (XXV) may be prepared, for example, according to the process outlined in Scheme 5, below.

Scheme 4

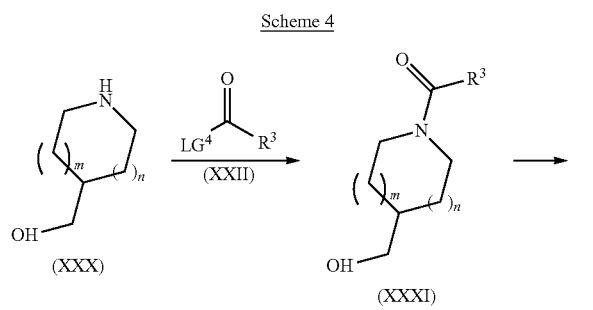

Scheme 5

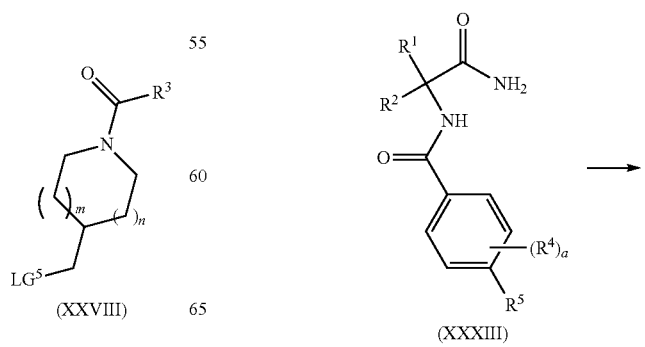

-continued

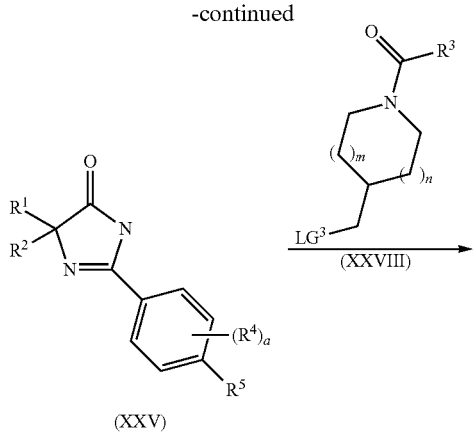

(XXV)

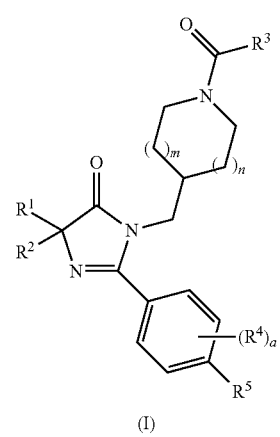

(I)

Accordingly, a suitably substituted compound of formula (XV), prepared for example as described in Scheme 1 above, is reacted with a suitably substituted compound of formula (XXXII), wherein $LG^6$ is a suitably selected leaving group such as Cl, Br, OH, and the like, to yield the corresponding compound of formula (XXXIII). More particularly, wherein $LG^6$ is is Cl, Br, and the like, the compound of formula (XV) is reacted with the compound of formula (XXXII), in the presence of a suitably selected organic base such as pyridine, TEA, DIPEA, and the like; optionally in the presence of DMAP, and the like; in a suitably selected solvent such as DCM, DCE, THF, and the like. Alternatively, wherein $LG^6$ is OH, and the like, the compound of formula (XV) is reacted with the compound of formula (XXXII), in the presence of a suitably selected coupling reagent such as HATU, HBTU, ODI, EDAC, and the like, in the presence of a suitably selected organic base such as pyridine, TEA, DIPEA, and the like; in a suitably selected organic solvent such as NMP, DMF, DCM, DCE, and the like.

The compound of formula (XXXIII) is reacted (to effect ring closure) with a suitably selected base such as t-BuOK, NaOH, NaOCH$_3$, LHMDS, and the like; in a suitably selected organic solvent or mixture of solvents such as methanol, ethanol, water, 1,4-dioxane, and the like, and wherein the base in LHMDS, in a suitably selected organic solvent such as THF, and the like; to yield the corresponding compound of formula (XXV).

The compound of formula (XXV) is reacted with a suitably substituted compound of formula (XXVIII), wherein $LG^5$ is a suitably selected leaving group such as Cl, Br, I, mesylate, tosylate, triflate, and the like, a known compound or compound prepared as described herein; in the presence of a suitably selected base such as K$_2$CO$_3$, Na$_2$CO$_3$, NaH, and the like; in a suitably selected solvent such as DMF, DMP, THF, 1,4-doxane, and the like; to yield the corresponding compound of formula (I).

One skilled in the art will recognize that alternatively, the compound of formula (XXV) may be reacted with a suitably substituted compound of formula (XIX), the resulting compound then de-protected and the de-protected compound further reacted with a suitably substituted compound of formula (XXII), to yield the corresponding compound of formula (I); according to the procedures as described in for, Scheme 1 or Scheme 2, above.

The compound of formula (XXIV) is a known compound or compound prepared for example, as described in Scheme 6, below.

Scheme 6

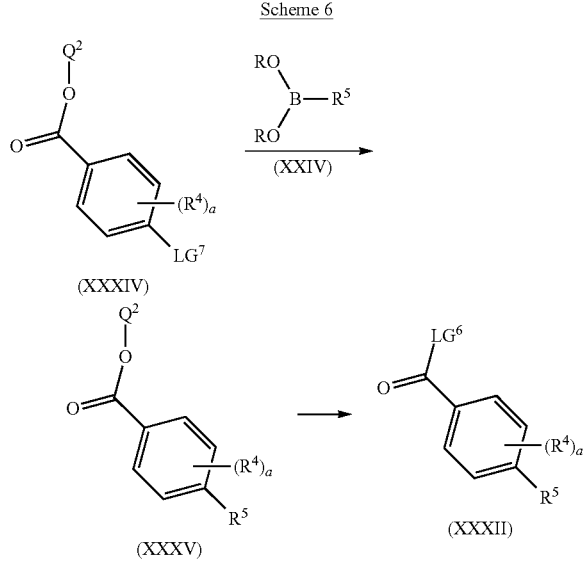

Accordingly, a suitable substituted compound of formula (XXXIV), wherein $Q^2$ is hydrogen or a suitably selected oxygen protecting group such as benzyl, $C_{1-4}$alkyl (preferably methyl, ethyl or t-butyl), and the like, and wherein $LG^7$ is a suitably selected leaving group such as Cl, Br, I, triflate, and the like, a known compound or compound prepared by known methods, is reacted with a suitably substituted compound of formula (XXIV), wherein the two R groups are each H, are each the same $C_{1-2}$alkyl or are taken together as —C(CH$_3$)$_2$—C(CH$_3$)$_2$— to form a ring (i.e. to form the

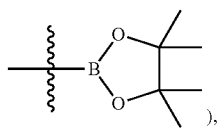

), a known compound or compound prepared by known methods, under Suzuki coupling conditions, more particularly, in the presence of a suitably selected catalysts or catalyst system, such as Pd(PPh$_3$)$_4$, Pd$_2$(dba)$_3$, Pd(dppf), a mixture of Pd(OAc)$_2$ and PPh$_3$, and the like; in the presence of a suitably selected inorganic base such as K$_2$CO$_3$, Cs$_2$CO$_3$, Na$_2$CO$_3$, and the like; in a suitably selected solvent such as DME, 1,4-dioxane, and the like, preferably mixed with water; to yield the corresponding compound of formula (XXXV).

The compound of formula (XXXV) is reacted to yield the corresponding compound of formula (XXXII), More particularly, wherein $Q^2$ is hydrogen, the compound of formula (XXXV) is reacted with a suitably selected source of chlorine, such as $POCl_3$, $SOCl_2$, and the like; or suitably selected source of bromine, such as $PBr_3$, and the like; or suitably selected source of iodine, such as $I_2$ in the presence of $PPh_3$; according to known methods; to yield the corresponding compound of formula (XXXII) wherein $LG^6$ is chloro, bromo or iodo, respectively. Alternatively, wherein $Q^2$ is a suitably selected oxygen protecting group, for example, benzyl, the compound of formula (XXXV) is de-protected by hydrogenolysis (reacting with hydrogen in the presence of a Pd/C catalyst), according to known methods; according to known methods, to yield the corresponding compound of formula (XXXII) wherein $LG^6$ is OH. Alternatively still, wherein $Q^2$ is a suitably selected oxygen protecting group such as t-butyl, the compound of formula (XXXV) is de-protected by with a suitably selected acid, in a suitably selected organic solvent, according to known methods (for example with HCl in 1,4-dioxane or with TEA in DCM), to yield the corresponding compound of formula (XXXII) wherein $LG^6$ is OH. Alternatively still, wherein $Q^2$ is a suitably selected oxygen protecting group such as $C_{1-4}$alkyl, and the like, for example methyl or ethyl, the compound of formula (XXXV) is de-protected by reacting with a suitably selected base, in a suitably selected mixture of water and an organic solvent, according to known methods (for example reacting with NaOH or KOH in a mixture of water, THF and methanol), to yield the corresponding compound of formula (XXXII), wherein $LG^6$ is OH.

Compounds of formula (I) may alternatively be prepared according to the process outlined in Scheme 7, below, Scheme 7

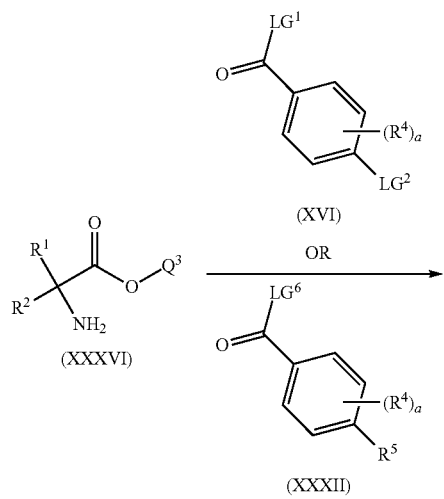

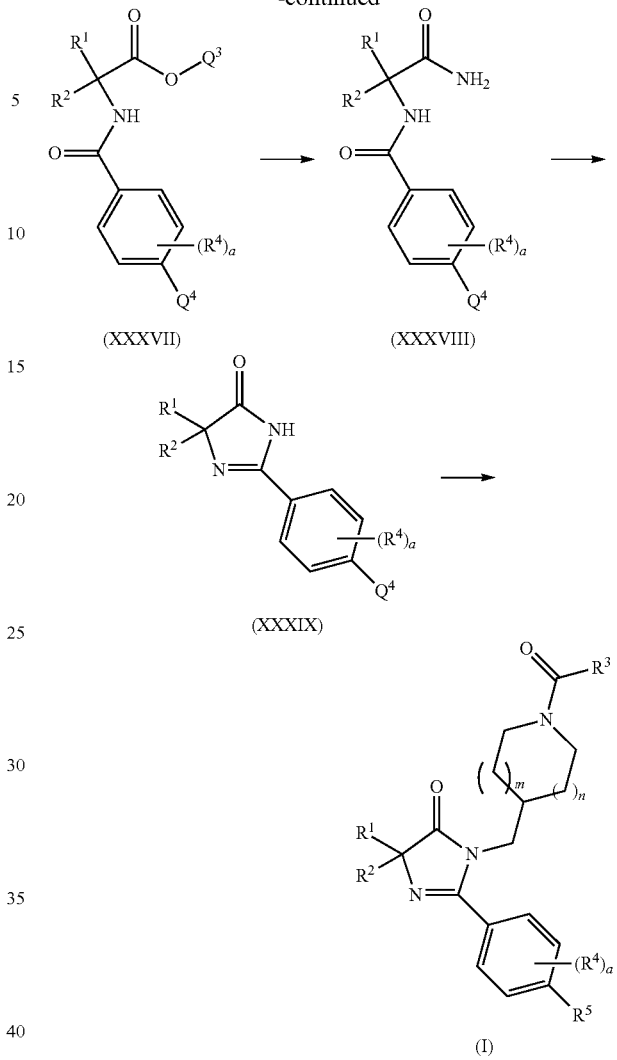

Accordingly, a suitably substituted compound of formula (XXXVI), wherein $Q^3$ is hydrogen or a suitably selected oxygen protecting group such as benzyl, $C_{1-4}$alkyl (preferably methyl, ethyl or t-butyl), and the like, a known compound or compound prepared by known methods, is reacted with a suitably substituted compound of formula (XVI), wherein $LG^1$ is a suitably selected leaving group such as Cl, Br, OH, and the like, and wherein $LG^2$ is a suitably selected leaving group such as Cl, Br, OH, triflate, $B(OH)_2$, $B(OC_{1-2}$alkyl$)_2$,

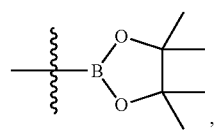

and the like, a known compound or compound prepared by known methods; according to known methods, for example, according to the process as outlined in Scheme 1 above; to yield the corresponding compound of formula (XXXVII), wherein $Q^4$ is the corresponding $LG^2$ group.

Alternatively, a suitably substituted compound of formula (XXXVI), wherein $Q^3$ is hydrogen or a suitably selected oxygen protecting group such as benzyl, $C_{1-4}$alkyl (preferably methyl, ethyl or t-butyl), and the like, a known compound or compound prepared by known methods; is reacted with a suitably substituted compound of formula (XXXII), wherein $LG^6$ is a suitably selected leaving group such as Cl, Br, OH, and the like, a known compound or compound prepared by known methods; according to known methods, for example, according to the process as outlined in Scheme 5 above; to yield the corresponding compound of formula (XXXVII) wherein $Q^4$ is $R^5$.

The compound of formula (XXXVII) is reacted to yield the corresponding compound of formula (XXXVIII). More particularly, wherein (a) $Q^3$ is hydrogen, the compound of formula (XXXVII) is reacted with ammonia or a suitably selected source of ammonia such as $NH_4Cl$, $NH_4OH$, gaseous $NH_3$, and the like; in the presence of a suitably selected coupling reagent such as HATU, HBTU, CDI, EDAC, and the like, in the presence of a suitably selected organic base such as pyridine, TEA, DIPEA, and the like; in a suitably selected organic solvent such as NMP, DMF, DCM, DCE, and the like; to yield the corresponding compound of formula (XXXVIII);

(b) $Q^3$ is a suitably selected oxygen protecting group such as methyl, ethyl and the like, the compound of formula (XXXVII) is reacted with ammonia or a suitably selected source of ammonia, such as concentrated $NH_4OH$, $NH_4Cl$, gaseous $NH_3$, and the like, according to known methods (for example as described in (a) above), to yield the corresponding compound of formula (XXXVIII); or (c) wherein $Q^3$ is a suitably selected oxygen protecting group such as benzyl, t-butyl, and the like, the compound of formula (XXXVII) is de-protected according to known methods (for example, wherein $Q^2$ is benzyl, t-butyl and the like, by hydrogenolysis, reacting with hydrogen in the presence of a catalyst such as Pd/C), or by reacting with a suitably selected acid, in a suitably selected organic solvent (for example reacting with HCl, in 1,4-dioxane or reacting with TFA in DCM), in a syu to yield the corresponding compound of formula (XXXVII) wherein $Q^3$ is hydrogen; which compound is then reacted with ammonia or a suitably selected source of ammonia as described in (a) above, to yield the corresponding compound of formula (XXXVIII).

The compound of formula (XXXVIII) is reacted (to effect ring closure) with a suitably selected base such as t-BuOK, NaOH, $NaOCH_3$, LHMDS, and the like; in a suitably selected organic solvent or mixture of solvents such as methanol, ethanol, water, 1,4-dioxane, and the like, and wherein the base in LHMDS, in a suitably selected organic solvent such as THF, and the like; to yield the corresponding compound of formula (XXXIX).

The compound of formula (XXXIX) is reacted, according to the procedures as described herein, to yield the desired compound of formula (I). For example, the compound of formula (XXXIX) wherein $Q^4$ is a suitably elected leaving group, may be substituted for the compound of formula (XVIII) in Scheme 1 reacted according to the procedure as described in Scheme 1, to yield the desired compound of formula (I). Alternatively, the compound of formula (XXXIX) wherein $Q^4$ is $R^5$ may be substituted for the compound of formula (XV) in Scheme 2 or the compound of formula (XXV) in Scheme 3, and reacted as described therein, respectively, to yield the corresponding compound of formula (I).

Pharmaceutical Compositions

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg to about 1000 mg or any amount or range therein, and may be given at a dosage of from about 0.01 mg/kg/day to about 300 mg/kg/day, or any amount or range therein, preferably from about 0.1 mg/kg/day to about 100 mg/kg/day, or any amount or range therein, preferably from about 0.50 mg/kg/day to about 50 mg/kg/day, or any amount or range therein, preferably from about 0.75 mg/kg/day to about 15 mg/kg/day, or any amount or range therein, preferably from about 1.0 mg/kg/day to about 7.5 mg/kg/day, or any amount or range therein, preferably from about 1.5 mg/kg/day to about 5.0 mg/kg/day, or any amount or range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.01 mg to about 1,000 mg, or any amount or range therein, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating disorders described in the present invention may also be carried out using a pharmaceutical composition comprising, consisting of and/or consisting essentially of any of the compounds as defined herein and a pharmaceutically acceptable carrier. The pharmaceutical composition may contain between about 0.01 mg and about 1000 mg of the compound, or any amount or range therein; preferably from about 1.0 mg to about 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methylcellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications, including *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of disorders mediated by inhibition of fatty acid synthase (FASN) enzyme, as described herein, is required.

The daily dosage of the products may be varied over a wide range from about 0.01 mg to about 1,000 mg per adult human per day, or any amount or range therein. For oral administration, the compositions are preferably provided in the form of tablets containing about 0.01, 0.05, 0.1, 0.5, 1.0, 2.5, 5.0, 10.0, 15.0, 25.0, 50.0, 100, 150, 200, 250, 500 and 1000 milligrams of the active ingredient for the symptomatic adjustment of the dosage to the patient to be treated. An effective amount of the drug is ordinarily supplied at a dosage level of from about 0.01 mg/kg to about 300 mg/kg of body weight per day, or any amount or range therein. Preferably, the range is from about 0.5 to about 50.0 mg/kg of body weight per day, or any amount or range therein. More preferably, from about 0.75 to about 15.0 mg/kg of body weight per day, or any amount or range therein. More preferably, from about 1.0 to about 7.5 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

SYNTHESIS EXAMPLES

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1: (R)-2-(4-(1H-Indol-5-yl)phenyl)-1-((1-(cyclopropanecarbonyl)pyrrolidin-3-yl)methyl)-4,4-dimethyl-1H-imidazol-5(4H)-one (Compound #1)

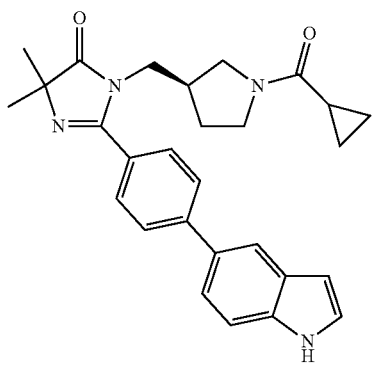 [SMILES: CC1(C)N=C(c2ccc(-c3ccc4[nH]ccc4c3)cc2)N(C[C@@H]2CCN(C(=O)C3CC3)C2)C1=O]

Step A: 2-(4-Bromobenzamido)-2-methylpropanoate

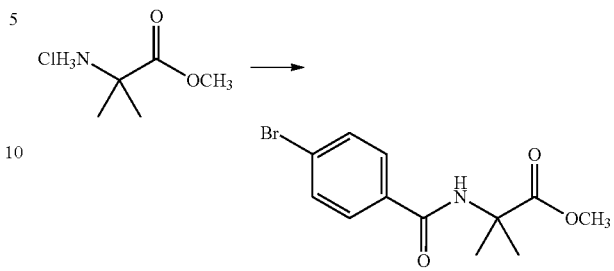

α-Aminoisobutyric acid methyl ester hydrochloride (2.68 g, 17.4 mmol) and triethylamine (6.06 mL, 43.6 mmol) were dissolved in anhydrous dichloromethane (100 mL). 4-Bromobenzoyl chloride (4.21 g, 19.2 mmol) was added slowly portion-wise with vigorous stirring. After 4 hours, the reaction was quenched with sat. aq. NaHCO$_3$ and extracted with dichloromethane. The extracts were concentrated to yield 2-(4-bromobenzamido)-2-methylpropanoate as a white solid.

$^1$H NMR (400 MHz, CD$_3$OD): δ 1.55 (s, 6H), 3.70 (s, 3H), 7.62 (d, J=9.1 Hz, 2H), 7.72 (d, J=9.1 Hz, 2H). MS (m/z): 299.9, 301.9.

Step B: N-(1-Amino-2-methyl-1-oxopropan-2-yl)-4-bromobenzamide

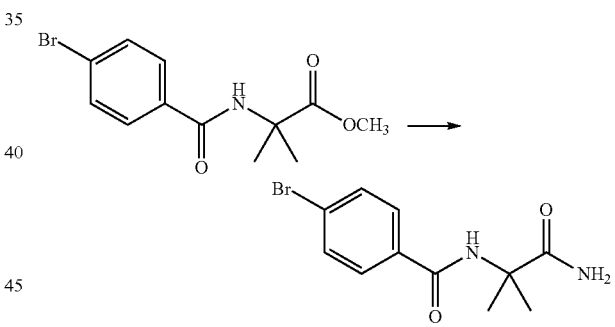

2-(4-Bromobenzamido)-2-methylpropanoate (3.96 g, 13.2 mmol) was suspended in concentrated ammonium hydroxide in a sealed pressure tube. The resulting mixture was heated to 100° C. for 16 hours and then concentrated to yield N-(1-amino-2-methyl-1-oxopropan-2-yl)-4-bromobenzamide as a white solid.

Step C: 2-(4-Bromophenyl)-4,4-dimethyl-1H-imidazol-5(4H)-one

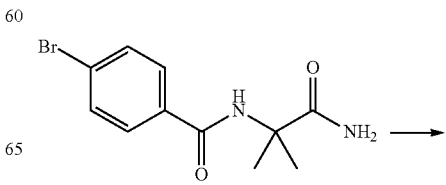

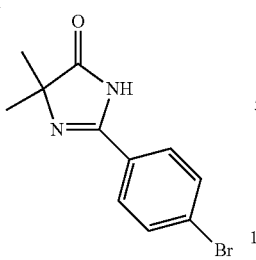

N-(1-Amino-2-methyl-1-oxopropan-2-yl)-4-bromobenzamide (3.00 g, 10.5 mmol) was suspended in methanol (200 mL) and then 6N aqueous NaOH (8.77 mL, 52.6 mmol) was added. The resulting mixture was heated to reflux. After 6 hours, the resulting mixture was diluted with brine and extracted with ethyl acetate. The organic extracts were concentrated to yield 2-(4-bromophenyl)-4,4-dimethyl-1H-imidazol-5(4H)-one as a white solid.

¹H NMR (400 MHz, CDCl₃): δ 1.47 (s, 6H), 7.67 (d, J=8.6 Hz, 2H), 7.83 (d, J=8.6 Hz, 2H), 10.85 (s, 1H).

Step D: (S)-tert-Butyl 3-((2-(4-bromophenyl)-4,4-dimethyl-5-oxo-4,5-dihydro-1H-imidazol-1-yl)methyl)pyrrolidine-1-carboxylate

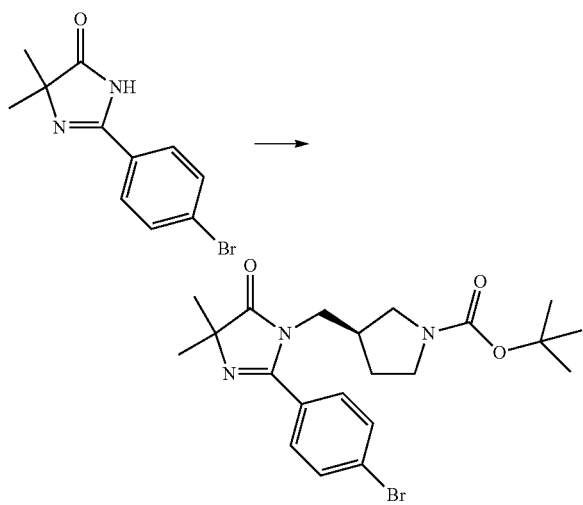

2-(4-Bromophenyl)-4,4-dimethyl-1H-imidazol-5(4H)-one (0.702 g, 2.63 mmol), (R)-tert-butyl 3-(bromomethyl)pyrrolidine-1-carboxylate (1.39 g, 5.26 mmol), and potassium carbonate (0.726 mg, 5.26 mmol) were combined in anhydrous dimethylformamide and the suspension was heated to 80° C. for 16 hours. Additional (R)-tert-butyl 3-(bromomethyppyrrolidine-1-carboxylate (500 mg) was added and the reaction was continued for another 24 hours. The resulting mixture was diluted with brine and extracted with ethyl acetate. The extracts were concentrated to an oil and chromatographed (40 g column, 10 to 50% EtOAc in heptane) to yield (S)-tert-butyl 3-((2-(4-bromophenyl)-4,4-dimethyl-5-oxo-4,5-dihydro-1H-imidazol-1-yl)methyppyrrolidine-1-carboxylate as a colorless oil.

¹H NMR (400 MHz, CDCl₃): δ 1.41 (s, 9H), 1.45 (s, 6H), 1.7-1.8 (m, 1H), 2.2-2.3 (m, 1H), 2.7-2.9 (m, 1H), 3.1-3.4 (m, 3H), 3.5-3.7 (m, 3H), 7.45 (d, J=8.6 Hz, 2H), 7.64 (d, J=8.6 Hz, 2H). MS (m/z): 449.9, 451.9.

Step E: (R)-2-(4-Bromophenyl)-4,4-dimethyl-1-(pyrrolidin-3-ylmethyl)-1H-imidazol-5(4H)-one

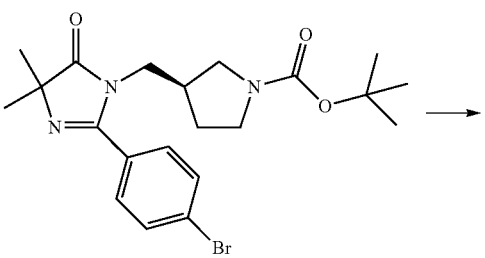

(S)-tert-Butyl 3-((2-(4-bromophenyl)-4,4-dimethyl-5-oxo-4,5-dihydro-1H-imidazol-1-yl)methyl)pyrrolidine-1-carboxylate (0.743 g, 1.65 mmol) was dissolved in a mixture of dichloromethane (50 mL) and trifluoromethanesulfonic acid (5 mL). The resulting solution was stirred for 16 hours at room temperature. The resulting mixture was then carefully diluted with saturated aqueous NaHCO₃. The resulting mixture was extracted with dichloromethane. The extracts were concentrated to yield (R)-2-(4-bromophenyl)-4,4-dimethyl-1-(pyrrolidin-3-ylmethyl)-1H-imidazol-5(4H)-one as a colorless oil.

¹H NMR (400 MHz, CDCl₃): δ 1.2-1.3 (m, 1H), 1.41 (s, 6H), 1.6-1.7 (m, 1H), 2.0-2.1 (m, 1H), 2.4-2.5 (m, 1H), 2.8-2.9 (m, 3H), 3.58 (d, J=8.1 Hz, 1H), 7.48 (d, J=8.6 Hz, 2H), 7.65 (d, J=8.6 Hz, 2H). MS (m/z): 350.0, 352.0.

Step F: (R)-2-(4-Bromophenyl)-1-((1-(cyclopropanecarbonyl)pyrrolidin-3-yl)methyl)-4,4-dimethyl-1H-imidazol-5(4H)-one

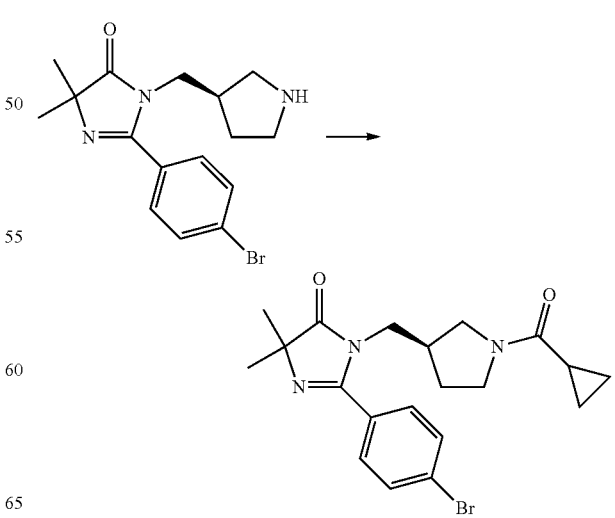

(R)-2-(4-Bromophenyl)-4,4-dimethyl-1-(pyrrolidin-3-yl-methyl)-1H-imidazol-5(4H)-one (0.341 g, 0.974 mmol) and triethylamine (0.338 mL, 2.43 mmol) were combined in anhydrous dichloromethane. Cyclopropanecarbonyl chloride (0.122 g, 1.17 mmol) was added slowly dropwise by syringe. The resulting solution was stirred at room temperature for 2 hours. The reaction was then neutralized with saturated aqueous NaHCO$_3$ and extracted with dichloromethane. The extracts were concentrated to a yellow oil and then chromatographed (40 g column, 5% MeOH in dichloromethane) to yield (R)-2-(4-bromophenyl)-1-((1-(cyclopropanecarbonyl)pyrrolidin-3-yl)methyl)-4,4-dimethyl-1H-imidazol-5(4H)-one as an off white solid.

$^1$H NMR (400 MHz, CDCl$_3$): δ 0.7-0.8 (m, 2H), 0.9-1.0 (m, 2H), 1.42-1.43 (m, 6H), 1.4-1.6 (m, 2H), 1.7-2.0 (m, 1H), 2.2-2.4 (m, 1H), 3.0-3.3 (m, 1H), 3.4-3.7 (m, 4H), 7.4-7.5 (m, 2H), 7.6-7.7 (m, 2H). MS (m/z): 417.9, 419.9.

Step G: (R)-2-(4-(1H-Indol-5-yl)phenyl)-1-((1-(cyclopropanecarbonyl)pyrrolidin-3-yl)methyl)-4,4-dimethyl-1H-imidazol-5(4H)-one (JNJ-54376179)

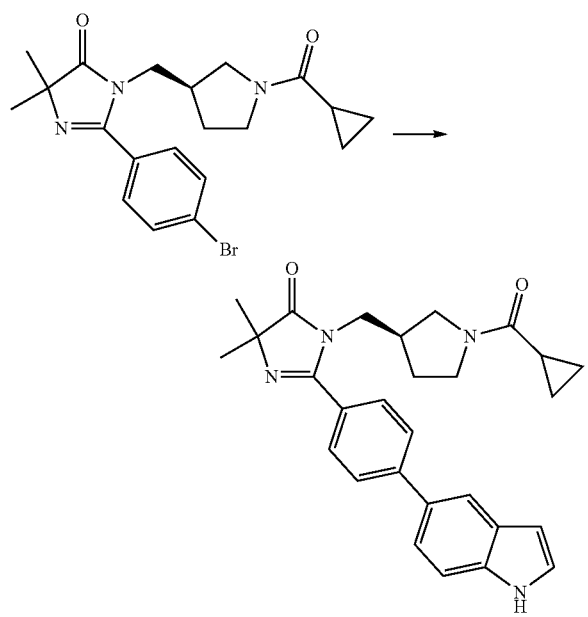

(R)-2-(4-Bromophenyl)-1-((1-(cyclopropanecarbonyl)pyrrolidin-3-yl)methyl)-4,4-dimethyl-1H-imidazol-5(4H)-one (0.083 g, 0.198 mmol), tetrakis(triphenylphosphine)palladium (0.023 g, 0.020 mmol), 1H-indol-5-yl-5-boronic acid (0.040 g, 0.248 mmol), and cesium carbonate (0.194 g, 0.595 mmol) were combined in dimethoxyethane (5 mL) and water (1 mL). The resulting mixture was heated to ~85° C. for 16 hours. The resulting mixture was then diluted with water and extracted with ethyl acetate. The extracts were concentrated to an oil and chromatographed (12 g column, 75:25 ethyl acetate:heptane to 100% ethyl acetate) to yield (R)-2-(4-(1H-indol-5-yl)phenyl)-1-((1-(cyclopropanecarbonyl)pyrrolidin-3-yl)methyl)-4,4-dimethyl-1H-imidazol-5(4H)-one as a white solid.

$^1$H NMR (400 MHz, CDCl$_3$): δ 0.6-0.7 (m, 2H), 0.9-1.0 (m, 2H), 1.45-1.46 (m, 6H), 1.4-1.6 (m, 2H), 1.8-1.9 (m, 1H), 2.3-2.5 (m, 1H), 3.0-3.3 (m, 1H), 3.5-3.8 (m, 4H), 6.6 (s, 1H), 7.46 (d, 2H), 7.63-7.66 (m, 2H), 7.76-7.80 (m, 2H), 7.91 (s, 1H), 8.62 (br s, 1H). MS (m/z): 455.3.

Example 2: (R)-2-(4-(benzofuran-5-yl)phenyl)-1-((1-(cyclopropanecarbonyl)pyrrolidin-3-yl)methyl)-4,4-dimethyl-1H-imidazol-5(4H)-one (Compound #3)

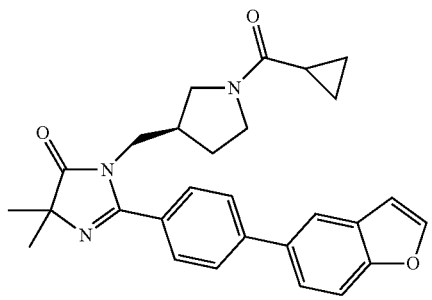 [SMILES: CC1(C)N=C(c2ccc(-c3ccc4occc4c3)cc2)N(C[C@@H]2CCN(C(=O)C3CC3)C2)C1=O]

Following the procedure as described in Example 1 above, (R)-2-(4-(benzofuran-5-yl)phenyl)-1-((1-(cyclopropanecarbonyl)pyrrolidin-3-yl)methyl)-4,4-dimethyl-1H-imidazol-5(4H)-one was prepared from alpha-aminoisobutyric acid methyl ester hydrochloride.

$^1$H NMR (400 MHz, CDCl$_3$): δ 0.69-0.72 (m, 2H), 0.89-0.98 (m, 2H), 1.45-1.46 (m, 6H), 1.42-1.63 (m, 1H), 1.81-1.98 (m, 1H), 2.31-2.51 (m, 1H), 3.0-3.8 (m, 6H), 6.84-6.85 (m, 1H), 7.54-7.61 (m, 2H), 7.66-7.69 (m, 3H), 7.74-7.78 (m, 2H), 7.84-7.85 (m, 1H). MS (m/z): 456.3.

Example 3: (R)-1-((1-(cyclopropanecarbonyl)pyrrolidin-3-yl)methyl)-4,4-dimethyl-2-(4-(1H-indazol-5-yl)phenyl)-1H-imidazol-5(4H)-one (Compound #2)

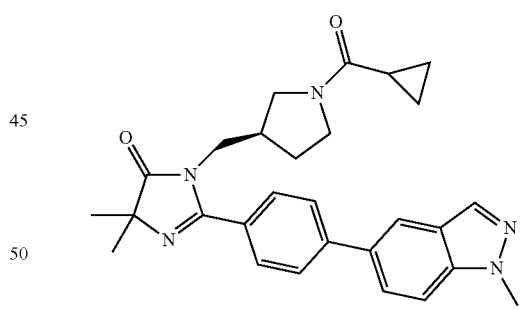

Following the procedure as described in Example 1 above, (R)-1-((1-(cyclopropanecarbonyl)pyrrolidin-3-yl)methyl)-4,4-dimethyl-2-(4-(1-methyl-1H-indazol-5-yl)phenyl)-1H-imidazol-5(4H)-one was prepared from alpha-aminoisobutyric acid methyl ester hydrochloride.

$^1$H NMR (400 MHz, CDCl$_3$): δ 0.69-0.72 (m, 2H), 0.89-0.98 (m, 2H), 1.45-1.46 (m, 6H), 1.42-1.68 (m, 1H), 1.80-1.99 (m, 1H), 2.31-2.52 (m, 1H), 3.0-3.8 (m, 6H), 4.13 (s, 3H), 7.49-7.51 (d, 1H, J=9.1 Hz), 7.66-7.69 (m, 3H), 7.76-7.79 (m, 2H), 7.98 (s, 1H), 8.06 (s, 1H). MS (m/z): 470.2.

Example 4: (R)-2-(4-(benzofuran-5-yl)phenyl)-1-((1-(1-fluorocyclopropanecarbonyl)pyrrolidin-3-yl)methyl)-4,4-dimethyl-1H-imidazol-5(4H)-one (Compound #4)

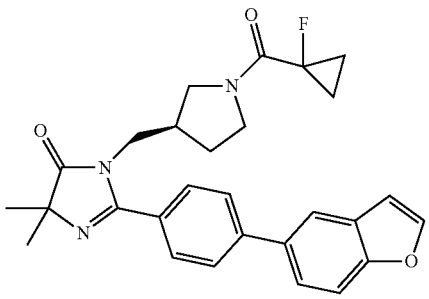 [SMILES: CC1(C)N=C(c2ccc(-c3ccc4occc4c3)cc2)N(C[C@@H]2CCN(C(=O)C3(F)CC3)C2)C1=O]

Following the procedure as described in Example 1 above, (R)-2-(4-(benzofuran-5-yl)phenyl)-1-((1-(1-fluorocyclopropanecarbonyl)pyrrolidin-3-yl)methyl)-4,4-dimethyl-1H-imidazol-5(4H)-one was prepared from α-aminoisobutyric acid methyl ester hydrochloride.

$^1$H NMR (400 MHz, CDCl$_3$): δ 1.11-1.37 (m, 4H), 1.46 (m, 6H), 1.55-1.96 (m, 1H), 2.32-2.346 (m, 1H), 3.07-3.78 (m, 6H), 6.84 (s, 1H), 7.45-7.84 (m, 8H). MS (m/z): 474.3.

Example 5: (4RS)-2-(4-(Benzofuran-5-yl)phenyl)-1-(((R)-1-(cyclopropanecarbonyl)pyrrolidin-3-yl)methyl)-4-methyl-4-phenyl-1H-imidazol-5(4H)-one (Compound #5)

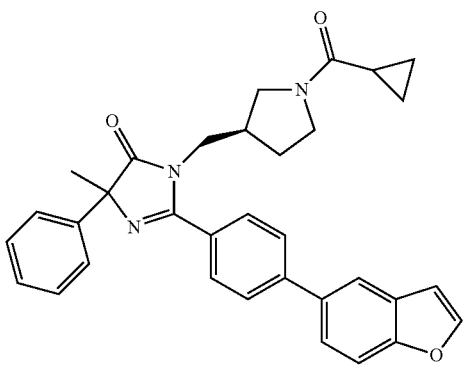 [SMILES: CC1(c2ccccc2)N=C(c2ccc(-c3ccc4occc4c3)cc2)N(C[C@@H]2CCN(C(=O)C3CC3)C2)C1=O]

Following the procedure as described in Example 1 above, (4RS)-2-(4-(benzofuran-5-yl)phenyl)-1-(((R)-1-(cyclopropanecarbonyl)pyrrolidin-3-yl)methyl)-4-methyl-4-phenyl-1H-imidazol-5(4H)-one was prepared from racemic 2-amino-2-phenyl-propionamide hydrochloride.

$^1$H NMR (400 MHz, CDCl$_3$): δ 0.6-0.7 (m, 2H), 0.8-0.9 (m, 2H), 1.4-1.6 (m, 2H), 1.75-1.90 (m, 1H), 1.80-1.82 (m, 3H), 2.3-2.5 (m, 1H), 3.0-3.3 (m, 2H), 3.4-3.6 (m, 2H), 3.6-3.8 (m, 2H), 6.84 (br s, 1H), 7.2-7.8 (m, 12H), 7.85 (br s, 1H). MS (m/z): 518.2.

Example 6: (4RS)-2-(4-(1H-Indol-5-yl)phenyl)-1-(((R)-1-(cyclopropanecarbonyl)pyrrolidin-3-yl)methyl)-4-methyl-4-phenyl-1H-imidazol-5(4H)-one (Compound #7)

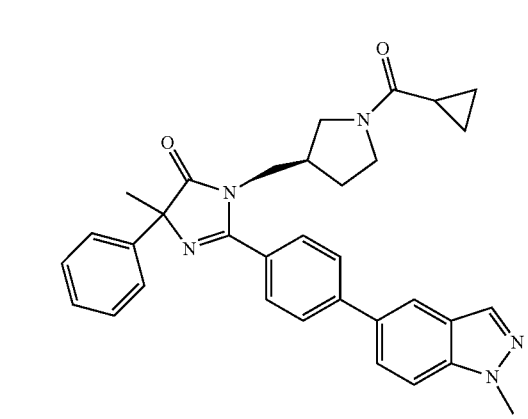 [SMILES: Cn1ncc2cc(-c3ccc(C4=NC(C)(c5ccccc5)C(=O)N4C[C@@H]4CCN(C(=O)C5CC5)C4)cc3)ccc21]

Following the procedure as described in Example 1 above, (4RS)-2-(4-(1H-indol-5-yl)phenyl)-1-(((R)-1-(cyclopropanecarbonyl)pyrrolidin-3-yl)methyl)-4-methyl-4-phenyl-1H-imidazol-5(4H)-one was prepared from racemic 2-amino-2-phenyl-propionamide hydrochloride.

$^1$H NMR (400 MHz, CDCl$_3$): δ 0.6-0.7 (m, 2H), 0.83-0.95 (m, 2H), 1.4-1.65 (m, 2H), 1.77-1.82 (m, 3H), 1.8-1.95 (1H, m), 2.2-2.5 (m, 1H), 3.0-3.3 (m, 2H), 3.4-3.6 (m, 2H), 3.6-3.8 (m, 2H), 6.62 (br s, 1H), 7.2-7.8 (m, 12H), 7.91 (br s, 1H), 8.73 (br s, 1H). MS (m/z): 516.9.

Example 7: (4RS)-1-(((R)-1-(cyclopropanecarbonyl)pyrrolidin-3-yl)methyl)-4-methyl-2-(4-(1-methyl-1H-indazol-5-yl)phenyl)-4-phenyl-1H-imidazol-5(4H)-one (Compound #6)

Following the procedure as described in Example 1 above, (4RS)-1-(((R)-1-(cyclopropanecarbonyl)pyrrolidin-3-yl)methyl)-4-methyl-2-(4-(1-methyl-1H-indazol-5-yl)phenyl)-4-phenyl-1H-imidazol-5(4H)-one was prepared from racemic 2-amino-2-phenyl-propionamide hydrochloride.

$^1$H NMR (400 MHz, CDCl$_3$): δ 0.6-0.7 (m, 2H), 0.86-0.95 (m, 2H), 1.4-1.65 (m, 2H), 1.79-1.82 (m, 6H), 1.8-1.95 (1H, m), 2.2-2.5 (m, 1H), 3.0-3.8 (m, 6H), 7.25-7.41 (m, 3H), 7.51 (d, 1H, J=8.6 Hz), 7.68-7.83 (m, 7H), 7.99 (s, 1H), 8.07 (s, 1H). MS (m/z): 531.9.

Example 8: (4RS)-2-(4-(Benzofuran-5-yl)phenyl)-1-(((R)-1-(cyclopropanecarbonyl)pyrrolidin-3-yl)methyl)-4-(methoxymethyl)-4-methyl-1H-imidazol-5(4H)-one (Compound #8)

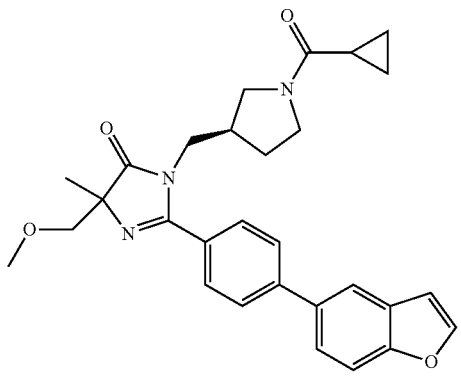 [SMILES: COCC1(C)N=C(c2ccc(-c3ccc4occc4c3)cc2)N(C[C@@H]2CCN(C(=O)C3CC3)C2)C1=O]

Following the procedure as described in Example 1 above, (4RS)-2-(4-(benzofuran-5-yl)phenyl)-1-(((R)-1-(cyclopropanecarbonyl)pyrrolidin-3-yl)methyl)-4-(methoxymethyl)-4-methyl-1H-imidazol-5(4H)-one was prepared from racemic 2-amino-3-methoxy-2-methylpropionamide hydrochloride.

$^1$H NMR (400 MHz, CDCl$_3$): δ 0.65-0.71 (m, 2H), 0.88-1.00 (m, 2H), 1.37-1.38 (m, 3H), 1.4-2.0 (m, 3H), 2.2-2.5 (1H, m), 3.0-3.3 (m, 2H), 3.32-3.35 (m, 3H), 3.43-3.84 (m, 6H), 6.84-6.85 (m, 1H), 7.55-7.61 (m, 2H), 7.69-7.71 (m, 3H), 7.74-7.78 (2H, m), 7.85 (1H, s). MS (m/z): 486.3.

Example 9: (4RS)-1-(((R)-1-(Cyclopropanecarbonyl)pyrrolidin-3-yl)methyl)-4-methoxymethyl)-4-methyl-2-(4-(1-methyl-1H-indazol-5-yl)phenyl)-1H-imidazol-5(4H)-one (Compound #10)

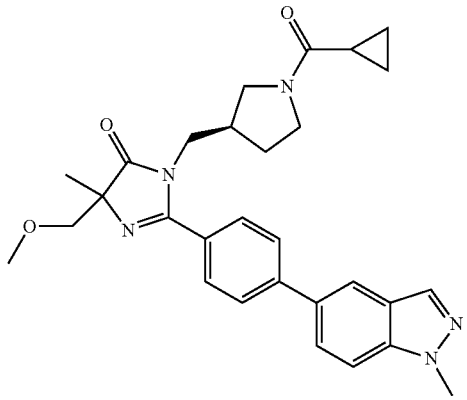 [SMILES: COCC1(C)N=C(c2ccc(-c3ccc4c(cnn4C)c3)cc2)N(C[C@@H]2CCN(C(=O)C3CC3)C2)C1=O]

Following the procedure as described in Example 1 above, (4RS)-1-(((R)-1-(cyclopropanecarbonyl)pyrrolidin-3-yl)methyl)-4-(methoxymethyl)-4-methyl-2-(4-(1-methyl-1H-indazol-5-yl)phenyl)-1H-imidazol-5(4H)-one was prepared from racemic 2-amino-3-methoxy-2-methylpropionamide hydrochloride.

$^1$H NMR (400 MHz, CDCl$_3$): δ 0.67-0.71 (m, 2H), 0.89-0.99 (m, 2H), 1.38 (s, 3H), 1.4-2.0 (m, 3H), 2.3-2.5 (m, 1H), 3.0-3.3 (m, 2H), 3.33-3.35 (m, 3H), 3.5-3.9 (m, 6H), 4.12 (s, 3H), 7.49-7.51 (m, 1H), 7.68-7.77 (m, 5H), 7.98 (s, 1H), 8.06 (s, 1H). MS (m/z): 500.3.

Example 10: (4RS)-2-(4-(Benzofuran-5-yl)phenyl)-1-(((R)-1-(cyclopropanecarbonyl)pyrrolidin-3-yl)methyl)-4-cyclopropyl-4-methyl-1H-imidazol-5(4H)-one (Compound #9)

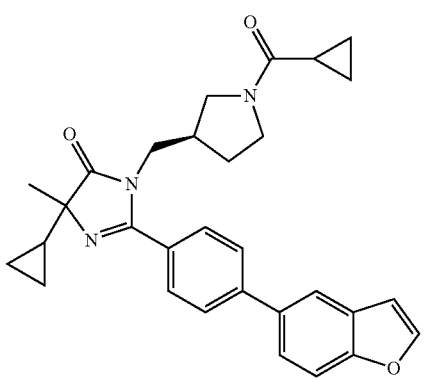 [SMILES: CC1(C2CC2)N=C(c2ccc(-c3ccc4occc4c3)cc2)N(C[C@@H]2CCN(C(=O)C3CC3)C2)C1=O]

Step A:
2-(4-Bromobenzamido)-2-cyclopropylpropanoic acid

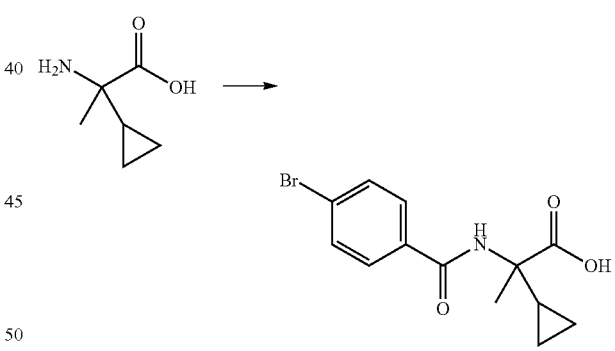

2-Cyclopropylalanine (0.900 g, 6.97 mmol) was dissolved in distilled water (20 mL). 6N Sodium hydroxide (1.16 mL, 6.97 mmol) and then the benzoyl chloride (1.53 g, 6.97 mmol) were added. The resulting heterogeneous mixture was stirred at room temperature for 16 hours. The resulting mixture was then concentrated to a white solid, taken up in acetic acid, and concentrated onto CELITE® for chromatography (gradient starting with 100% dichloromethane and ending with 89.5:10:0.5 dichloromethane:methanol:acetic acid). The fractions containing the product were concentrated to yield 2-(4-bromobenzamido)-2-cyclopropylpropanoic acid as a white solid.

MS (m/z): 312.0, 314.0.

Step B: N-(1-Amino-2-cyclopropyl-1-oxopropan-2-yl)-4-bromobenzamide

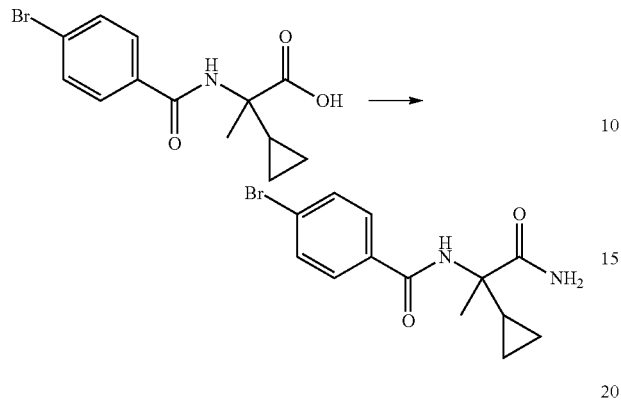

2-(4-Bromobenzamido)-2-cyclopropylpropanoic acid (2.00 g, 6.41 mmol) was suspended in anhydrous dichloromethane. Oxalyl chloride (2 M in dichloromethane, 4.80 mL, 9.61 mmol) and then 4 drops dimethylformamide were added. The resulting mixture was stirred at room temperature for two hours. Concentrated ammonium hydroxide (5.61 g, 160 mmol) was then added. The resulting mixture was concentrated to yield N-(1-amino-2-cyclopropyl-1-oxopropan-2-yl)-4-bromobenzamide as a white solid.

MS (m/z): 311.1 313.1.

Step C: (4RS)-2-(4-(Benzofuran-5-yl)phenyl)-1-(((R)-1-(cyclopropanecarbonyl)pyrrolidin-3-yl)methyl)-4-cyclopropyl-4-methyl-1H-imidazol-5(4H)-one (Compound #9)

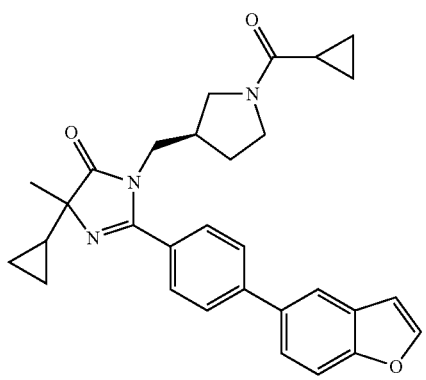 [SMILES: CC1(C2CC2)N=C(c2ccc(-c3ccc4occc4c3)cc2)N(C[C@@H]2CCN(C(=O)C3CC3)C2)C1=O]

Following the procedure as described in Example 1 above, (4RS)-2-(4-(Benzofuran-5-yl)phenyl)-1-(((R)-1-(cyclopropanecarbonyl)pyrrolidin-3-yl)methyl)-4-cyclopropyl-4-methyl-1H-imidazol-5(4H)-one was prepared from racemic N-(1-amino-2-cyclopropyl-1-oxopropan-2-yl)-4-bromobenzamide, prepared as in Step A-B above.

$^1$H NMR (400 MHz, CDCl$_3$): δ 0.22-0.29 (m, 1H), 0.35-0.44 (m, 1H), 0.50-0.59 (m, 1H), 0.61-0.74 (m, 3H), 0.89-0.98 (m, 2H), 1.30-1.36 (m, 1H), 1.42-1.52 (m, 1H), 1.57-1.71 (m, 1H), 1.79 (s, 3H), 1.84-1.98 (m, 1H), 2.29-2.49 (m, 1H), 3.0-3.3 (m, 1H), 3.5-3.8 (m, 5H), 6.85 (m, 1H), 7.44-7.76 (m, 7H), 7.83 (br s, 1H). MS (m/z): 482.2.

The following compounds were similarly prepared according to the procedures as described herein, selecting and substituting suitably substituted reagents, as would be readily recognized by those skilled in the art.

Example 11: 2-(4-(benzo[d]oxazol-2-yl)-2-fluorophenyl)-1-((1-(cyclopropanecarbonyl)azetidin-3-yl)methyl)-4,4-dimethyl-1H-imidazol-5(4H)-one (Compound #52)

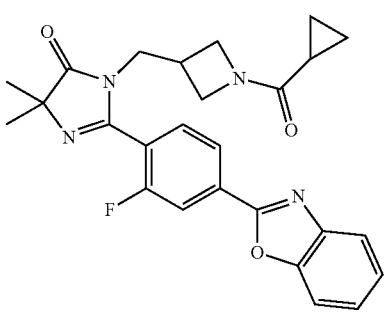 [SMILES: CC1(C)N=C(c2ccc(-c3nc4ccccc4o3)cc2F)N(CC2CN(C(=O)C3CC3)C2)C1=O]

$^1$H NMR (300 MHz, CHLOROFORM-d) δ 0.35-0.53 (m, 2H), 0.59-0.73 (m, 2H), 1.04 (m, 1H), 1.22 (s, 6H), 2.51 (br. s., 1H), 3.18-3.37 (m, 1H), 3.47 (d, J=6.05 Hz, 1H), 3.57 (d, J=8.11 Hz, 1H), 3.63-3.79 (m, 2H), 3.98 (t, J=7.90 Hz, 1H), 7.13-7.28 (m, 2H), 7.40 (dd, J=3.02, 5.36 Hz, 1H), 7.48 (t, J=7.35 Hz, 1H), 7.55-7.68 (m, 1H), 7.90 (d, J=10.31 Hz, 7.99 (d, J=7.84 Hz, 1H), 1H). MS m/z 461 (M+H)$^+$

Example 12: 2-(4-(benzo[d]thiazol-2-yl)-2-fluorophenyl)-1-((1-(cyclopropanecarbonyl)azetidin-3-yl)methyl)-4,4-dimethyl-1H-imidazol-5(4H)-one (Compound #34)

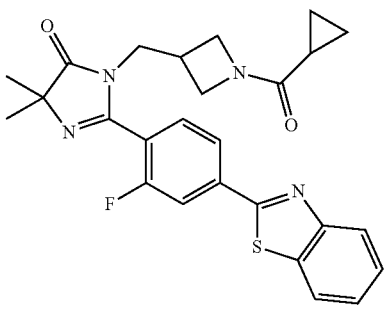 [SMILES: CC1(C)N=C(c2ccc(-c3nc4ccccc4s3)cc2F)N(CC2CN(C(=O)C3CC3)C2)C1=O]

$^1$H NMR (300 MHz, DMSO-d$_6$) δ 0.53-0.69 (m, 4H), 1.33 (s, 6H), 1.36-1.47 (m, 1H), 2.62 (br. s., 1H), 3.36-3.45 (m, 1H), 3.62-3.74 (m, 2H), 3.74-3.87 (m, 2H), 4.17 (t, J=8.39 Hz, 1H), 7.48-7.67 (m, 2H), 7.80-7.93 (m, 1H), 8.14 (d, J=8.66 Hz, 3H), 8.24 (d, J=7.84 Hz, 1H). MS m/z 477 (M+H)$^+$

Example 13: 1-((1-(cyclopropanecarbonyl)azetidin-3-yl)methyl)-2-(3-fluoro-4'-(1-methyl-1H-pyrazol-4-yl)-[1,1'-biphenyl]-4-yl)-4,4-dimethyl-1H-imidazol-5(4H)-one (Compound #33)

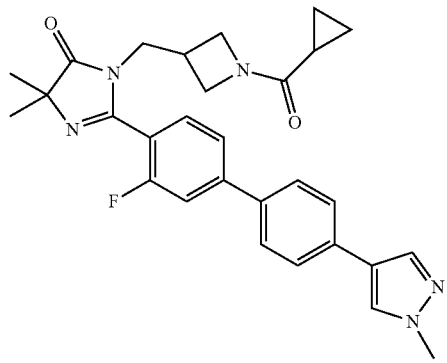 [SMILES: Cn1cc(-c2ccc(-c3ccc(C4=NC(C)(C)C(=O)N4CC4CN(C(=O)C5CC5)C4)c(F)c3)cc2)cn1]

$^1$H NMR (300 MHz, DMSO-d$_6$) δ 0.53-0.72 (m, 4H), 1.32 (s, 6H), 1.35-1.45 (m, 1H), 2.46-2.54 (m, 1H), 2.61 (br. s., 1H), 3.65 (s, 1H), 3.68 (s, 1H), 3.72-3.82 (m, 2H), 3.89 (s, 3H), 4.16 (t, J=8.39 Hz, 1H), 7.62-7.80 (m, 4H), 7.80-7.90 (m, 3H), 7.97 (s, 1H), 8.25 (s, 1H). MS m/z 500 (M+H)$^+$

Example 14: 1-((1-(cyclopropanecarbonyl)azetidin-3-yl)methyl-2-(2-fluoro-4-(quinolin-3-yl)phenyl)-4,4-dimethyl-1H-imidazol-5(4H)-one (Compound #20)

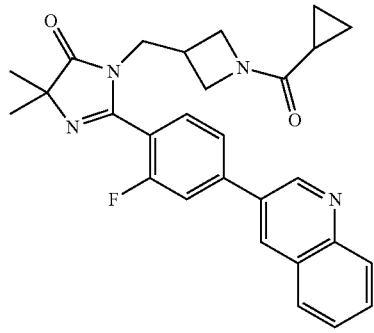 [SMILES: CC1(C)N=C(c2ccc(-c3cnc4ccccc4c3)cc2F)N(CC2CN(C(=O)C3CC3)C2)C1=O]

$^1$H NMR (300 MHz, DMSO-d$_6$) δ ppm 0.53-0.71 (m, 4H), 1.34 (s, 6H), 1.36-1.44 (m, 1H), 2.55-2.75 (m, 1H), 3.40 (dd, J=9.6, 6.0 Hz, 1H), 3.69 (d, J=7.6 Hz, 2H), 3.73-3.86 (m, 2H), 4.18 (t, J=8.4 Hz, 1H), 7.63-7.75 (m, 1H), 7.76-7.89 (m, 2H), 7.96-8.04 (m, 1H), 8.04-8.16 (m, 3H), 8.86 (d, J=1.9 Hz, 1H), 9.38 (d, J=2.2 Hz, 1H). MS m/z 471 (M+H)$^+$ Example 15: 1-((1-(cyclopropanecarbonyl)azetidin-3-yl)methyl)-2-(2-fluoro-4-(isoquinolin-5-yl)phenyl)-4,4-dimethyl-1H-imidazol-5(4H)-one (Compound #21)

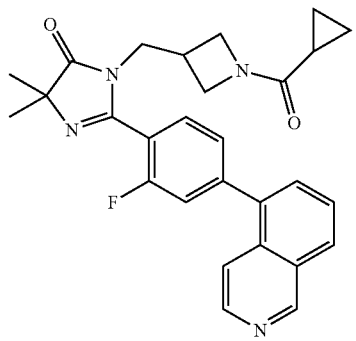 [SMILES: CC1(C)N=C(c2ccc(-c3cccc4cnccc34)cc2F)N(CC2CN(C(=O)C3CC3)C2)C1=O]

$^1$H NMR (300 MHz, DMSO-d$_6$) δ 0.55-0.76 (m, 4H), 1.25-1.37 (m, 6H), 1.37-1.49 (m, 1H), 2.67 (br. s., 1H), 3.38-3.47 (m, 1H), 3.73 (d, J=7.56 Hz, 2H), 3.76-3.87 (m, 2H), 4.21 (t, J=8.32 Hz, 1H), 7.47-7.60 (m, 2H), 7.60-7.74 (m, 2H), 7.81 (t, J=7.56 Hz, 1H), 7.88 (t, J=7.77 Hz, 1H), 8.14 (d, J=8.39 Hz, 1H), 8.27 (d, J=8.52 Hz, 1H), 8.99 (d, J=3.57 Hz, 1H). MS m/z 471 (M+H)$^+$

Example 16: 1-((1-(cyclopropanecarbonyl)azetidin-3-yl)methyl)-2-(2-fluoro-4-(quinolin-7-yl)phenyl)-4,4-dimethyl-1H-imidazol-5(4H)-one (Compound #39)

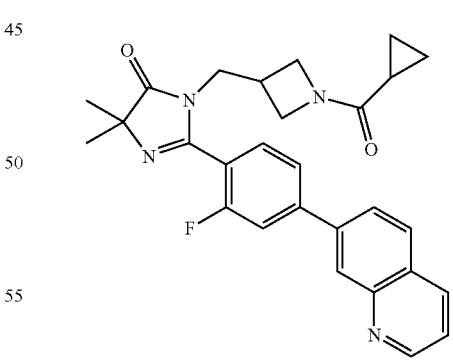

$^1$H NMR (300 MHz, DMSO-d$_6$) δ ppm 0.29-0.51 (m, 4H), 1.07-1.15 (m, 6H), 1.15-1.25 (m, 1H), 2.34-2.54 (m, 1H), 3.19 (dd, J=9.4, 5.6 Hz, 1H), 3.39-3.67 (m, 4H), 3.96 (t, J=8.3 Hz, 1H), 7.38 (dd, J=8.2, 4.2 Hz, 1H), 7.49-7.64 (m, 1H), 7.70-8.02 (m, 4H), 8.18-8.35 (m, 2H), 8.73-8.89 (m, 1H). MS m/z 471 (M+H)$^+$ Example 17: 1-((1-(cyclopropanecarbonyl)azetidin-3-yl)methyl)-2-(2-fluoro-4-(quinolin-6-yl)phenyl)-4,4-dimethyl-1H-imidazol-5(4H)-one
(Compound #38)

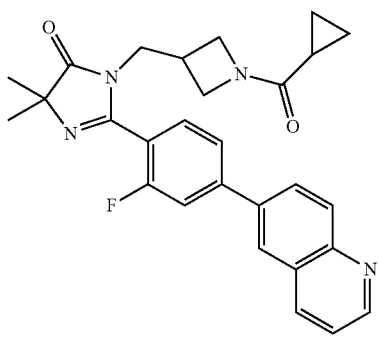 [SMILES: CC1(C)N=C(c2ccc(-c3ccc4ncccc4c3)cc2F)N(CC2CN(C(=O)C3CC3)C2)C1=O]

¹H NMR (300 MHz, DMSO-d$_6$) δ ppm 0.52-0.70 (m, 4H), 1.26-1.35 (m, 6H), 1.36-1.45 (m, 1H), 2.57-2.75 (m, 1H), 3.37-3.46 (m, 1H), 3.62-3.73 (m, 2H), 3.73-3.86 (m, 2H), 4.18 (t, J=8.3 Hz, 1H), 7.62 (dd, J=8.2, 4.1 Hz, 1H), 7.74-7.86 (m, 1H), 7.88-8.06 (m, 2H), 8.10-8.19 (m, 1H), 8.19-8.31 (m, 1H), 8.40-8.56 (m, 2H), 8.96 (d, J=3.0 Hz, 1H). MS m/z 471 (M+H)⁺

Example 18: 1-((1-(cyclopropanecarbonyl)azetidin-3-yl)methyl)-2-(2-fluoro-4-(1-methyl-1H-indazol-5-yl)phenyl)-4,4-dimethyl-1H-imidazol-5(4H)-one
(Compound #32)

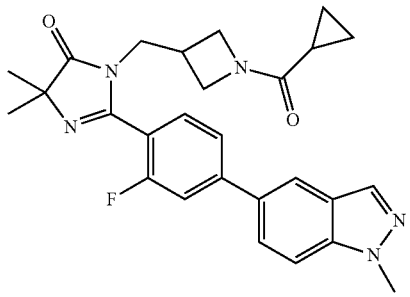 [SMILES: Cn1ncc2cc(-c3ccc(C4=NC(C)(C)C(=O)N4CC4CN(C(=O)C5CC5)C4)c(F)c3)ccc21]

¹H NMR (300 MHz, DMSO-d$_6$) δ ppm 0.30-0.44 (m, 4H), 1.08 (s, 6H), 1.11-1.19 (m, 1H), 2.38 (br. s., 1H), 3.12-3.21 (m, 1H), 3.43 (d, J=7.4 Hz, 2H), 3.47-3.59 (m, 2H), 3.86 (s, 3H), 3.88-3.98 (m, 1H), 7.41-7.51 (m, 1H), 7.53-7.69 (m, 4H), 7.91 (s, 1H), 7.99 (s, 1H). MS m/z 474 (M+H)⁺

Example 19: 1-((1-(cyclopropanecarbonyl)azetidin-3-yl)methyl)-2-(3-fluoro-4'-(pyridin-4-yl)-[1,1'-biphenyl]-4-yl)-4,4-dimethyl-1H-imidazol-5(4H)-one
(Compound #22)

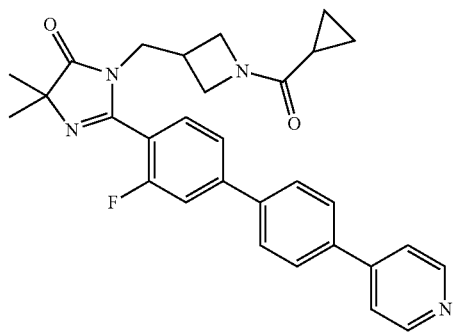 [SMILES: CC1(C)N=C(c2ccc(-c3ccc(-c4ccncc4)cc3)cc2F)N(CC2CN(C(=O)C3CC3)C2)C1=O]

¹H NMR (300 MHz, DMSO-d$_6$) δ ppm 0.53-0.74 (m, 4H), 1.33 (s, 6H), 1.36-1.46 (m, 1H), 2.61 (d, J=7.4 Hz, 1H), 3.36-3.46 (m, 1H), 3.61-3.73 (m, 2H), 3.73-3.85 (m, 2H), 4.17 (t, J=8.4 Hz, 1H), 7.71-7.94 (m, 5H), 7.94-8.06 (m, 4H), 8.68 (d, J=5.9 Hz, 2H). MS m/z 497 (M+H)⁺

Example 20: (R)-2-(4-(benzo[d]oxazol-2-yl)-2-fluorophenyl)-1-((1-(cyclopropanecarbonyl)pyrrolidin-3-yl)methyl)-4,4-dimethyl-1H-imidazol-5(4H)-one
(Compound #51)

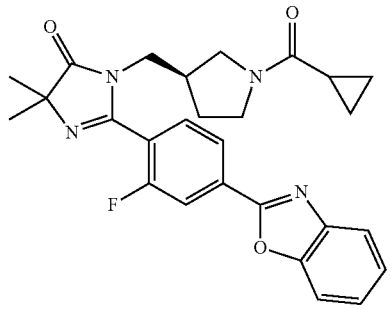 [SMILES: CC1(C)N=C(c2ccc(-c3nc4ccccc4o3)cc2F)N(C[C@@H]2CCN(C(=O)C3CC3)C2)C1=O]

¹H NMR (300 MHz, CHLOROFORM-d) δ ppm 0.36-0.58 (m, 2H), 0.60-0.82 (m, 2H), 1.14-1.31 (m, 6H), 1.35-1.45 (m, 1H), 1.66-1.84 (m, 0.5H), 2.01-2.33 (m, 1H), 2.72 (dd, J=11.9, 7.1 Hz, 1H), 2.87-3.15 (m, 0.5H), 3.16-3.31 (m, 2H), 3.32-3.47 (m, 2H), 7.14-7.28 (m, 2H), 7.36-7.46 (m, 1H), 7.49 (t, J=7.4 Hz, 1H), 7.56-7.68 (m, 1H), 7.88 (d, J=5.5 Hz, 1H), 7.99 (d, J=7.7 Hz, 1H). MS m/z 475 (M+H)⁺

Example 21: (R)-2-(4-(benzo[d]thiazol-2-yl)-2-fluorophenyl)-1-((1-(cyclopropanecarbonyl)pyrrolidin-3-yl)methyl)-4,4-dimethyl-1H-imidazol-5(4H)-one (Compound #50)

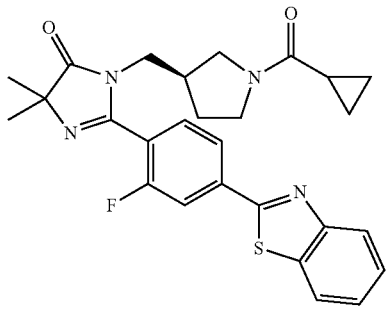

$^1$H NMR (300 MHz, CHLOROFORM-d) δ ppm 0.65-0.80 (m, 2H), 0.88-1.03 (m, 2H), 1.43-1.55 (m, 6H), 1.59-1.70 (m, 1H), 1.92-2.03 (m, 0.5H), 2.28-2.57 (m, 1H), 2.97 (dd, J=12.0, 7.0 Hz, 0.5H), 3.13-3.38 (m, 1H), 3.42-3.56 (m, 3H), 3.56-3.73 (m, 3H), 7.49 (d, J=7.7 Hz, 1H), 7.57 (t, J=7.6 Hz, 1H), 7.64-7.77 (m, 4H), 7.91-8.10 (m, 3H), 8.13 (d, J=8.1 Hz, 1H). MS m/z 491 (M+H)$^+$ Example 22: (R)-1-(1-(cyclopropanecarbonyl)pyrrolidin-3-yl)methyl)-2-(2-fluoro-4-(quinolin-6-yl)phenyl)-4,4-dimethyl-1H-imidazol-5(4H)-one (Compound #37)

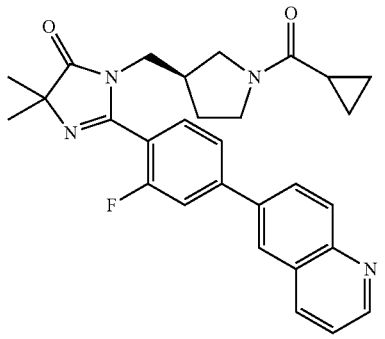 [SMILES: CC1(C)N=C(c2ccc(-c3ccc4ncccc4c3)cc2F)N(C[C@@H]2CCN(C(=O)C3CC3)C2)C1=O]

$^1$H NMR (300 MHz, DMSO-d$_6$) δ ppm 0.28-0.45 (m, 4H), 1.10 (br. s., 6H), 1.20-1.40 (m, 1.5H), 1.45-1.54 (m, 0.5H), 1.56-1.70 (m, 0.5H), 1.85-2.03 (m, 0.5H), 2.03-2.17 (m, 0.5H), 2.54-2.67 (m, 0.5H), 2.77-2.95 (m, 1H), 2.95-3.06 (m, 1H), 3.17-3.37 (m, 4H), 7.31-7.45 (m, 1H), 7.49-7.63 (m, 1H), 7.63-7.82 (m, 2H), 7.82-7.95 (m, 1H), 7.96-8.11 (m, 1H), 8.14-8.47 (m, 2H), 8.72 (br. s., 1H). MS m/z 485 (M+H)$^+$ Example 23: (R)-1-((1-(cyclopropanecarbonyl)pyrrolidin-3-yl)methyl)-2-(2-fluoro-4-(quinolin-7-yl)phenyl)-4,4-dimethyl-1H-imidazol-5(4H)-one (Compound #49)

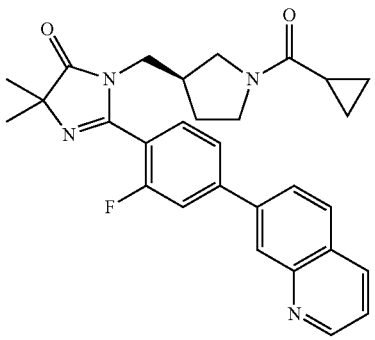

$^1$H NMR (300 MHz, CHLOROFORM-d) δ ppm 0.64-0.78 (m, 2H), 0.85-1.04 (m, 2H), 1.42-1.55 (m, 6H), 1.85 (dd, J=11.4, 4.9 Hz, 0.5H), 1.91-2.10 (m, 1H), 2.32-2.60 (m, 1H), 2.99 (dd, J=12.0, 7.2 Hz, 0.5H), 3.16-3.37 (m, 1H), 3.41-3.58 (m, 3H), 3.58-3.73 (m, 3H), 7.43-7.52 (m, 1H), 7.56-7.68 (m, 1H), 7.68-7.78 (m, 2H), 7.83 (dd, J=8.5, 1.6 Hz, 1H), 7.96 (d, J=8.4 Hz, 1H), 8.23 (d, J=8.2 Hz, 1H), 8.38 (s, 1H), 8.99 (d, J=4.0 Hz, 1H). MS m/z 485 (M+H)$^+$ Example 24: (R)-1-((1-(cyclopropanecarbonyl)pyrrolidin-3-yl)methyl)-2-(2-fluoro-4-(quinolin-3-yl)phenyl)-4,4-dimethyl-1H-imidazol-5(4H)-one (Compound #48)

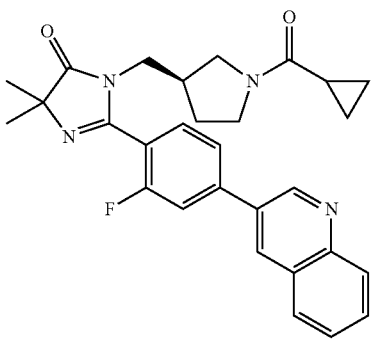 [SMILES: CC1(C)N=C(c2ccc(-c3cnc4ccccc4c3)cc2F)N(C[C@@H]2CCN(C(=O)C3CC3)C2)C1=O]

$^1$H NMR (300 MHz, CHLOROFORM-d) δ ppm 0.59-0.79 (m, 2H), 0.86-1.01 (m, 2H), 1.47 (br. s., 6H), 1.57-1.71 (m, 0.5H), 1.85 (d, J=4.9 Hz, 0.5H), 1.98 (dd, J=11.5, 5.7 Hz, 0.5H), 2.30-2.61 (m, 1H), 2.95 (dd, J=11.9, 7.4 Hz, 0.5H), 3.12-3.37 (m, 1H), 3.38-3.58 (m, 4H), 3.58-3.71 (m, 2H), 7.55-7.67 (m, 2H), 7.67-7.74 (m, 2H), 7.78 (t, J=7.6 Hz, 1H), 7.92 (d, J=8.0 Hz, 1H), 8.16 (d, J=8.4 Hz, 1H), 8.37 (s, 1H), 9.18 (br. s., 1H). MS m/z 485 (M+H)$^+$ Example 25: (R)-1-((1-(cyclopropanecarbonyl)pyrrolidin-3-yl)methyl)-2-(2-fluoro-4-(quinolin-5-yl)phenyl)-4,4-dimethyl-1H-imidazol-5(4H)-one (Compound #47)

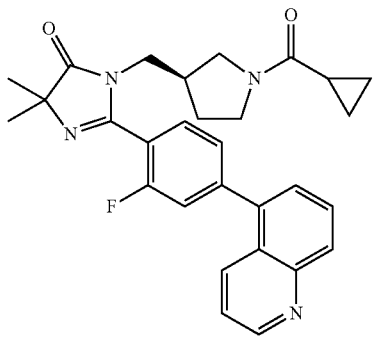 [SMILES: CC1(C)N=C(c2ccc(-c3cccc4ncccc34)cc2F)N(C[C@@H]2CCN(C(=O)C3CC3)C2)C1=O]

$^1$H NMR (300 MHz, CHLOROFORM-d) δ ppm 0.39-0.55 (m, 2H), 0.70 (br. s., 2H), 1.19-1.31 (m, 6H), 1.42-1.51 (m, 0.5H), 1.64 (d, J=6.3 Hz, 0.5H), 1.79 (dd, J=11.7, 5.6 Hz, 0.5H), 2.10-2.25 (m, 0.5H), 2.28-2.42 (m, 0.5H), 2.74 (dd, J=11.9, 7.4 Hz, 0.5H), 2.95-3.16 (m, 1H), 3.18-3.35 (m, 3H), 3.35-3.52 (m, 3H), 7.10-7.13 (m, 1H), 7.16-7.26 (m, 2H), 7.31 (d, J=7.0 Hz, 1H), 7.45 (t, J=7.5 Hz, 1H), 7.56 (t, J=7.8 Hz, 1H), 7.85-8.03 (m, 2H), 8.74 (br. s., 1H). MS m/z 485 (M+H)$^+$ Example 26: (R)-1-((1-(cyclopropanecarbonyl)pyrrolidin-3-yl)methyl)-2-(2-fluoro-4-(1-methyl-1H-indazol-5-yl)phenyl)-4,4-dimethyl-1H-imidazol-5(4H)-one (Compound #53)

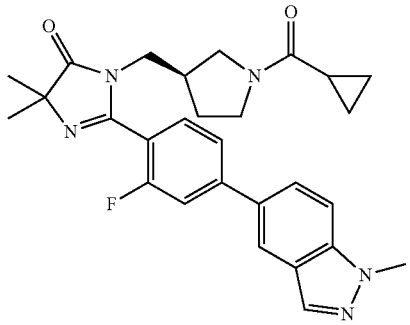

$^1$H NMR (300 MHz, CHLOROFORM-d) δ ppm 0.61-0.80 (m, 2H), 0.85-1.04 (m, 2H), 1.47 (br. s., 6H), 1.58-1.73 (m, 1H), 1.84 (dd, J=10.7, 5.2 Hz, 0.5H), 1.97 (dd, J=11.6, 5.7 Hz, 0.5H), 2.29-2.44 (m, 0.5H), 2.44-2.61 (m, 0.5H), 2.96 (dd, J=12.0, 7.1 Hz, 1H), 3.12-3.40 (m, 1H), 3.40-3.56 (m, 2H), 3.56-3.76 (m, 3H), 4.13 (s, 3H), 7.41-7.57 (m, 2H), 7.57-7.74 (m, 3H), 7.98 (s, 1H), 8.06 (s, 1H). MS m/z 488 (M+H)$^+$ Example 27: (R)-1-((1-(cyclopropanecarbonyl)pyrrolidin-3-yl)methyl)-2-(3-fluoro-4'-(pyridin-4-yl)-[1,1'-biphenyl]-4-yl)-4,4-dimethyl-1H-imidazol-5(4H)-one (Compound #46)

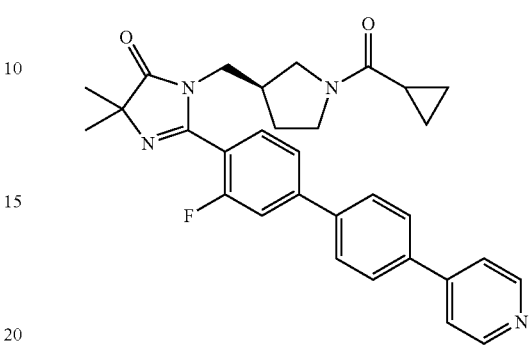

$^1$H NMR (300 MHz, CHLOROFORM-d) δ ppm 0.61-0.81 (m, 2H), 0.94 (br. s., 2H), 1.42-1.56 (m, 6H), 1.64 (dd, J=12.5, 8.0 Hz, 1H), 1.79-1.92 (m, 0.5H), 1.99 (dd, J=11.5, 5.5 Hz, 1H), 2.33-2.45 (m, 0.5H), 2.53 (d, J=7.3 Hz, 0.5H), 2.96 (dd, J=12.0, 7.3 Hz, 0.5H), 3.12-3.38 (m, 1H), 3.41-3.57 (m, 3H), 3.58-3.76 (m, 2H), 7.51 (d, J=5.8 Hz, 1H), 7.55-7.71 (m, 4H), 7.72-7.87 (m, 4H), 8.73 (br. s., 2H). MS m/z 511 (M+H)$^+$ Example 28: (R)-1-((1-(cyclopropanecarbonyl)pyrrolidin-3-yl)methyl)-2-(3-fluoro-4'-(1-methyl-1H-pyrazol-4-yl)-[(1,1'-biphenyl]-4-yl)-4,4-dimethyl-1H-imidazol-5(4H)-one (Compound #45)

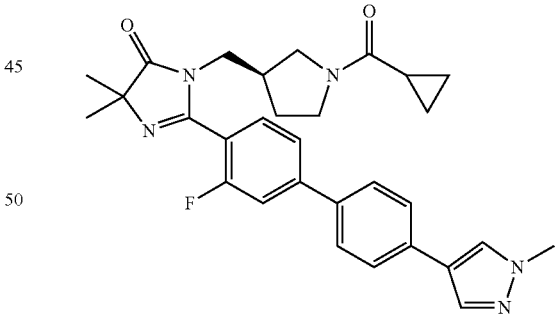

$^1$H NMR (300 MHz, CHLOROFORM-d) δ ppm 0.59-0.82 (m, 2H), 0.93 (br. s., 2H), 1.47 (br. s., 6H), 1.62 (dd, J=12.5, 7.8 Hz, 0.5H), 1.97 (dd, J=11.8, 5.8 Hz, 1H), 2.29-2.44 (m, 0.5H), 2.50 (d, J=7.3 Hz, 0.5H), 2.97 (dd, J=12.0, 7.1 Hz, 0.5H), 3.11-3.39 (m, 1H), 3.39-3.56 (m, 3H), 3.56-3.72 (m, 3H), 3.98 (s, 3H), 7.44 (d, J=5.1 Hz, 1H), 7.53-7.68 (m, 6H), 7.69 (s, 1H), 7.83 (s, 1H), MS m/z 514 (M+H)$^+$ Example 29: (R)-1-((1-(cyclopropanecarbonyl)pyr-rolidin-3-yl)methyl)-2-(2-fluoro-4-(quinazolin-7-yl)phenyl)-4,4-dimethyl-1H-imidazol-5(4H)-one (Compound #44)

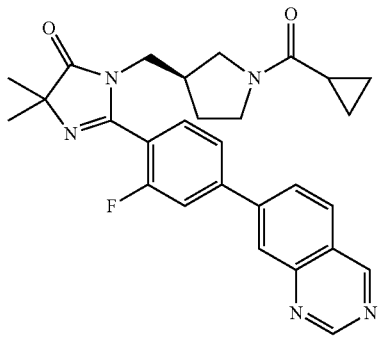 [SMILES: CC1(C)N=C(c2ccc(-c3ccc4cncnc4c3)cc2F)N(C[C@@H]2CCN(C(=O)C3CC3)C2)C1=O]

$^{1}$H NMR (300 MHz, CHLOROFORM-d) δ ppm 0.61-0.80 (m, 2H), 0.85-1.03 (m, 2H), 1.41-1.54 (m, 6H), 1.58-1.74 (m, 0.5H), 1.85 (m, 10.5H), 1.92-2.11 (m, 1H), 2.30-2.44 (m, 0.5H), 2.53 (d, J=7.1 Hz, 0.5H), 2.96 (dd, J=11.9, 7.4 Hz, 0.5H), 3.16-3.38 (m, 1H), 3.40-3.57 (m, 2H), 3.58-3.78 (m, 3H), 7.63 (d, J=5.6 Hz, 1H), 7.66-7.82 (m, 2H), 7.88-8.02 (m, 1H), 8.08 (d, J=8.4 Hz, 1H), 8.29 (s, 1H), 9.39 (s, 1H), 9.47 (s, 1H). MS m/z 486 (M+H)$^{+}$ Example 30: 1-((1-(cyclopropanecarbonyl)azetidin-3-yl)methyl)-2-(2-fluoro-4-(quinazolin-7-yl)phenyl)-4,4-dimethyl-1H-imidazol-5(4H)-one (Compound #43)

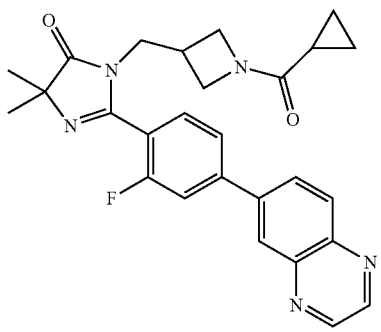 [SMILES: CC1(C)N=C(c2ccc(-c3ccc4nccnc4c3)cc2F)N(CC2CN(C(=O)C3CC3)C2)C1=O]

$^{1}$H NMR (300 MHz, CHLOROFORM-d) δ ppm 0.63-0.77 (m, 2H), 0.90 (quin, J=3.7 Hz, 2H), 1.29-1.31 (m, 1H), 1.46 (s, 6H), 2.71-2.94 (m, 1H), 3.48-3.60 (m, 1H), 3.65-3.78 (m, 1H), 3.78-3.88 (m, 1H), 3.88-4.07 (m, 2H), 4.25 (t, J=8.3 Hz, 1H), 7.53-7.68 (m, 1H), 7.68-7.79 (m, 2H), 7.86-8.00 (m, 1H), 8.10 (d, J=8.4 Hz, 1H), 8.30 (s, 1H), 9.41 (s, 1H), 9.49 (s, 1H). MS m/z 472 (M+H)$^{+}$ Example 31: 1-((1-(cyclopropanecarbonyl)azetidin-3-yl)methyl)-2-(2-fluoro-4-(6-fluoronaphthalen-2-yl)phenyl)-4,4-dimethyl-1H-imidazol-5(4H)-one (Compound #54)

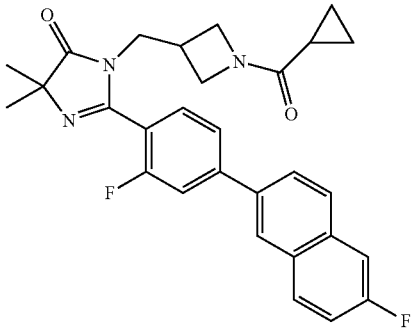 [SMILES: CC1(C)N=C(c2ccc(-c3ccc4cc(F)ccc4c3)cc2F)N(CC2CN(C(=O)C3CC3)C2)C1=O]

$^{1}$H NMR (300 MHz, CHLOROFORM-d) δ ppm 0.63-0.79 (m, 2H), 0.84-0.99 (m, 2H), 1.29-1.31 (m, 1H), 1.47 (s, 6H), 2.83 (d, J=6.7 Hz, 1H), 3.56 (dd, J=10.0, 5.8 Hz, 1H), 3.75 (d, J=6.5 Hz, 1H), 3.80-3.89 (m, 1H), 3.89-4.08 (m, 2H), 4.24 (t, J=8.2 Hz, 1H), 7.33-7.45 (m, 1H), 7.48-7.63 (m, 2H), 7.63-7.74 (m, 2H), 7.78 (d, J=8.4 Hz, 1H), 7.88-8.02 (m, 2H), 8.10 (s, 1H). MS m/z 488 (M+H)$^{+}$ Example 32: 1-((1-(cyclopropanecarbonyl)azetidin-3-yl)methyl)-2-(2-fluoro-4-(8-fluoronaphthalen-2-yl)phenyl)-4,4-dimethyl-1H-imidazol-5(4H)-one (Compound #55)

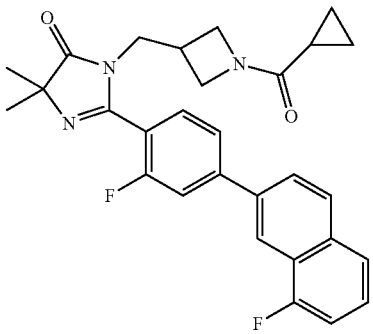 [SMILES: CC1(C)N=C(c2ccc(-c3ccc4cccc(F)c4c3)cc2F)N(CC2CN(C(=O)C3CC3)C2)C1=O]

$^{1}$H NMR (300 MHz, CHLOROFORM-d) δ ppm 0.53-0.68 (m, 2H), 0.75-0.89 (m, 2H), 1.21 (td, J=8.1, 3.9 Hz, 1H), 1.38 (s, 6H), 2.63-2.81 (m, 1H), 3.48 (dd, J=9.7, 5.7 Hz, 1H), 3.58-3.69 (m, 1H), 3.70-3.79 (m, 1H), 3.79-3.93 (m, 2H), 4.15 (t, J=8.3 Hz, 1H), 7.10-7.20 (m, 1H), 7.39 (td, J=7.9, 5.5 Hz, 1H), 7.47-7.67 (m, 4H), 7.67-7.78 (m, 1H), 7.91 (d, J=8.4 Hz, 1H), 8.27 (s, 1H). MS m/z 488 (M+H)$^{+}$ Example 33: 1-((1-(cyclopropanecarbonyl)azetidin-3-yl)methyl)-2-(2-fluoro-4-(isoquinolin-6-yl)phenyl)-4,4-dimethyl-1H-imidazol-5(4H)-one
(Compound #56)

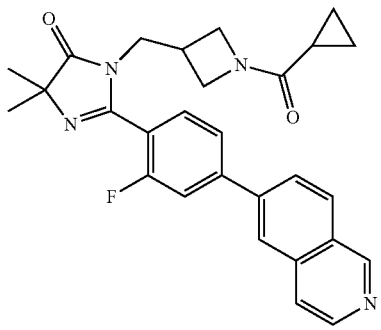 [SMILES: CC1(C)N=C(c2ccc(-c3ccc4cnccc4c3)cc2F)N(CC2CN(C(=O)C3CC3)C2)C1=O]

$^1$H NMR (300 MHz, CHLOROFORM-d) δ ppm 0.70 (dq, J=7.4, 3.4 Hz, 2H), 0.91 (quin, J=3.6 Hz, 2H), 1.20-1.36 (m, 1H), 1.47 (s, 6H), 2.73-2.91 (m, 1H), 3.46-3.61 (m, 1H), 3.64-3.78 (m, 1H), 3.79-3.89 (m, 1H), 3.89-4.04 (m, 2H), 4.25 (t, J=8.3 Hz, 1H), 7.58 (m, 1H), 7.65-7.73 (m, 2H), 7.75 (d, J=5.6 Hz, 1H), 7.83-7.94 (m, 1H), 8.03-8.19 (m, 2H), 8.62 (d, J=5.6 Hz, 1H), 9.34 (s, 1H). MS m/z 471 (M+H)$^+$ Example 34: (R)-1-((1-(cyclopropanecarbonyl)pyrrolidin-3-yl)methyl)-2-(2-fluoro-4-(1H-indazol-3-yl)phenyl)-4,4-dimethyl-1H-imidazol-5(4H)-one
(Compound #57)

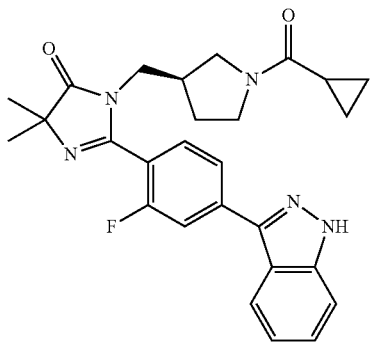 [SMILES: CC1(C)N=C(c2ccc(-c3n[nH]c4ccccc34)cc2F)N(C[C@@H]2CCN(C(=O)C3CC3)C2)C1=O]

$^1$H NMR (300 MHz, CHLOROFORM-d) δ ppm 0.72 (d, J=7.1 Hz, 2H), 0.89-1.09 (m, 2H), 1.41-1.55 (m, 6H), 1.62 (dd, J=12.7, 7.9 Hz, 1H), 1.82 (dd, J=6.0, 3.5 Hz, 0.5H), 1.96 (dd, J=11.8, 5.8 Hz, 1H), 2.43 (td, J=14.8, 7.5 Hz, 1H), 3.03 (dd, J=12.0, 7.0 Hz, 0.5H), 3.20 (t, J=9.1 Hz, 0.5H), 3.32 (dd, J=8.0, 3.5 Hz, 0.5H), 3.43-3.77 (m, 5H), 7.18-7.31 (m, 1H), 7.31-7.44 (m, 1H), 7.50 (d, J=8.2 Hz, 1H), 7.55-7.71 (m, 1H), 7.79-8.07 (m, 3H), 12.22 (br. s., 1H). MS m/z 474 (M+H)$^+$ Example 35: (R)-1-((1-(cyclopropanecarbonyl)pyrrolidin-3-yl)methyl)-2-(2-fluoro-4-(1H-indol-3-yl)phenyl)-4,4-dimethyl-1H-imidazol-5(4H)-one
(Compound #63)

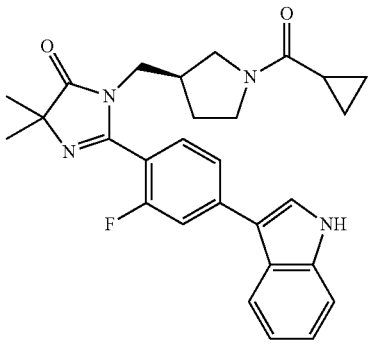 [SMILES: CC1(C)N=C(c2ccc(-c3c[nH]c4ccccc34)cc2F)N(C[C@@H]2CCN(C(=O)C3CC3)C2)C1=O]

$^1$H NMR (300 MHz, CHLOROFORM-d) δ ppm 0.54-0.70 (m, 2H), 0.76-0.97 (m, 2H), 1.37-1.45 (m, 6H), 1.48-1.60 (m, 1H), 1.75 (dd, J=6.2, 4.0 Hz, 0.5H), 1.83-2.00 (m, 1H), 2.36 (td, J=14.4, 7.3 Hz, 1H), 2.91 (dd, J=12.0, 7.2 Hz, 0.5H), 3.05-3.18 (m, 0.5H), 3.18-3.30 (m, 0.5H), 3.35-3.63 (m, 5H), 7.10-7.27 (m, 1H), 7.29-7.58 (m, 5H), 7.85 (d, J=7.4 Hz, 1H), 9.01 (d, J=19.8 Hz, 1H). MS m/z 473 (M+H)$^+$ Example 36: 1-((1-(cyclopropanecarbonyl)azetidin-3-yl)methyl)-2-(2-fluoro-4-(1H-indol-3-yl)phenyl)-4,4-dimethyl-1H-imidazol-5(4H)-one
(Compound #62)

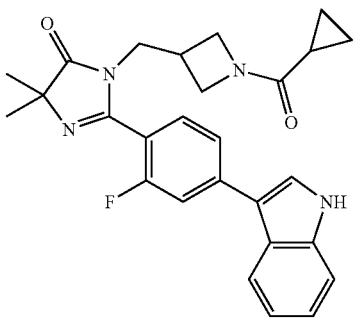 [SMILES: CC1(C)N=C(c2ccc(-c3c[nH]c4ccccc34)cc2F)N(CC2CN(C(=O)C3CC3)C2)C1=O]

$^1$H NMR (300 MHz, CHLOROFORM-d) δ ppm 0.62 (dd, J=7.4, 3.6 Hz, 2H), 0.75-0.90 (m, 2H), 1.18-1.28 (m, 1H), 1.39 (s, 6H), 2.74 (d, J=6.6 Hz, 1H), 3.43-3.54 (m, 1H), 3.59-3.69 (m, 1H), 3.69-3.80 (m, 1H), 3.80-3.95 (m, 2H), 4.16 (t, J=8.3 Hz, 1H), 7.19 (quin, J=7.0 Hz, 1H), 7.30-7.55 (m, 5H), 7.85 (d, J=7.6 Hz, 1H), 9.04 (br. s., 1H). MS m/z 459 (M+H)$^+$ Example 37: 1-((1-(cyclopropanecarbonyl)azetidin-3-yl)methyl)-2-(2-fluoro-4-(1H-indazol-3-yl)phenyl)-4,4-dimethyl-1H-imidazol-5(4H)-one (Compound #58)

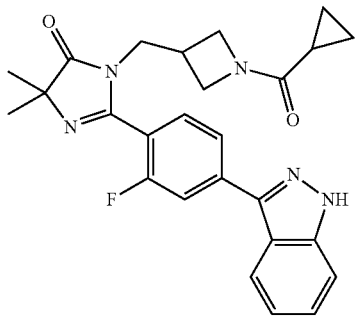 [SMILES: CC1(C)N=C(c2ccc(-c3n[nH]c4ccccc34)cc2F)N(CC2CN(C(=O)C3CC3)C2)C1=O]

$^1$H NMR (300 MHz, CHLOROFORM-d) δ ppm 0.74 (dd, J=7.8, 3.3 Hz, 2H), 0.97 (t, J=3.4 Hz, 2H), 1.29-1.41 (m, 1H), 1.49 (s, 6H), 2.80 (d, J=6.2 Hz, 1H), 3.60 (dd, J=10.0, 5.7 Hz, 1H), 3.72 (d, J=6.0 Hz, 1H), 3.80-3.94 (m, 1H), 3.95-4.10 (m, 2H), 4.26 (t, J=8.3 Hz, 1H), 7.22-7.36 (m, 1H), 7.38-7.50 (m, 1H), 7.51-7.70 (m, 2H), 7.82-8.08 (m, 3H), 11.74 (br. s., 1H). MS m/z 460 (M+H)$^+$ Example 38: (R)-2-(4-(1H-benzo[d]imidazol-2-yl)-2-fluorophenyl)-1-((1-(cyclopropanecarbonyl)pyrrolidin-3-yl)methyl)-4,4-dimethyl-1H-imidazol-5(4H)-one (Compound #61)

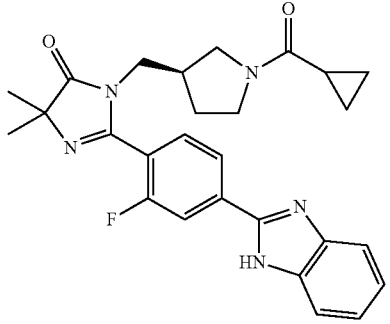 [SMILES: CC1(C)N=C(c2ccc(-c3nc4ccccc4[nH]3)cc2F)N(C[C@@H]2CCN(C(=O)C3CC3)C2)C1=O]

$^1$H NMR (300 MHz, CHLOROFORM-d) δ ppm 0.55-0.76 (m, 2H), 0.76-0.97 (m, 2H), 1.34-1.49 (m, 6H), 1.51-1.61 (m, 1.5H), 1.73 (m, 0.5H), 2.16-2.34 (m, 1H), 2.34-2.51 (m, 1H), 2.88 (dd, J=11.8, 7.3 Hz, 1H), 3.08-3.30 (m, 1H), 3.30-3.68 (m, 4H), 7.12-7.28 (m, 2H), 7.29-7.55 (m, 2H), 7.69 (br. s., 1H), 7.93-8.18 (m, 2H), 12.43 (br. s., 1H). MS m/z 474 (M+H)$^+$ Example 39: 2-(4-(1H-benzo[d]imidazol-2-yl)-2-fluorophenyl)-1-((1-(cyclopropanecarbonyl)azetidin-3-yl)methyl)-4,4-dimethyl-1H-imidazol-5(4H)-one (Compound #60)

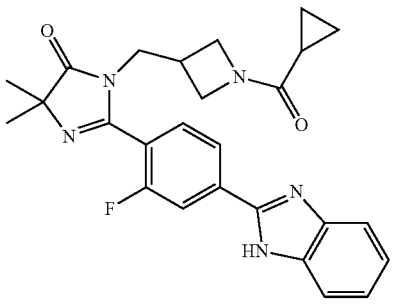 [SMILES: CC1(C)N=C(c2ccc(-c3nc4ccccc4[nH]3)cc2F)N(CC2CN(C(=O)C3CC3)C2)C1=O]

$^1$H NMR (300 MHz, CHLOROFORM-d) δ ppm 0.57-0.74 (m, 2H), 0.74-0.88 (m, 2H), 1.14-1.31 (m, 1H), 1.36 (s, 6H), 2.59-2.76 (m, 1H), 3.31-3.45 (m, 1H), 3.57 (dd, J=14.6, 7.0 Hz, 1H), 3.72 (dd, J=14.5, 7.5 Hz, 1H), 3.79-3.96 (m, 2H), 4.17 (t, J=8.5 Hz, 1H), 7.12-7.26 (m, 2H), 7.43 (t, J=7.6 Hz, 2H), 7.71 (br. s., 1H), 7.89-8.10 (m, 2H), 12.43 (br. s., 1H). MS m/z 460 (M+H)$^+$ Example 40: (R)-1-((1-(cyclopropanecarbonyl)pyrrolidin-3-yl)methyl-2-(2-fluoro-4-(6-fluoronaphthalen-2-yl)phenyl)-4,4-dimethyl-1H-imidazol-5(4H)-one (Compound #66)

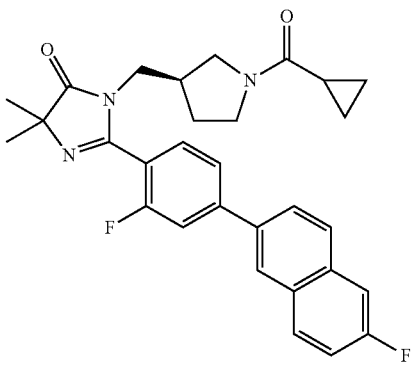 [SMILES: CC1(C)N=C(c2ccc(-c3ccc4cc(F)ccc4c3)cc2F)N(C[C@@H]2CCN(C(=O)C3CC3)C2)C1=O]

$^1$H NMR (300 MHz, CHLOROFORM-d) δ ppm 0.55-0.70 (m, 2H), 0.77-0.93 (m, 2H), 1.31-1.44 (m, 6H), 1.44-1.62 (m, 1.5H), 1.68-1.83 (m, 0.5H), 1.91 (dd, J=11.8, 5.8 Hz, 0.5H), 2.21-2.36 (m, 0.5H), 2.36-2.54 (m, 0.5H), 2.89 (dd, J=12.0, 7.3 Hz, 0.5H), 3.05-3.30 (m, 1H), 3.33-3.67 (m, 5H), 7.21-7.34 (m, 1H), 7.38-7.53 (m, 2H), 7.53-7.63 (m, 2H), 7.63-7.74 (m, 1H), 7.78-7.94 (m, 2H), 8.01 (s, 1H). MS m/z 502 (M+H)$^+$ Example 41: (R)-1-((1-(cyclopropanecarbonyl)pyr-rolidin-3-yl)methyl)-2-(2-fluoro-4-(8-fluoronaphtha-len-2-yl)phenyl)-4,4-dimethyl-1H-imidazol-5(4H)-one (Compound #67)

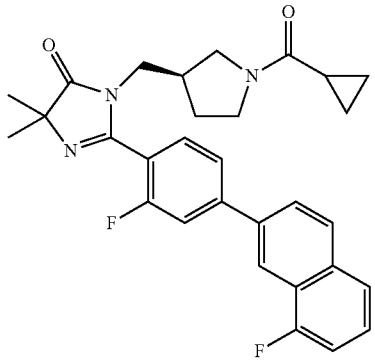 [SMILES: CC1(C)N=C(c2ccc(-c3ccc4cccc(F)c4c3)cc2F)N(C[C@@H]2CCN(C(=O)C3CC3)C2)C1=O]

$^1$H NMR (300 MHz, CHLOROFORM-d) δ ppm 0.50-0.70 (m, 2H), 0.76-0.93 (m, 2H), 1.26-1.47 (m, 7.5H), 1.50-1.65 (m, 0.5H), 1.82-1.98 (m, 0.5H), 2.21-2.37 (m, 0.5H), 2.37-2.52 (m, 0.5H), 2.90 (dd, J=12.0, 7.1 Hz, 0.5H), 3.06-3.29 (m, 1H), 3.32-3.72 (m, 5H), 7.09-7.23 (m, 1H), 7.39 (q, J=6.7 Hz, 1H), 7.54 (d, J=7.0 Hz, 2H), 7.56-7.67 (m, 2H), 7.71 (d, J=8.5 Hz, 1H), 7.91 (d, J=8.7 Hz, 1H), 8.27 (s, 1H). MS m/z 502 (M+H)$^+$ Example 42: (R)-1-((1-(cyclopropanecarbonyl)pyr-rolidin-3-yl)methyl)-2-(2-fluoro-4-(isoquinolin-6-yl)phenyl)-4,4-dimethyl-1H-imidazol-5(4H)-one (Compound #68)

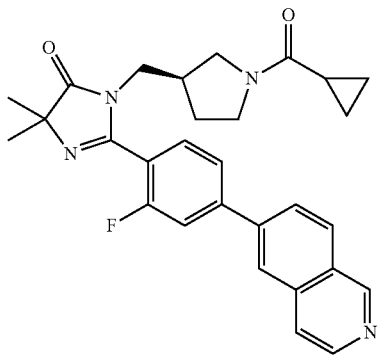 [SMILES: CC1(C)N=C(c2ccc(-c3ccc4cnccc4c3)cc2F)N(C[C@@H]2CCN(C(=O)C3CC3)C2)C1=O]

$^1$H NMR (300 MHz, CHLOROFORM-d) δ ppm 0.56-0.69 (m, 2H), 0.77-0.94 (m, 2H), 1.34-1.46 (m, 7H), 1.49-1.66 (m, 0.5H), 1.69-1.83 (m, 0.5H), 1.90-1.99 (m, 0.5H), 2.21-2.35 (m, 0.5H), 2.36-2.53 (m, 0.5H), 2.87 (dd, J=12.0, 7.4 Hz, 0.5H), 3.06-3.29 (m, 1H), 3.31-3.71 (m, 5H), 7.49 (d, J=5.4 Hz, 1H), 7.57-7.65 (m, 2H), 7.67 (d, J=5.8 Hz, 1H), 7.79 (dd, J=8.6, 1.6 Hz, 1H), 7.99 (s, 1H), 8.04 (d, J=8.5 Hz, 1H), 8.53 (d, J=5.8 Hz, 1H), 9.25 (s, 1H). MS m/z 485 (M+H)$^+$ Example 43: 1-((1-(cyclopropanecarbonyl)azetidin-3-yl)methyl)-2-(2-fluoro-4-(1-methyl-1H-indazol-5-yl)phenyl)-4,4-dimethyl-1H-1-imidazol-5(4H)-one (Compound #69)

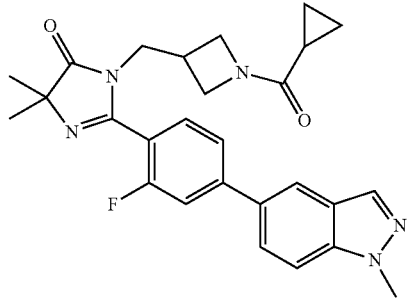 [SMILES: Cn1ncc2cc(-c3ccc(C4=NC(C)(C)C(=O)N4CC4CN(C(=O)C5CC5)C4)c(F)c3)ccc21]

$^1$H NMR (300 MHz, CHLOROFORM-d) δ ppm 0.20-0.35 (m, 2H), 0.74-0.89 (m, 2H), 1.29 (s, 6H), 2.49-2.71 (m, 1H), 3.60 (m, 4H), 3.98 (s, 3H), 3.80-4.20 9 m, 3H), 7.28-7.39 (m, 2H), 7.40-7.48 (m, 2H), 7.48-7.57 (m, 1H), 7.82 (s, 1H), 7.91 (s, 1H). MS m/z 488 (M+H)$^+$ Example 44: 1-((1-(cyclopropanecarbonyl)azetidin-3-yl)methyl)-2-(3-fluoro-4'-(1-methyl-1H-pyrazol-4-yl)-[1,1'-biphenyl]-4-yl)-4,4-dimethyl-1H-imidazol-5(4H)-one (Compound #70)

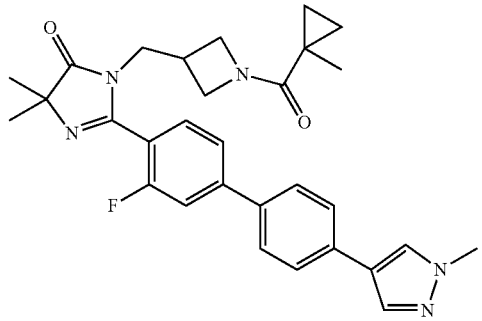

$^1$H NMR (300 MHz, CHLOROFORM-d) δ ppm 0.30-0.41 (m, 2H), 0.84-0.96 (m, 2H), 1.10-1.15 (m, 3H), 1.37 (s, 6H), 2.69 (d, J=7.3 Hz, 1H), 3.33-3.47 (m, 1H), 3.67 (d, J=7.3 Hz, 4H), 3.90 (s, 3H), 3.94-4.25 (m, 2H), 7.36-7.41 (m, 1H), 7.45-7.59 (m, 6H), 7.61 (s, 1H), 7.75 (s, 1H). MS m/z 514 (M+H)$^+$ Example 45: 2-(2-fluoro-4-(6-fluoronaphthalen-2-yl)phenyl)-4,4-dimethyl-1-((1-(1-methylcyclopro-panecarbonyl)azetidin-3-yl)methyl)-1H-imidazol-5(4H)-one (Compound #72)

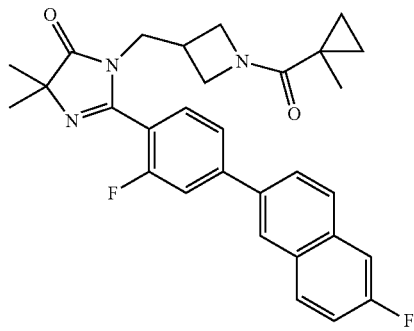 [SMILES: CC1(C(=O)N2CC(CN3C(=O)C(C)(C)N=C3c3ccc(-c4ccc5cc(F)ccc5c4)cc3F)C2)CC1]

¹H NMR (300 MHz, CHLOROFORM-d) δ ppm 0.31-0.40 (m, 2H), 0.86-0.94 (m, 2H), 1.08-1.14 (m, 3H), 1.38 (s, 6H), 2.58-2.79 (m, 1H), 3.35-3.46 (m, 1H), 3.68 (d, J=7.3 Hz, 3H), 3.78-4.17 (m, 3H), 7.26 (td, J=8.7, 2.5 Hz, 1H), 7.38-7.53 (m, 2H), 7.53-7.64 (m, 2H), 7.64-7.74 (m, 1H), 7.79-7.92 (m, 2H), 8.00 (s, 1H). MS m/z 502 (M+H)⁺

Example 46: (R)-2-(2-fluoro-4-(1-methyl-1H-indazol-5-yl)phenyl)-4,4-dimethyl-1-((1-(1-methylcyclopropanecarbonyl)pyrrolidin-3-yl)methyl)-1H-imidazol-5(4H)-one (Compound #73)

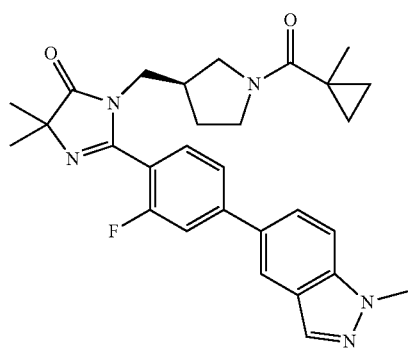

¹H NMR (300 MHz, DMSO-d₆) δ ppm 0.08-0.24 (m, 2H), 0.33-0.57 (m, 2H), 1.11 (s, 6H), 1.18-1.30 (m, 1H), 1.41-1.67 (m, 1H), 1.90-2.11 (m, 1H), 2.65-3.05 (m, 3H), 3.10 (s, 3H), 3.14-3.51 (m, 3H), 7.42-7.52 (m, 1H), 7.52-7.72 (m, 4H), 7.92 (s, 1H), 8.00 (s, 1H). MS m/z 502 (M+H)⁺

Example 47: (R)-2-(3-fluoro-4'-(1-methyl-1H-pyrazol-4-yl)-[1,1'-biphenyl]-4-yl)-4,4-dimethyl-1-((1-(1-methylcyclopropanecarbonyl)pyrrolidin-3-yl)methyl)-1H-imidazol-5(4H)-one (Compound #74)

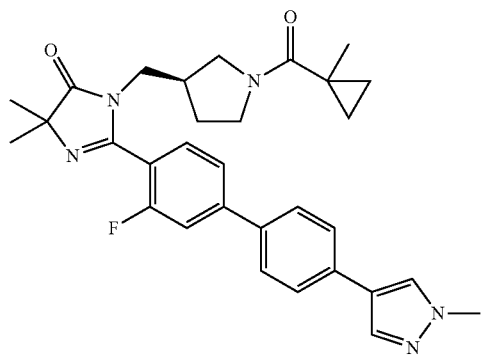

¹H NMR (300 MHz, DMSO-d₆) δ ppm 0.25 (br. s., 2H), 0.40-0.65 (m, 2H), 1.18 (s, 6H), 1.20-1.35 (m, 1H), 1.50-1.72 (m, 1H), 1.92-2.17 (m, 1H), 2.70-3.12 (m, 4H), 3.18 (s, 3H), 3.21-3.26 (m, 3H), 3.26-3.50 (m, 3H), 7.49-7.59 (m, 3H), 7.59-7.72 (m, 4H), 7.81 (s, 1H), 8.10 (s, 1H). MS m/z 528 (M+H)⁺

Example 48: (R)-2-(2-fluoro-4-(6-fluoronaphthalen-2-yl)phenyl)-4,4-dimethyl-1-((1-(1-methylcyclopropanecarbonyl)pyrrolidin-3-yl)methyl)-1H-imidazol-5(4H)-one (Compound #75)

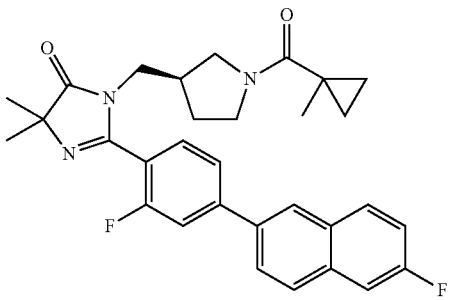 [SMILES: CC1(C(=O)N2CC[C@@H](CN3C(=O)C(C)(C)N=C3c3ccc(-c4ccc5cc(F)ccc5c4)cc3F)C2)CC1]

¹H NMR (300 MHz, DMSO-d₆) δ ppm 0.40 (br. s., 2H), 0.55-0.84 (m, 2H), 1.11 (s, 3H), 1.35 (s, 6H), 1.78 (br. s., 1H), 2.12-2.37 (m, 1H), 2.80-3.35 (m, 4H), 3.57 (br. s., 3H), 7.51 (td, J=8.9, 2.2 Hz, 1H), 7.79 (d, J=8.1 Hz, 2H), 7.86-8.18 (m, 5H), 8.48 (s, 1H). MS m/z 516 (M+H)⁺

Example 49: (R)-2-(2-fluoro-4-(1-methyl-1H-indazol-5-yl)phenyl)-1((1-(1-hydroxycyclopropanecarbonyl)pyrrolidin-3-yl)methyl)-4,4-dimethyl-1H-imidazol-5(4H)-one (Compound #76)

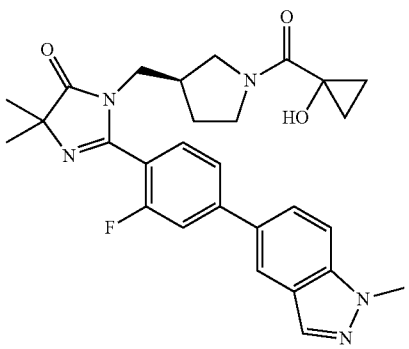

¹H NMR (300 MHz, DMSO-d₆) δ ppm 0.69 (br. s., 2H), 0.75-0.99 (m, 2H), 1.27-1.43 (m, 6H), 1.67-1.92 (m, 1H), 2.19 (br. s., 1H), 3.44-3.82 (m, 7H), 4.10 (s, 3H), 6.00 (s, 1H), 7.62-7.75 (m, 1H), 7.75-7.93 (m, 4H), 8.15 (s, 1H), 8.23 (s, 1H). MS m/z 504 (M+H)⁺

Example 50: (R)-1-((1-(cyclopropanecarbonyl)pyrrolidin-3-yl)methyl)-4,4-dimethyl-2-(4-(quinolin-6-yl)phenyl)-1H-imidazol-5(4H)-one (Compound #64)

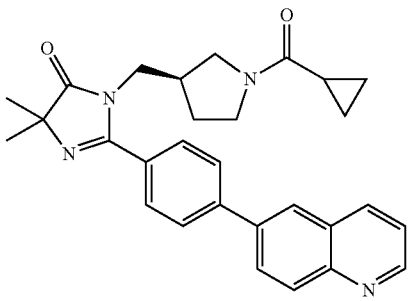 [SMILES: CC1(C)N=C(c2ccc(-c3ccc4ncccc4c3)cc2)N(C[C@@H]2CCN(C(=O)C3CC3)C2)C1=O]

¹H NMR (300 MHz, CHLOROFORM-d) δ ppm 0.64-0.80 (m, 2H), 0.87-1.03 (m, 2H), 1.42-1.51 (m, 1H), 1.51-1.58 (m, 1H), 1.80-1.85 (m, 0.5H), 1.92-2.07 (m, 0.5H), 2.38 (d, J=7.4 Hz, 0.5H), 2.50 (dd, J=8.0, 7.4 Hz, 0.5H), 3.04 (dd, J=12.0, 7.1 Hz, 1H), 3.16-3.39 (m, 1H), 3.44-3.60 (m, 2H), 3.60-3.87 (m, 3H), 7.49 (dd, J=8.2, 4.1 Hz, 1H), 7.75 (dd, J=8.3, 2.4 Hz, 2H), 7.89 (dd, J=8.1, 3.6 Hz, 2H), 7.98-8.07 (m, 1H), 8.09 (d, J=1.8 Hz, 1H), 8.26 (t, J=8.3 Hz, 2H), 8.98 (d, J=4.1 Hz, 1H). MS m/z 467 (M+H)⁺

Example 51: (R)-1-((1-(cyclopropanecarbonyl)pyrrolidin-3-yl)methyl-4,4-dimethyl-2-(4-(quinolin-7-yl)phenyl)-1H-1-imidazol-5(4H)-one (Compound #23)

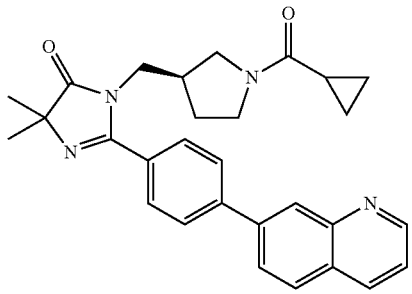 [SMILES: CC1(C)N=C(c2ccc(-c3ccc4cccnc4c3)cc2)N(C[C@@H]2CCN(C(=O)C3CC3)C2)C1=O]

¹H NMR (300 MHz, DMSO-d₆) δ ppm 0.64 (d, J=5.8 Hz, 4H), 1.29-1.37 (m, 6H), 1.40 (br. s., 0.5H), 1.48-1.66 (m, 1H), 1.74 (m., 0.5H), 1.86 (m, 0.5H), 2.22 (d, J=7.4 Hz, 0.5H), 2.32 (m, 0.5H), 2.88 (dd, J=11.8, 6.9 Hz, 0.5H), 3.04-3.19 (m, 1H), 3.23-3.30 (m, 1H), 3.40-3.60 (m, 2H), 3.61-3.75 (m, 2H), 7.58 (dd, J=8.2, 4.3 Hz, 1H), 7.85 (dd, J=8.0, 5.3 Hz, 2H), 8.01-8.11 (m, 3H), 8.11-8.19 (m, 1H), 8.39 (s, 1H), 8.44 (d, J=8.1 Hz, 1H), 8.98 (dd, J=4.1, 1.5 Hz, 1H). MS m/z 467 (M+H)⁺

Example 52: (R)-1-((1-(cyclopropanecarbonyl)pyrrolidin-3-yl)methyl)-4,4-dimethyl-2-(4-(quinolin-5-yl)phenyl)-1H-1-imidazol-5(4H)-one (Compound #31)

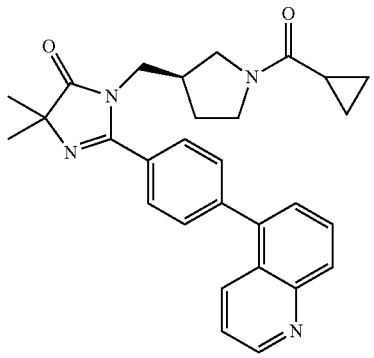 [SMILES: CC1(C)N=C(c2ccc(-c3cccc4ncccc34)cc2)N(C[C@@H]2CCN(C(=O)C3CC3)C2)C1=O]

¹H NMR (300 MHz, DMSO-d₆) δ ppm 0.59-0.76 (m, 4H), 1.30-1.38 (m, 6H), 1.43 (m, 0.5H), 1.51-1.68 (m, 1H), 1.54 (m, 0.5H), 1.89 (m, 0.5H), 2.25 (m, 0.5H), 2.39 (m, 1H), 2.87 (dd, J=11.8, 7.0 Hz, 0.5H), 3.06-3.25 (m, 1H), 3.39 (m, J=7.0 Hz, 1H), 3.42-3.65 (m, 2H), 3.65-3.79 (m, 2H), 7.56 (dd, J=8.4, 4.0 Hz, 1H), 7.60-7.75 (m, 3H), 7.80-7.95 (m, 3H), 8.12 (d, J=8.5 Hz, 1H), 8.23 (t, J=8.9 Hz, 1H), 8.92-9.05 (m, 1H). MS m/z 467 (M+H)⁺

Example 53: 1-((1-(cyclopropanecarbonyl)azetidin-3-yl)methyl)-4,4-dimethyl-2-(4-(quinolin-7-yl)phenyl)-1H-imidazol-5(4H)-one (Compound #24)

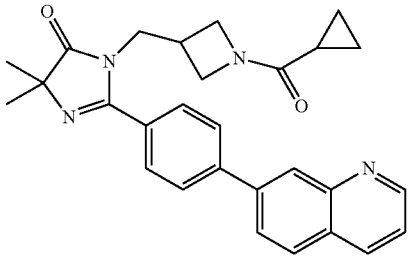 [SMILES: CC1(C)N=C(c2ccc(-c3ccc4cccnc4c3)cc2)N(CC2CN(C(=O)C3CC3)C2)C1=O]

¹H NMR (300 MHz, DMSO-d₆) δ ppm 0.52-0.72 (m, 4H), 1.32 (s, 6H), 1.35-1.45 (m, 1H), 2.64 (d, J=7.8 Hz, 1H), 3.39 (dd, J=9.6, 5.4 Hz, 1H), 3.66-3.81 (m, 2H), 3.88 (d, J=7.4 Hz, 2H), 4.16 (t, J=8.3 Hz, 1H), 7.58 (dd, J=8.2, 4.1 Hz, 1H), 7.84 (d, J=8.2 Hz, 2H), 7.98-8.11 (m, 3H), 8.11-8.19 (m, 1H), 8.39 (s, 1H), 8.44 (d, J=8.1 Hz, 1H), 8.98 (dd, J=4.1, 1.4 Hz, 1H). MS m/z 453 (M+H)⁺

Example 54: 1-((1-(cyclopropanecarbonyl)azetidin-3-yl)methyl)-4,4-dimethyl-2-(4-(quinolin-5-yl)phenyl)-1H-imidazol-5(4H)-one (Compound #18)

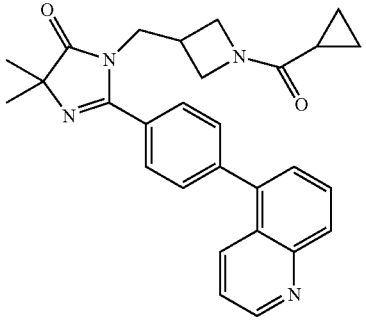 [SMILES: CC1(C)N=C(c2ccc(-c3cccc4ncccc34)cc2)N(CC2CN(C(=O)C3CC3)C2)C1=O]

¹H NMR (300 MHz, DMSO-d₆) δ ppm 0.32-0.47 (m, 4H), 1.09 (s, 6H), 1.13-1.24 (m, 1H), 2.34-2.50 (m, 1H), 3.12-3.18 (m, 1H), 3.43-3.58 (m, 2H), 3.67 (d, J=7.3 Hz, 2H), 3.95 (t, J=8.4 Hz, 1H), 7.32 (dd, J=8.6, 4.1 Hz, 1H), 7.36-7.51 (m, 3H), 7.56-7.72 (m, 3H), 7.88 (d, J=8.4 Hz, 1H), 7.99 (d, J=8.5 Hz, 1H), 8.74 (d, J=2.9 Hz, 1H). MS m/z 453 (M+H)⁺

Example 55: (R)-2-(4-(benzo[d]oxazol-2-yl)phenyl)-1-((1-(cyclopropanecarbonyl)pyrrolidin-3-yl)methyl)-4,4-dimethyl-1H-imidazol-5(4H)-one (Compound #11)

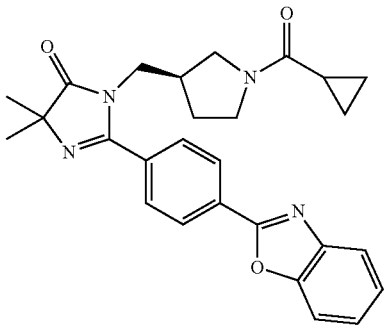 [SMILES: CC1(C)N=C(c2ccc(-c3nc4ccccc4o3)cc2)N(C[C@@H]2CCN(C(=O)C3CC3)C2)C1=O]

¹H NMR (300 MHz, DMSO-d₆) δ ppm 0.55-0.71 (m, 4H), 1.29-1.36 (m, 6H), 1.39 (d, J=7.7 Hz, 0.5H), 1.49-1.64 (m, 1H), 1.74 (m, 0.5H), 1.84 (m, 0.5H), 2.16 (m, 1H), 2.28 (m, 0.5H), 2.84 (dd, J=11.9, 7.1 Hz, 0.5H), 3.04-3.16 (m, 1H), 3.26 (dd, J=11.8, 6.7 Hz, 1H), 3.36-3.60 (m, 2H), 3.65 (t, J=6.4 Hz, 2H), 7.38-7.54 (m, 2H), 7.79-7.90 (m, 2H), 7.94 (dd, J=8.1, 5.2 Hz, 2H), 8.31-8.43 (m, 2H). MS m/z 457 (M+H)⁺

Example 56: 2-(4-(benzo[d]oxazol-2-yl)phenyl)-1-((1-(cyclopropanecarbonyl)azetidin-3-yl)methyl)-4,4-dimethyl-1H-imidazol-5(4H)-one (Compound #12)

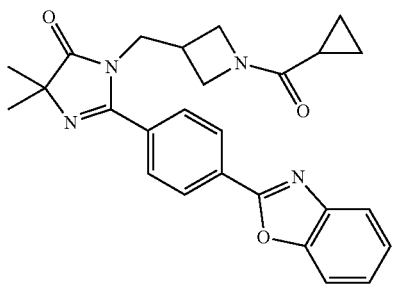 [SMILES: CC1(C)N=C(c2ccc(-c3nc4ccccc4o3)cc2)N(CC2CN(C(=O)C3CC3)C2)C1=O]

¹H NMR (300 MHz, DMSO-d₆) δ ppm 0.56-0.71 (m, 4H), 1.28-1.34 (m, 6H), 1.34-1.45 (m, 1H), 2.56-2.67 (m, 1H), 3.34-3.43 (m, 1H), 3.63-3.81 (m, 2H), 3.86 (d, J=7.6 Hz, 2H), 4.15 (t, J=8.4 Hz, 1H), 7.40-7.55 (m, 2H), 7.80-7.90 (m, 2H), 7.93 (d, J=8.2 Hz, 2H), 8.38 (d, J=8.2 Hz, 2H). MS m/z 443 (M+H)⁺

Example 57: (R)-2-(4-(benzo[d]thiazol-2-yl)phenyl)-1-((1-(cyclopropanecarbonyl)pyrrolidin-3-yl)methyl)-4,4-dimethyl-1H-imidazol-5(4H)-one (Compound #13)

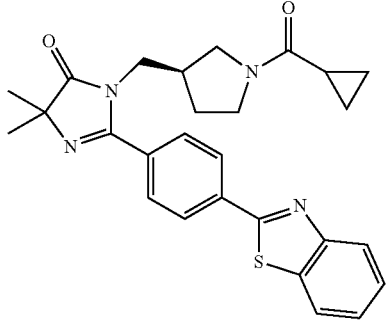 [SMILES: CC1(C)N=C(c2ccc(-c3nc4ccccc4s3)cc2)N(C[C@@H]2CCN(C(=O)C3CC3)C2)C1=O]

¹H NMR (300 MHz, DMSO-d₆) δ ppm 0.64 (d, J=5.5 Hz, 4H), 1.34 (d, J=2.5 Hz, 6H), 1.48-1.65 (m, 1.5H), 1.73 (m, 0.5H), 1.85 (m, 0.5H), 2.15 (m, 0.5H), 2.28 (m, 0.5H), 2.85 (dd, J=11.8, 7.0 Hz, 0.5H), 3.02-3.16 (m, 1H), 3.20-3.29 (m, 1H), 3.36-3.60 (m, 2H), 3.65 (t, J=7.0 Hz, 2H), 7.47-7.57 (m, 1H), 7.57-7.67 (m, 1H), 7.90 (dd, J=8.1, 5.5 Hz, 2H), 8.12 (d, J=7.7 Hz, 1H), 8.21 (d, J=7.7 Hz, 1H), 8.27 (dd, J=8.3, 2.5 Hz, 2H). MS m/z 473 (M+H)⁺

Example 58: 2-(4-(benzo[d]thiazol-2-yl)phenyl)-1-((1-(cyclopropanecarbonyl)azetidin-3-yl)methyl)-4,4-dimethyl-1H-imidazol-5(4H)-one (Compound #14)

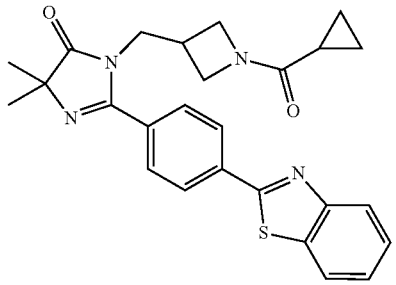 [SMILES: CC1(C)N=C(c2ccc(-c3nc4ccccc4s3)cc2)N(CC2CN(C(=O)C3CC3)C2)C1=O]

¹H NMR (300 MHz, DMSO-d₆) δ ppm 0.54-0.69 (m, 4H), 1.28-1.35 (m, 6H), 1.35-1.44 (m, 1H), 2.54-2.68 (m, 1H), 3.35-3.43 (m, 1H), 3.67-3.81 (m, 2H), 3.86 (d, J=7.4 Hz, 2H), 4.16 (t, J=8.2 Hz, 1H), 7.46-7.56 (m, 1H), 7.56-7.66 (m, 1H), 7.89 (d, J=8.2 Hz, 2H), 8.13 (d, J=8.0 Hz, 1H), 8.22 (d, J=7.6 Hz, 1H), 8.28 (d, J=8.2 Hz, 2H). MS m/z 459 (M+H)⁺

Example 59: (R)-1-((1-(cyclopropanecarbonyl)pyrrolidin-3-1)methyl)-4,4-dimethyl-2-(4'-(pyridin-4-yl)-[1,1'-biphenyl]-4-yl)-1H-imidazol-5(4H)-one (Compound #15)

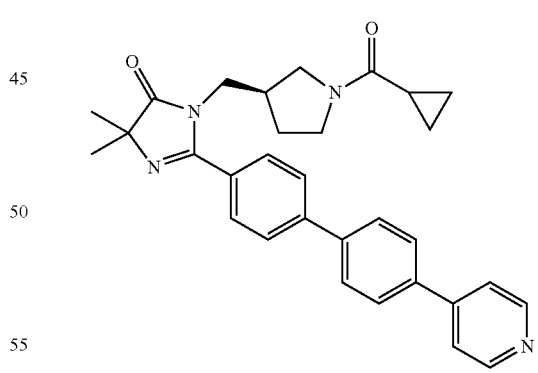

¹H NMR (300 MHz, DMSO-d₆) δ ppm 0.65 (d, J=5.6 Hz, 4H), 1.30-1.37 (m, 6H), 1.49-1.65 (m, 1.5H), 1.74 (m, 0.5H), 1.85 (m, 0.5H), 2.15 (m, 0.5H), 2.29 (m, 0.5H), 2.86 (dd, J=11.8, 7.0 Hz, 0.5H), 3.03-3.18 (m, 1H), 3.28 (d, J=4.7 Hz, 1H), 3.38-3.59 (m, 2H), 3.60-3.74 (m, 2H), 7.74-7.87 (m, 4H), 7.89-8.03 (m, 6H), 8.68 (d, J=5.8 Hz, 2H). MS m/z 493 (M+H)⁺

Example 60: (R)-1-((1-(cyclopropanecarbonyl)pyrrolidin-3-yl)methyl)-4,4-dimethyl-2-(4'-(1-methyl-1H-pyrazol-4-yl)-[1,1'-biphenyl]-4-yl)-1H-imidazol-5(4H)-one (Compound #16)

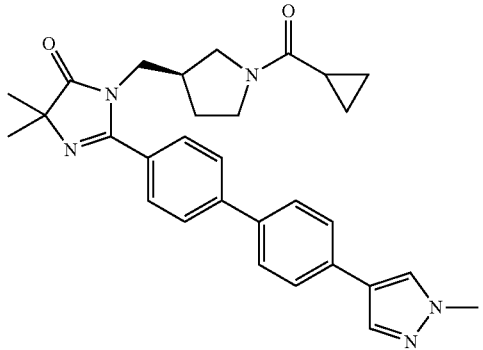

¹H NMR (300 MHz, DMSO-d₆) δ ppm 0.54-0.74 (m, 4H), 1.27-1.36 (m, 6H), 1.48-1.64 (m, 1.5H), 1.71 (m, 0.5H), 1.84 (m, 0.5H), 2.18 (m, 0.5H), 2.30 (m, 0.5H), 2.86 (dd, J=11.7, 6.9 Hz, 0.5H), 3.12 (dd, J=6.9, 3.6 Hz, 1H), 3.19-3.29 (m, 1H), 3.36-3.59 (m, 2H), 3.59-3.74 (m, 2H), 3.89 (s, 3H), 7.63-7.74 (m, 2H), 7.74-7.84 (m, 4H), 7.84-7.92 (m, 2H), 7.95 (s, 1H), 8.23 (s, 1H). MS m/z 496 (M+H)⁺

Example 61: 1-((1-(cyclopropanecarbonyl)azetidin-3-yl)methyl)-4,4-dimethyl-2-(4'-(1-methyl-1H-pyrazol-4-yl)-[1,1'-biphenyl]-4-yl)-1H-imidazol-5(4H)-one (Compound #17)

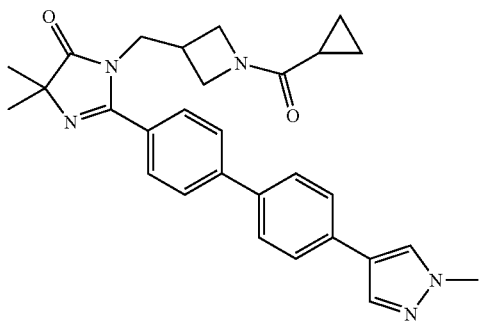

¹H NMR (300 MHz, DMSO-d₆) δ ppm 0.55-0.72 (m, 4H), 1.31 (s, 6H), 1.33-1.43 (m, 1H), 2.60 (m., 1H), 3.34-3.43 (m, 1H), 3.67-3.79 (m, 2H), 3.85 (m, 2H), 3.95 (s, 3H), 4.09-4.23 (m, 1H), 7.64-7.74 (m, 2H), 7.74-7.83 (m, 4H), 7.89 (d, J=8.2 Hz, 2H), 7.95 (s, 1H), 8.23 (s, 1H). MS m/z 482 (M+H)⁺

Example 62: (R)-1-((1-(cyclopropanecarbonyl)pyrrolidin-3-yl)methyl)-4,4-dimethyl-2-(4-(quinolin-3-yl)phenyl)-1H-imidazol-5(4H)-one (Compound #25)

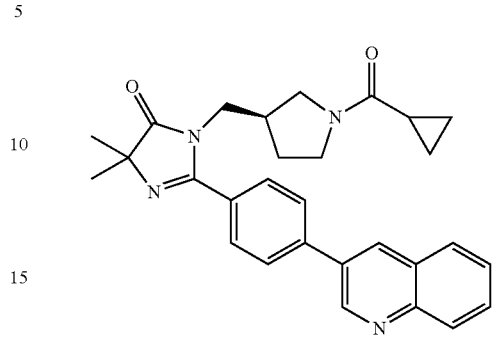

¹H NMR (300 MHz, DMSO-d₆) δ ppm 0.65 (d, J=5.2 Hz, 4H), 1.34 (br. s., 6H), 1.56 (m, 1.5H), 1.74 (m, 0.5H), 1.85 (m, 0.5H), 2.19 (m, 0.5H), 2.31 (m, 0.5H), 2.88 (d, J=7.1 Hz, 0.5H), 3.05-3.18 (m, 1H), 3.26 (m, 1H), 3.40 (s, 3H), 3.46-3.61 (m, 2H), 3.62-3.75 (m, 2H), 7.63-7.75 (m, 1H), 7.76-7.94 (m, 3H), 8.02-8.20 (m, 4H), 8.79 (s, 1H), 9.35 (s, 1H). MS m/z 467 (M+H)⁺

Example 63: 1-((1-(cyclopropanecarbonyl)azetidin-3-yl)methyl)-4,4-dimethyl-2-(4-(quinolin-3-yl)phenyl)-1H-imidazol-5(4H)-one (Compound #19)

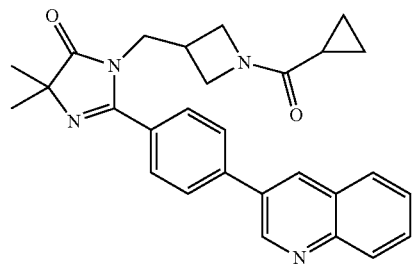 [SMILES: CC1(C)N=C(c2ccc(-c3cnc4ccccc4c3)cc2)N(CC2CN(C(=O)C3CC3)C2)C1=O]

¹H NMR (300 MHz, DMSO-d₆) δ ppm 0.52-0.72 (m, 4H), 1.33 (s, 6H), 1.37-1.45 (m, 1H), 2.57-2.70 (m, 1H), 3.40 (d, J=10.0 Hz, 1H), 3.69-3.82 (m, 2H), 3.88 (d, J=7.6 Hz, 2H), 4.16 (t, J=8.3 Hz, 1H), 7.62-7.75 (m, 1H), 7.77-7.92 (m, 3H), 8.00-8.20 (m, 4H), 8.80 (d, J=2.1 Hz, 1H), 9.35 (d, J=2.2 Hz, 1H). MS m/z 453 (M+H)⁺

Example 64: (R)-1-((1-(cyclopropanecarbonyl)pyrrolidin-3-yl)methyl)-4,4-dimethyl-2-(4-(quinazolin-7-yl)phenyl)-1H-imidazol-5(4H)-one (Compound #42)

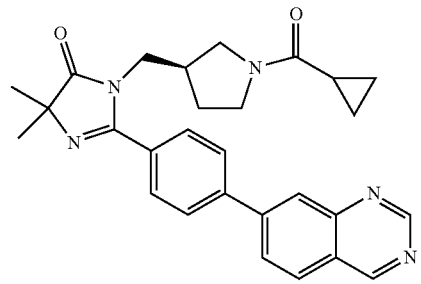 [SMILES: CC1(C)N=C(c2ccc(-c3ccc4cncnc4c3)cc2)N(C[C@@H]2CCN(C(=O)C3CC3)C2)C1=O]

¹H NMR (300 MHz, CHLOROFORM-d) δ ppm 0.47-0.56 (m, 2H), 0.70-0.81 (m, 2H), 1.24-1.29 (m, 6H), 1.29-1.37 (m, 0.5H), 1.64 (m, 0.5H), 1.71-1.85 (m, 0.5H), 2.09-2.25 (m, 0.5H), 2.31 (d, J=8.1 Hz, 0.5H), 2.83 (dd, J=12.0, 7.2 Hz, 0.5H), 3.00-3.17 (m, 1H), 3.23-3.38 (m, 2H), 3.39-3.52 (m, 2H), 3.52-3.63 (m, 2H), 7.58 (dd, J=8.4, 3.2 Hz, 2H), 7.71 (dd, J=8.3, 4.2 Hz, 2H), 7.78 (dd, J=8.5, 1.6 Hz, 1H), 7.88 (d, J=8.5 Hz, 1H), 8.11 (s, 1H), 9.20 (s, 1H), 9.27 (s, 1H). MS m/z 468 (M+H)⁺

Example 65: 1-((1-(cyclopropanecarbonyl)azetidin-3-yl)methyl)-4,4-dimethyl-2-(4-(quinazolin-7-yl)phenyl)-1H-imidazol-5(4H)-one (Compound #36)

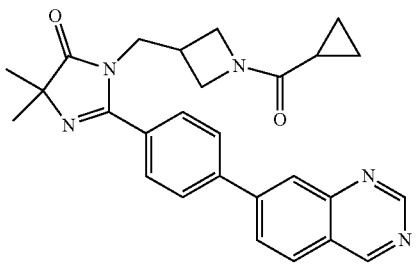 [SMILES: CC1(C)N=C(c2ccc(-c3ccc4cncnc4c3)cc2)N(CC2CN(C(=O)C3CC3)C2)C1=O]

¹H NMR (300 MHz, DMSO-d₆) δ ppm 0.55-0.68 (m, 4H), 1.25-1.36 (m, 6H), 1.36-1.45 (m, 1H), 2.58-2.71 (m, 1H), 3.39 (dd, J=9.8, 5.1 Hz, 1H), 3.67-3.82 (m, 2H), 3.88 (d, J=7.4 Hz, 2H), 4.16 (t, J=8.3 Hz, 1H), 7.86 (d, J=8.2 Hz, 2H), 8.12 (d, J=8.2 Hz, 2H), 8.18-8.26 (m, 1H), 8.32 (d, J=8.5 Hz, 1H), 8.38 (s, 1H), 9.36 (s, 1H), 9.68 (s, 1H), MS m/z 454 (M+H)⁺

Example 66: (R)-1-((1-(cyclopropanecarbonyl)pyrrolidin-3-yl)methyl)-2-(4-(6-fluoronaphthalen-2-yl)phenyl)-4,4-dimethyl-1H-imidazol-6(4H)-one (Compound #30)

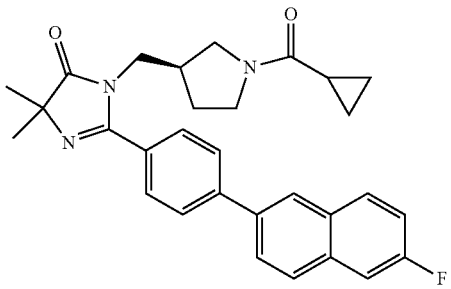 [SMILES: CC1(C)N=C(c2ccc(-c3ccc4cc(F)ccc4c3)cc2)N(C[C@@H]2CCN(C(=O)C3CC3)C2)C1=O]

¹H NMR (300 MHz, DMSO-d₆) δ ppm 0.64 (d, J=5.4 Hz, 4H), 1.28-1.39 (m, 6H), 1.46-1.66 (m, 1.5H), 1.69 (m, 0.5H), 1.79-1.92 (m, 0.5H), 2.13-2.25 (m, 0.5H), 2.25-2.37 (m, 0.5H), 2.86 (dd, J=11.8, 7.0 Hz, 0.5H), 3.05-3.17 (m, 1H), 3.19-3.30 (m, 1H), 3.37-3.60 (m, 2H), 3.60-3.75 (m, 2H), 7.50 (td, J=8.9, 2.5 Hz, 1H), 7.74-7.90 (m, 3H), 7.96-8.09 (m, 4H), 8.14 (dd, J=9.0, 5.8 Hz, 1H), 8.42 (s, 1H). MS m/z 484 (M+H)⁺

Example 67: 1-((1-(cyclopropanecarbonyl)azetidin-3-yl)methyl)-2-(4-(6-fluoronaphthalen-2-yl)phenyl)-4,4-dimethyl-1H-imidazol-5(4H)-one (Compound #29)

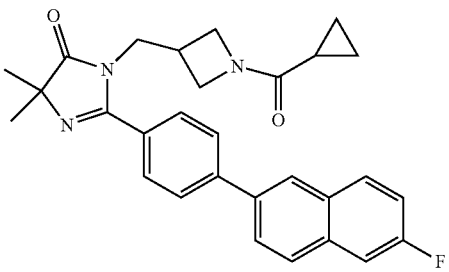 [SMILES: CC1(C)N=C(c2ccc(-c3ccc4cc(F)ccc4c3)cc2)N(CC2CN(C(=O)C3CC3)C2)C1=O]

¹H NMR (300 MHz, DMSO-d₆) δ ppm 0.53-0.69 (m, 4H), 1.32 (s, 6H), 1.35-1.45 (m, 1H), 2.54-2.70 (m, 1H), 3.33-3.45 (m, 1H), 3.67-3.82 (m, 2H), 3.88 (d, J=7.4 Hz, 2H), 4.16 (t, J=8.4 Hz, 1H), 7.44-7.58 (m, 1H), 7.74-7.89 (m, 3H), 7.96-8.03 (m, 2H), 8.03-8.10 (m, 2H), 8.14 (dd, J=9.0, 5.8 Hz, 1H), 8.42 (s, 1H). MS m/z 470 (M+H)⁺

Example 68: 1-((1-(cyclopropanecarbonyl)azetidin-3-yl)methyl)-4,4-dimethyl-2-(4'-(pyridin-4-yl)-[1,1'-biphenyl]-4-yl)-1H-imidazol-5(4H)-one (Compound #26)

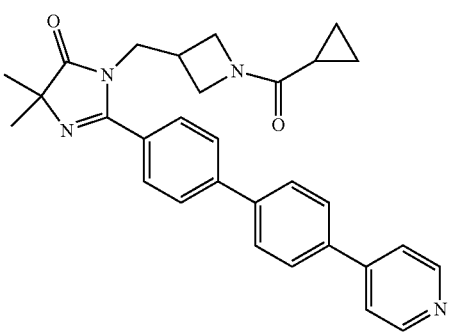 [SMILES: CC1(C)N=C(c2ccc(-c3ccc(-c4ccncc4)cc3)cc2)N(CC2CN(C(=O)C3CC3)C2)C1=O]

¹H NMR (300 MHz, DMSO-d₆) δ ppm 0.57-0.69 (m, 4H), 1.32 (s, 6H), 1.34-1.44 (m, 1H), 2.60 (d, J=5.1 Hz, 1H), 3.33-3.44 (m, 1H), 3.66-3.81 (m, 2H), 3.81-3.88 (m, 2H), 4.16 (t, J=8.3 Hz, 1H), 7.74-7.87 (m, 4H), 7.88-8.03 (m, 6H), 8.68 (d, J=5.8 Hz, 2H). MS m/z 479 (M+H)⁺

Example 69: 1-((1-(cyclopropanecarbonyl)azetidin-3-yl)methyl)-2-(4-(isoquinolin-6-yl)phenyl)-4,4-dimethyl-1H-imidazol-5(4H)-one (Compound #27)

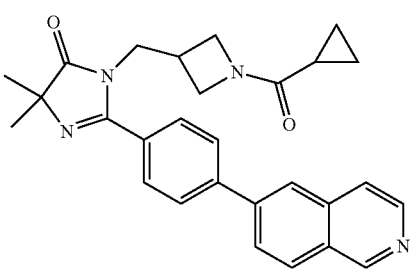 [SMILES: CC1(C)N=C(c2ccc(-c3ccc4cnccc4c3)cc2)N(CC2CN(C(=O)C3CC3)C2)C1=O]

¹H NMR (300 MHz, DMSO-d₆) δ ppm 0.55-0.71 (m, 4H), 1.32 (s, 6H), 1.34-1.45 (m, 1H), 2.62 (d, J=5.5 Hz, 1H), 3.36-3.45 (m, 1H), 3.67-3.82 (m, 2H), 3.88 (d, J=7.4 Hz, 2H), 4.16 (t, J=8.4 Hz, 1H), 7.85 (d, J=8.4 Hz, 2H), 7.93 (d, J=5.8 Hz, 1H), 8.07 (d, J=8.2 Hz, 2H), 8.10-8.18 (m, 1H), 8.27 (d, J=8.7 Hz, 1H), 8.41 (s, 1H), 8.57 (d, J=5.8 Hz, 1H), 9.39 (s, 1H). MS m/z 453 (M+H)⁺

Example 70: (R)-1-((1-(cyclopropanecarbonyl)pyrrolidin-3-yl)methyl-2-(4-(isoquinolin-6-yl)phenyl)-4,4-dimethyl-1H-imidazol-5(4H)-one
(Compound #28)

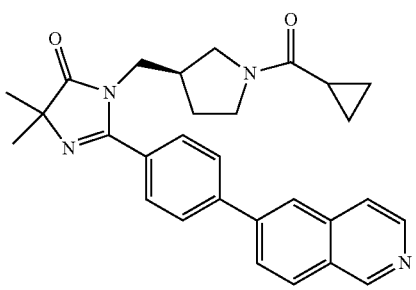 [SMILES: CC1(C)N=C(c2ccc(-c3ccc4cnccc4c3)cc2)N(C[C@@H]2CCN(C(=O)C3CC3)C2)C1=O]

¹H NMR (300 MHz, DMSO-d₆) δ ppm 0.57-0.73 (m, 4H), 1.28-1.39 (m, 6H), 1.44-1.66 (m, 1.5H), 1.72 (m, 0.5H), 1.85 (m, 0.5H), 2.15 (m, 0.5H), 2.29 (d, J=6.9 Hz, 0.5H), 2.86 (dd, J=11.8, 7.1 Hz, 0.5H), 3.03-3.17 (m, 1H), 3.20-3.30 (m, 1H), 3.34-3.60 (m, 2H), 3.60-3.74 (m, 2H), 7.87 (dd, J=8.2, 5.2 Hz, 2H), 7.93 (d, J=5.8 Hz, 1H), 8.00-8.09 (m, 2H), 8.12 (d, J=8.7 Hz, 1H), 8.27 (d, J=8.7 Hz, 1H), 8.40 (s, 1H), 8.57 (d, J=5.8 Hz, 1H), 9.38 (s, 1H). MS m/z 467 (M+H)⁺

Example 71: (R)-2-(4-(1H-indazol-3-yl)phenyl)-1-((1-(cyclopropanecarbonyl)pyrrolidin-3-yl)methyl)-4,4-dimethyl-1H-imidazol-5(4H)-one
(Compound #35)

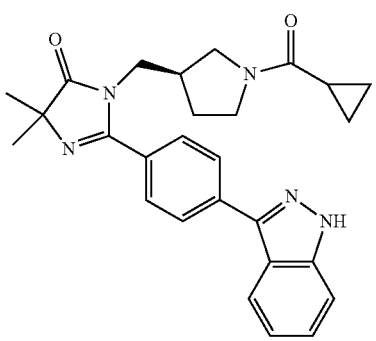 [SMILES: CC1(C)N=C(c2ccc(-c3n[nH]c4ccccc34)cc2)N(C[C@@H]2CCN(C(=O)C3CC3)C2)C1=O]

¹H NMR (300 MHz, DMSO-d₆) δ ppm 0.57-0.70 (m, 4H), 1.28-1.37 (m, 6H), 1.42 (d, J=7.6 Hz, 0.5H), 1.47-1.68 (m, 1.5H), 1.70-1.80 (m, 0.5H), 1.80-1.94 (m, 0.5H), 2.23 (d, J=7.3 Hz, 0.5H), 2.33 (s, 0.5H), 3.04-3.20 (m, 1H), 3.20-3.30 (m, 1H), 3.38-3.61 (m, 2H), 3.68 (t, J=7.1 Hz, 2H), 7.20-7.34 (m, 1H), 7.45 (t, J=7.6 Hz, 1H), 7.64 (d, J=8.4 Hz, 1H), 7.84 (dd, J=8.1, 4.3 Hz, 2H), 8.10-8.28 (m, 3H), 13.42 (s, 1H). MS m/z 456 (M+H)⁺

Example 72: (R)-1-((1-(cyclopropanecarbonyl)pyrrolidin-3-yl)methyl)-2-(4-(8-fluoronaphthalen-2-yl)phenyl)-4,4-dimethyl-1H-imidazol-5(4H)-one
(Compound #41)

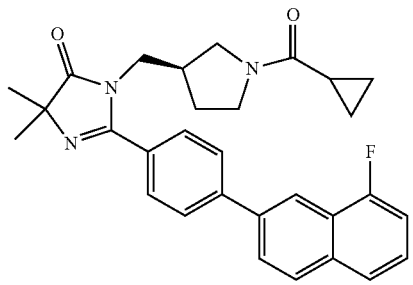 [SMILES: CC1(C)N=C(c2ccc(-c3ccc4cccc(F)c4c3)cc2)N(C[C@@H]2CCN(C(=O)C3CC3)C2)C1=O]

¹H NMR (300 MHz, CHLOROFORM-d) δ ppm 0.63-0.80 (m, 2H), 0.86-1.04 (m, 2H), 1.26 (s, 3H), 1.43 (s, 3H), 1.68-1.75 (m, 0.5H), 1.78-1.90 (m, 0.5H), 1.92-2.11 (m, 1.5H), 2.28-2.43 (m, 0.5H), 2.49 (d, J=15.5 Hz, 0.5H), 3.06 (dd, J=12.1, 7.0 Hz, 0.5H), 3.17-3.40 (m, 1H), 3.46-3.86 (m, 5H), 7.16-7.27 (m, 1H), 7.40-7.54 (m, 1H), 7.64-7.79 (m, 3H), 7.84 (dd, J=8.7, 1.6 Hz, 1H), 7.87-7.94 (m, 2H), 8.00 (d, J=8.5 Hz, 1H), 8.37 (s, 1H). MS m/z 484 (M+H)⁺

Example 73: 1-((1-(cyclopropanecarbonyl)azetidin-3-yl)methyl)-2-(4-(8-fluoronaphthalen-2-yl)phenyl)-4,4-dimethyl-1H-imidazol-5(4H)-one
(Compound #40)

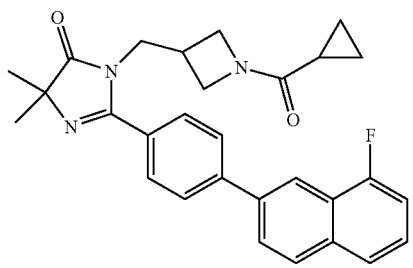 [SMILES: CC1(C)N=C(c2ccc(-c3ccc4cccc(F)c4c3)cc2)N(CC2CN(C(=O)C3CC3)C2)C1=O]

¹H NMR (300 MHz, CHLOROFORM-d) δ ppm 0.71 (dd, J=7.8, 3.3 Hz, 2H), 0.92 (quin, J=3.4 Hz, 2H), 1.24-1.34 (m, 1H), 1.47 (s, 6H), 2.67-2.88 (m, 1H), 3.60 (dd, J=9.8, 5.6 Hz, 1H), 3.86-4.08 (m, 4H), 4.22 (t, J=8.3 Hz, 1H), 7.21 (d, J=7.7 Hz, 1H), 7.44-7.54 (m, 1H), 7.67-7.77 (m, 3H), 7.84 (dd, J=8.5, 1.6 Hz, 1H), 7.91 (d, J=8.2 Hz, 2H), 8.00 (d, J=8.7 Hz, 1H), 8.38 (s, 1H). MS m/z 470 (M+H)⁺

Example 74: (R)-2-(4-(1H-indol-3-yl)phenyl)-1-((1-(cyclopropanecarbonyl)pyrrolidin-3-yl)methyl)-4,4-dimethyl-1H-imidazol-5(4H)-one (Compound #65)

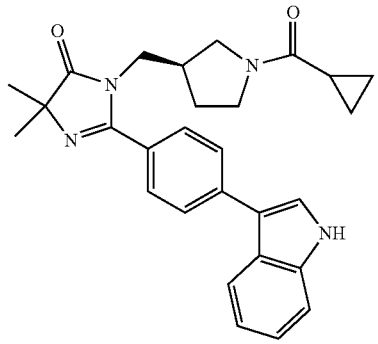 [SMILES: CC1(C)N=C(c2ccc(-c3c[nH]c4ccccc34)cc2)N(C[C@@H]2CCN(C(=O)C3CC3)C2)C1=O]

¹H NMR (300 MHz, CHLOROFORM-d) δ ppm 0.62-0.82 (m, 2H), 0.87-1.06 (m, 2H), 1.17-1.32 (m, 0.5H), 1.48 (br. s., 6H), 1.65 (m, 0.5H), 1.78-1.92 (m, 0.5H), 1.92-2.07 (m, 0.5H), 2.41 (d, J=7.0 Hz, 1H), 3.01-3.15 (m, 1H), 3.18-3.39 (m, 1H), 3.43-3.69 (m, 3H), 3.69-3.90 (m, 2H), 7.20-7.36 (m, 2H), 7.42-7.56 (m, 2H), 7.61-7.75 (m, 2H), 7.77-7.92 (m, 2H), 7.96 (d, J=7.6 Hz, 1H), 8.64 (br. s., 1H). MS m/z 455 (M+H)⁺

Example 76: 2-(4-(1H-indol-3-yl)phenyl)-1-((1-(cyclopropanecarbonyl)azetidin-3-yl)methyl)-4,4-dimethyl-1H-imidazol-5(4H)-one (Compound #59)

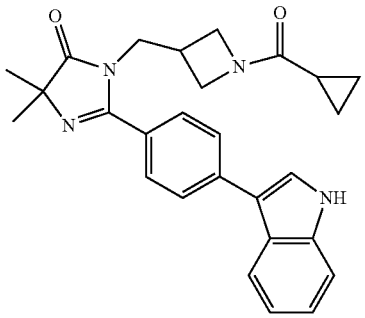 [SMILES: CC1(C)N=C(c2ccc(-c3c[nH]c4ccccc34)cc2)N(CC2CN(C(=O)C3CC3)C2)C1=O]

¹H NMR (300 MHz, CHLOROFORM-d) δ ppm 0.67-0.77 (m, 2H), 0.86-0.97 (m, 2H), 1.47 (s, 6H), 1.70 (d, J=8.4 Hz, 1H), 2.69-2.89 (m, 1H), 3.61 (dd, J=9.8, 5.7 Hz, 1H), 3.83-4.06 (m, 4H), 4.21 (t, J=8.2 Hz, 1H), 7.22-7.36 (m, 2H), 7.42-7.54 (m, 2H), 7.64 (d, J=8.2 Hz, 2H), 7.83 (d, J=8.2 Hz, 2H), 7.96 (d, J=7.7 Hz, 1H), 8.77 (br. s., 1H). MS m/z 441 (M+H)⁺

Example 76: (R)-2-(4-(1H-benzo[d]imidazol-2-yl)phenyl)-1-((1-(cyclopropanecarbonyl)pyrrolidin-3-yl)methyl)-4,4-dimethyl-1H-imidazol-5(4H)-one (Compound #71)

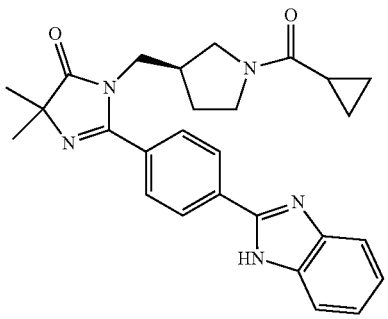 [SMILES: CC1(C)N=C(c2ccc(-c3nc4ccccc4[nH]3)cc2)N(C[C@@H]2CCN(C(=O)C3CC3)C2)C1=O]

¹H NMR (300 MHz, CHLOROFORM-d) δ ppm 0.72-0.81 (m, 2H), 0.93-1.03 (m, 2H), 1.43-1.49 (m, 6H), 1.52-1.57 (m, 0.5H), 1.59-1.72 (m, 0.5H), 1.73-1.86 (m, 0.5H), 1.98 (td, J=12.2, 6.6 Hz, 0.5H), 2.24-2.38 (m, 0.5H), 2.38-2.52 (m, 0.5H), 2.96 (dd, J=12.0, 7.3 Hz, 1H), 3.18-3.36 (m, 1H), 3.40-3.80 (m, 5H), 7.29-7.34 (m, 2H), 7.64 (d, J=8.4 Hz, 2H), 7.69 (d, J=8.2 Hz, 1H), 8.21 (d, J=8.4 Hz, 2H), 8.28 (d, J=8.2 Hz, 1H), 11.53 (br. s., H). MS m/z 465 (M+H)⁺

Example 77: 1-((1-(cyclopropanecarbonyl)azetidin-3-yl)methyl)-4,4-dimethyl-2-(4-(quinolin-6-yl)phenyl)-1H-imidazol-5(4H)-one (Compound #98)

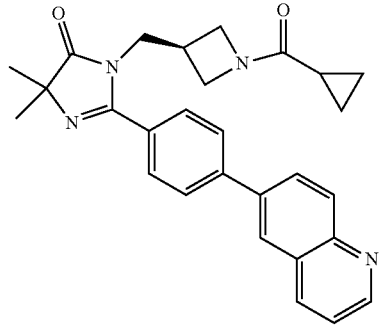

¹H NMR (300 MHz, DMSO-d₆) δ ppm 0.49-0.73 (m, 4H), 1.32 (s, 6H), 1.35-1.45 (m, 1H), 2.55-2.71 (m, 1H), 3.35-3.46 (m, 1H), 3.70-3.82 (m, 2H), 3.89 (s, 1H), 3.87 (s, 1H), 4.16 (t, J=8.3 Hz, 1H), 7.61 (dd, J=8.2, 4.3 Hz, 1H), 7.84 (d, J=8.2 Hz, 2H), 8.06 (d, J=8.2 Hz, 2H), 8.11-8.25 (m, 2H), 8.40-8.45 (m, 1H), 8.48 (d, J=7.8 Hz, 1H), 8.95 (d, J=2.7 Hz, 1H). MS m/z 453 (M+H)⁺

Example 78: 2-(4-(1H-indazol-3-yl)phenyl)-1-((1-(cyclopropanecarbonyl)azetidin-3-yl)methyl)-4,4-dimethyl-1H-imidazol-5(4H)-one (Compound #99)

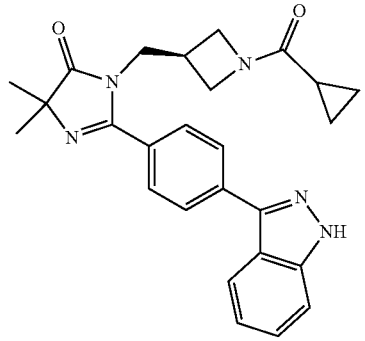

¹H NMR (300 MHz, CHLOROFORM-d) δ ppm 0.71 (dd, J=7.8, 3.2 Hz, 2H), 0.92 (quin, J=3.5 Hz, 2H), 1.24-1.38 (m, 1H), 1.47 (s, 6H), 2.77 (dd, J=7.6, 6.9 Hz, 1H), 3.57-3.68 (m, 1H), 3.85-4.08 (m, 4H), 4.21 (t, J=8.2 Hz, 1H), 7.33 (d, J=7.3 Hz, 2H), 7.49 (t, J=7.6 Hz, 1H), 7.59 (d, J=8.4 Hz, 1H), 7.74 (d, J=8.2 Hz, 2H), 8.07 (d, J=8.2 Hz, 1H), 8.18 (d, J=8.2 Hz, 2H), 10.35 (br. s., 1H). MS m/z 442 (M+H)⁺

Example 79: 2-(2-fluoro-4-(1-methyl-1H-indazol-5-yl)phenyl)-1-((1-(1-hydroxycyclopropanecarbonyl)azetidin-3-yl)methyl)-4,4-dimethyl-1H-imidazol-5(4H)-one (Compound #78)

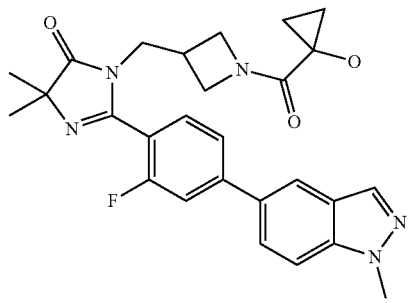 [SMILES: Cn1ncc2cc(-c3ccc(C4=NC(C)(C)C(=O)N4CC4CN(C(=O)C5(O)CC5)C4)c(F)c3)ccc21]

¹H NMR (300 MHz, DMSO-d₆) δ ppm 0.71 (d, J=3.2 Hz, 2H), 0.87-0.99 (m, 2H), 1.32 (s, 6H), 2.51 (br. s., 3H), 2.55-2.68 (m, 1H), 3.35-3.57 (m, 2H), 3.66 (d, J=5.8 Hz, 2H), 3.78 (br. s., 1H), 4.01 (br. s., 1H), 4.36 (br. s., 1H), 5.90 (s, 1H), 7.54-7.75 (m, 1H), 7.75-7.95 (m, 4H), 8.15 (s, 1H), 8.23 (s, 1H)

Example 80: 2-(2-fluoro-4-(6-fluoronaphthalen-2-yl)phenyl)-1-((1-(1-hydroxycyclopropanecarbonyl)azetidin-3-yl)methyl)-4,4-dimethyl-1H-imidazol-5(4H)-one (Compound #79)

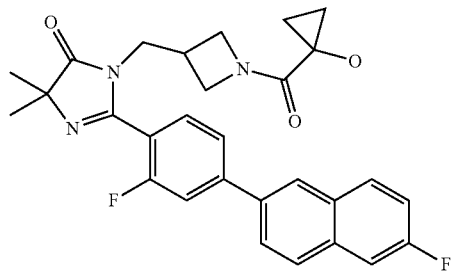 [SMILES: CC1(C)N=C(c2ccc(-c3ccc4cc(F)ccc4c3)cc2F)N(CC2CN(C(=O)C3(O)CC3)C2)C1=O]

¹H NMR (300 MHz, DMSO-d₆) δ ppm 0.58-0.76 (m, 2H), 0.89-1.00 (m, 2H), 1.33 (s, 6H), 2.53-2.69 (m, 1H), 3.38 (br. s., 1H), 3.38-3.51 (m, 1H), 3.67 (d, J=5.4 Hz, 2H), 3.78 (t, J=7.6 Hz, 1H), 4.02 (br. s., 1H), 4.36 (t, J=8.1 Hz, 1H), 5.90 (s, 1H), 7.44-7.58 (m, 1H), 7.71-7.85 (m, 2H), 7.87-7.99 (m, 2H), 7.99-8.08 (m, 2H), 8.08-8.18 (m, 1H), 8.49 (s, 1H)

Example 81: (R)-4,4-dimethyl-2-(2-methyl-4-(1-methyl-1H-indazol-5-yl)phenyl)-1-((1-(1-methylcyclopropanecarbonyl)pyrrolidin-3-yl)methyl)-1H-imidazol-5(4H)-one (Compound #80)

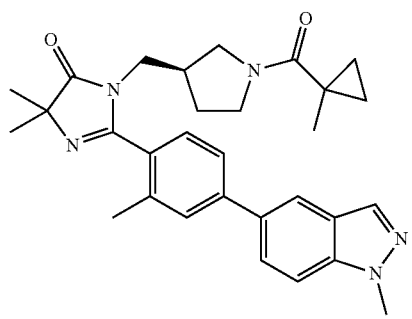 [SMILES: Cc1cc(-c2ccc3c(cnn3C)c2)ccc1C1=NC(C)(C)C(=O)N1C[C@@H]1CCN(C(=O)C2(C)CC2)C1]

¹H NMR (300 MHz, DMSO-d₆) δ ppm 0.15 (br. s., 2H), 0.32-0.56 (m, 2H), 0.86 (s, 3H), 1.09 (s, 6H), 1.13 (m, 2H), 1.52 (br. s., 1H), 1.95 (br. s., 1H), 2.13 (s, 3H), 2.26 (br. s., 1H), 2.69 (br. s., 1H), 2.83-3.06 (m, 2H), 3.15 (br. s, 1H), 3.84 (s, 3H), 7.27 (d, J=7.7 Hz, 1H), 7.38-7.62 (m, 4H), 7.88 (s, 2H)

Example 82: 2-(3-fluoro-4'-(1-methyl-1H-pyrazol-4-yl)-[1,1'-biphenyl]-4-yl)-1-((1-(1-hydroxycyclopropanecarbonyl)azetidin-3-yl)methyl)-4,4-dimethyl-1H-imidazol-5(4H)-one (Compound #81)

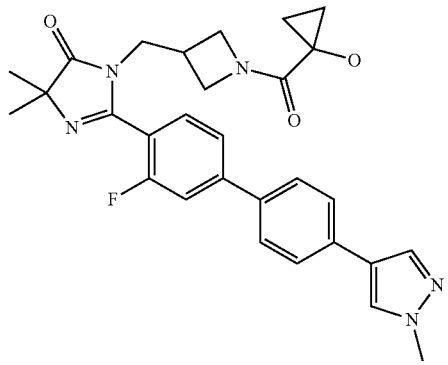 [SMILES: Cn1cc(-c2ccc(-c3ccc(C4=NC(C)(C)C(=O)N4CC4CN(C(=O)C5(O)CC5)C4)c(F)c3)cc2)cn1]

¹H NMR (300 MHz, CHLOROFORM-d) δ ppm 0.85 (d, J=2.9 Hz, 2H), 1.17 (s, 2H), 1.37 (s, 6H), 1.40-1.62 (m, 1H), 1.90-1.98 (m, 3H), 2.51 (br. s., 1H), 2.60-2.71 (m, 1H), 3.30-3.50 (m, 1H), 3.62-3.79 (m, 2H), 3.85-3.93 (m, 1H), 3.94-4.17 (m, 1H), 5.36 (br. s., 1H), 7.39 (d, J=11.4 Hz, 1H), 7.45-7.58 (m, 6H), 7.61 (s, 1H), 7.75 (s, 1H)

Example 83: 2-(4-(6-fluoronaphthalen-2-yl)-2-methylphenyl)-4,4-dimethyl-1-((1-1-methylcyclopropanecarbonyl)azetidin-3-yl)methyl)-1H-imidazol-5(4H)-one (Compound #82)

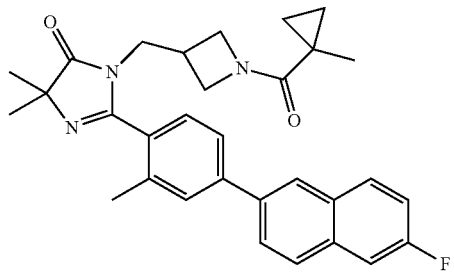 [SMILES: Cc1cc(-c2ccc3cc(F)ccc3c2)ccc1C1=NC(C)(C)C(=O)N1CC1CN(C(=O)C2(C)CC2)C1]

¹H NMR (300 MHz, DMSO-d₆) δ ppm 0.26-0.45 (m, 2H), 0.76 (br. s., 2H), 1.09 (s, 3H), 1.12 (br. s., 1H), 1.34 (s, 6H), 1.91 (br. s., 1H), 2.39 (s, 3H), 3.35-3.47 (m, 1H), 3.51-3.64 (m, 2H), 3.91 (br. s., 1H), 4.10 (br. s., 1H), 7.49 (td, J=8.9, 2.4 Hz, 1H), 7.59 (d, J=8.0 Hz, 1H), 7.69-7.87 (m, 2H), 7.89 (s, 1H), 7.98 (d, J=8.8 Hz, 1H), 8.05 (d, J=8.7 Hz, 1H), 8.13 (dd, J=8.9, 5.9 Hz, 1H), 8.39 (s, 1H)

Example 84: 4,4-dimethyl-2-(2-methyl-4-(1-methyl-1H-benzo[d]imidazol-5-yl)phenyl)-1-((1-(1-methylcyclopropanecarbonyl)azetidin-3-yl)methyl)-1H-imidazol-5(4H)-one (Compound #83)

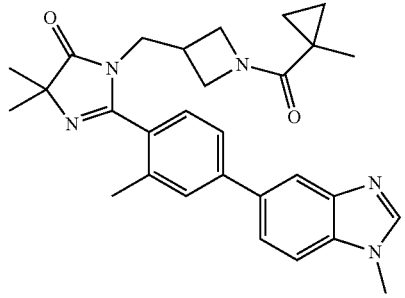 [SMILES: Cc1cc(-c2ccc3c(c2)ncn3C)ccc1C1=NC(C)(C)C(=O)N1CC1CN(C(=O)C2(C)CC2)C1]

¹H NMR (300 MHz, DMSO-d₆) δ ppm 0.37 (br. s., 2H), 0.77 (br. s., 2H), 1.09 (s, 3H), 1.24 (br. s., 1H), 1.33 (s, 6H), 2.37 (s, 3H), 2.51 (br. s., 2H), 3.39-3.45 (m, 1H), 3.58 (br. s., 3H), 3.89 (br. s, 2H), 4.12 (br. s., 1H), 7.52 (d, J=8.0 Hz, 1H), 7.64-7.77 (m, 3H), 7.79 (s, 1H), 8.02 (s, 1H), 8.25 (s, 1H)

Example 85: (R)-4,4-dimethyl-2-(3-methyl-4'-(1-methyl-1H-pyrazol-4-yl)-[1,1'-biphenyl]-4-yl)-1-((1-(1-methylcyclopropanecarbonyl)pyrrolidin-3-yl) methyl)-1H-imidazol-5(4H)-one (Compound #84)

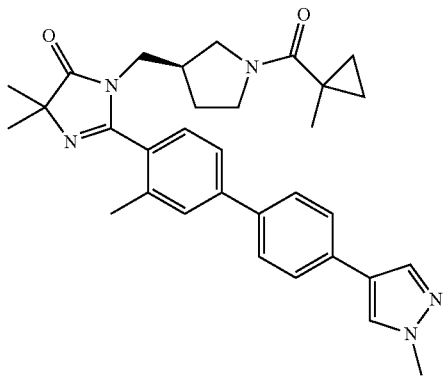 [SMILES: Cc1cc(-c2ccc(-c3cnn(C)c3)cc2)ccc1C1=NC(C)(C)C(=O)N1C[C@@H]1CCN(C(=O)C2(C)CC2)C1]

¹H NMR (300 MHz, CHLOROFORM-d) δ ppm 0.30-0.48 (m, 2H), 0.73-0.83 (m, 2H), 1.14 (s, 3H), 1.39 (s, 6H), 1.78 (br. s., 1H), 2.01 (br. s., 1H), 2.28 (br. s., 1H), 2.32 (s, 3H), 2.97 (br. s., 1H), 3.16-3.54 (m, 5H), 3.88 (s, 3H), 7.30 (d, J=8.4 Hz, 1H), 7.44-7.58 (m, 6H), 7.59 (s, 1H), 7.73 (s, 1H)

Example 86: (R)-4,4-dimethyl-2-(2-methyl-4-(1-methyl-1H-benzo[d]imidazol-5-yl)phenyl)-1-((1-(1-methylcyclopropanecarbonyl)pyrrolidin-3-yl) methyl)-1H-imidazol-5(4H)-one (Compound #85)

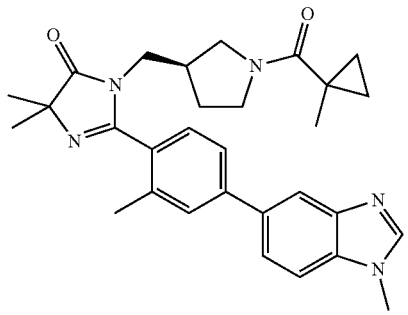 [SMILES: Cc1cc(-c2ccc3c(c2)ncn3C)ccc1C1=NC(C)(C)C(=O)N1C[C@@H]1CCN(C(=O)C2(C)CC2)C1]

¹H NMR (300 MHz, DMSO-d₆) δ ppm 0.40 (br. s., 2H), 0.58-0.82 (m, 2H), 1.11 (br. s., 3H), 1.24 (br. s., 1H), 1.34 (s, 6H), 1.77 (br. s., 1H), 2.21 (br. s., 1H), 2.38 (s, 3H), 2.51 (br. s., 2H), 2.97 (br. s., 1H), 3.09-3.30 (m, 2H), 3.39-3.49 (m, 1H), 3.89 (s, 3H), 7.51 (d, J=7.7 Hz, 1H), 7.64-7.75 (m, 4H), 7.78 (s, 1H), 8.02 (s, 1H), 8.25 (s, 1H)

Example 87: (R)-2-(4-(6-fluoronaphthalen-2-yl)-2-methylphenyl)-4,4-dimethyl-1-((1-(1-methylcyclopropanecarbonyl)pyrrolidin-3-yl)methyl)-1H-imidazol-5(4H)-one (Compound #86)

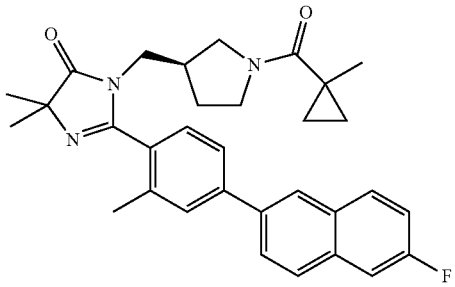 [SMILES: Cc1cc(-c2ccc3cc(F)ccc3c2)ccc1C1=NC(C)(C)C(=O)N1C[C@@H]1CCN(C(=O)C2(C)CC2)C1]

¹H NMR (300 MHz, DMSO-d₆) δ ppm 0.15 (br. s., 2H), 0.35-0.60 (m, 2H), 0.83 (br. s., 1H), 0.86 (br. s., 3H), 0.93-1.04 (m, 1H), 1.10 (s, 6H), 1.22 (br. s., 1H), 1.52 (br. s., 1H), 1.94 (br. s., 1H), 2.16 (s, 3H), 2.55-2.80 (m, 1H), 2.84-3.02 (m, 2H), 3.17-3.38 (m, 1H), 7.15-7.29 (m, 1H), 7.34 (d, J=7.0 Hz, 1H), 7.46-7.61 (m, 2H), 7.64 (br. s., 1H), 7.69-7.84 (m, 2H), 7.88 (d, J=14.2 Hz, 1H), 8.14 (br. s., 1H)

Example 88: 4,4-dimethyl-2-(3-methyl-4'-(1-methyl-1H-pyrazol-4-yl)-[1,1'-biphenyl]-4-yl)-1-((1-(1-methylcyclopropanecarbonyl)azetidin-3-yl) methyl)-1H-imidazol-5(4H)-one (Compound #87)

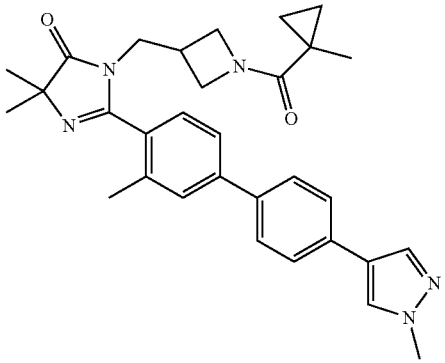 [SMILES: Cc1cc(-c2ccc(-c3cnn(C)c3)cc2)ccc1C1=NC(C)(C)C(=O)N1CC1CN(C(=O)C2(C)CC2)C1]

¹H NMR (300 MHz, DMSO-d₆) δ ppm 0.38 (br. s., 2H), 0.77 (br. s., 2H), 1.09 (br. s., 3H), 1.12 (br. s., 1H), 1.33 (br. s., 6H), 1.54 (br. s., 1H), 2.36 (br. s., 2H), 2.51 (br. s., 3H), 3.39 (m, 1H), 3.57 (br. s., 1H), 3.70-4.02 (m, 3H), 4.12 (br. s., 1H), 7.53 (d, J=7.8 Hz, 1H), 7.61-7.84 (m, 6H), 7.94 (s, 1H), 8.22 (s, 1H)

Example 89: 4,4-dimethyl-2-(2-methyl-4-(1-methyl-1H-1-indazol-5-yl)phenyl)-1-((1-(1-methylcyclopropanecarbonyl)azetidin-3-yl)methyl)-1H-imidazol-5 (4H)-one (Compound #77)

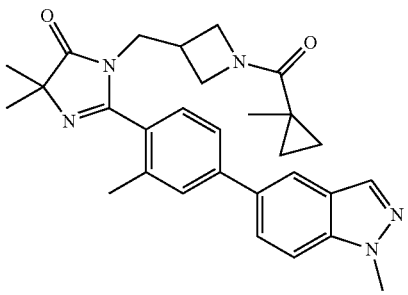 [SMILES: Cc1cc(-c2ccc3c(cnn3C)c2)ccc1C1=NC(C)(C)C(=O)N1CC1CN(C(=O)C2(C)CC2)C1]

¹H NMR (300 MHz, DMSO-d₆) δ ppm 0.37 (br. s., 2H), 0.77 (br. s., 2H), 1.09 (br. s., 3H), 1.33 (br. s., 6H), 2.37 (br. s., 3H), 2.51 (br. s., 2H), 3.34 (br. s., 4H), 3.58 (br. s., 2H), 4.10 (br. s., 2H), 7.53 (d, J=7.6 Hz, 1H), 7.66-7.89 (m, 4H), 8.13 (br. s., 2H). MS m/z 484 (M+H)⁺

Example 90: (R)-2-(2-fluoro-4-(6-fluoronaphthalen-2-yl)phenyl)-1-((1-(1-hydroxycyclopropanecarbonyl)pyrrolidin-3-yl)methyl)-4,4-dimethyl-1H-imidazol-5(4H)-one (Compound #88)

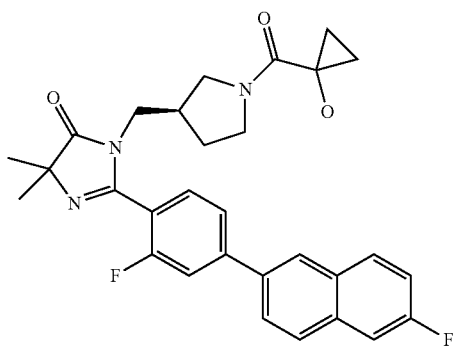 [SMILES: CC1(C)N=C(c2ccc(-c3ccc4cc(F)ccc4c3)cc2F)N(C[C@@H]2CCN(C(=O)C3(O)CC3)C2)C1=O]

¹H NMR (300 MHz, CHLOROFORM-d) δ ppm 0.78 (br. s., 2H), 1.06 (d, J=6.0 Hz, 2H), 1.39 (s, 6H), 1.74 (br. s., 2H), 2.29 (dt, J=14.3, 7.2 Hz, 1H), 2.93 (br. s., 1H), 3.39 (br. s., 1H), 3.48 (br. s., 3H), 3.72 (br. s., 2H), 7.26 (td, J=8.7, 2.2 Hz, 1H), 7.37-7.52 (m, 2H), 7.52-7.61 (m, 2H), 7.68 (d, J=8.4 Hz, 1H), 7.78-7.90 (m, 2H), 8.00 (s, 1H). MS m/z 518 (M+H)⁺

Example 91: (R)-2-(2-fluoro-4-(1-methyl-1H-benzo[d]imidazol-5-yl)phenyl)-1-((1-(1-hydroxycyclopropanecarbonyl)pyrrolidin-3-yl)methyl)-4,4-dimethyl-1H-imidazol-5(4H)-one (Compound #89)

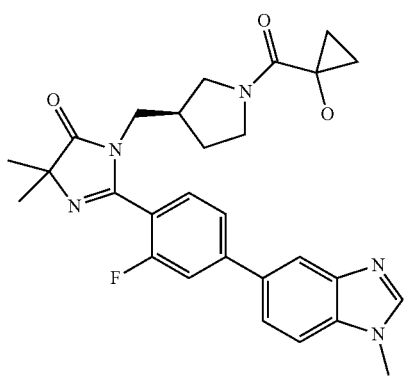 [SMILES: Cn1cnc2cc(-c3ccc(C4=NC(C)(C)C(=O)N4C[C@@H]4CCN(C(=O)C5(O)CC5)C4)c(F)c3)ccc21]

¹H NMR (300 MHz, CHLOROFORM-d) δ ppm 0.78 (br. s., 2H), 0.87-1.09 (m, 2H), 1.38 (br. s., 6H), 1.77 (br. s., 1H), 1.93 (br. s., 1H), 2.17-2.41 (m, 1H), 2.94 (br. s., 0.5H), 3.27 (br. s., 1.5H), 3.46 (br. s., 4H), 3.82 (s, 3H), 4.61 (br. s., 1H), 7.34-7.45 (m, 2H), 7.52 (br. s., 3H), 7.87 (br. s., 1H), 7.95 (br. s., 1H). MS m/z 504 (M+H)⁺

Example 92: (R)-2-(2-fluoro-4-(1-methyl-1H-benzo[d]imidazol-5-yl)phenyl)-4,4-dimethyl-1-((1-(1-methylcyclopropanecarbonyl)pyrrolidin-3-yl)methyl)-1H-imidazol-5(4H)-one (Compound #90)

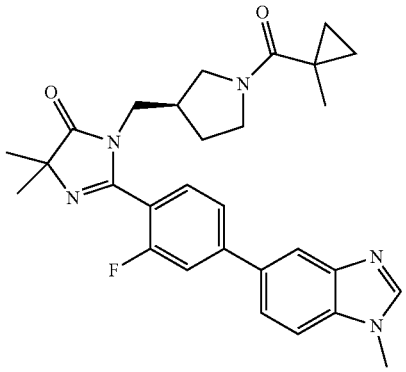 [SMILES: Cn1cnc2cc(-c3ccc(C4=NC(C)(C)C(=O)N4C[C@@H]4CCN(C(=O)C5(C)CC5)C4)c(F)c3)ccc21]

¹H NMR (300 MHz, CHLOROFORM-d) δ ppm 0.27 (br. s., 2H), 0.51-0.65 (m, 1H), 0.69 (br. s., 1H), 1.00 (br. s., 3H), 1.25 (s, 6H), 1.70 (br. s., 2H), 2.19 (br. s., 1H), 2.85 (br. s., 1H), 3.29 (d, J=7.0 Hz, 5H), 3.69 (s, 3H), 7.28 (d, J=8.8 Hz, 2H), 7.33-7.45 (m, 3H), 7.73 (s, 1H), 7.83 (s, 1H). MS m/z 502 (M+H)⁺

Example 93: 1-((1-(1-hydroxycyclopropanecarbonyl)azetidin-3-yl)methyl)-4,4-dimethyl-2-(2-methyl-4-(1-methyl-1H-benzo[d]imidazol-5-yl)phenyl)-1H-imidazol-5(4H)-one (Compound #91)

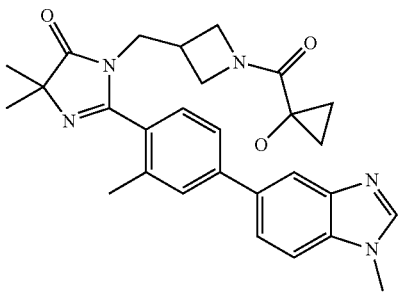 [SMILES: Cc1cc(-c2ccc3c(c2)ncn3C)ccc1C1=NC(C)(C)C(=O)N1CC1CN(C(=O)C2(O)CC2)C1]

¹H NMR (300 MHz, CHLOROFORM-d) δ ppm 0.70-0.86 (m, 2H), 1.11 (br. s., 2H), 1.34 (s, 6H), 2.21-2.34 (m, 3H), 2.44-2.66 (m, 1H), 3.53 (d, J=7.3 Hz, 3H), 3.82 (s, 3H), 3.87 (br. s., 1H), 3.97 (br. s., 1H), 4.35 (br. s., 1H), 4.64 (br. s., 1H), 7.26 (d, J=7.7 Hz, 1H), 7.35-7.43 (m, 1H), 7.45-7.55 (m, 3H), 7.84 (s, 1H), 7.92 (s, 1H). MS m/z 486 (M+H)⁺

Example 94: (R)-1-((1-(1-hydroxycyclopropanecarbonyl)pyrrolidin-3-yl)methyl)-4,4-dimethyl-2-(2-methyl-4-(1-methyl-1H-benzo[d]imidazol-5-yl)phenyl)-1H-imidazol-5(4H)-one (Compound #92)

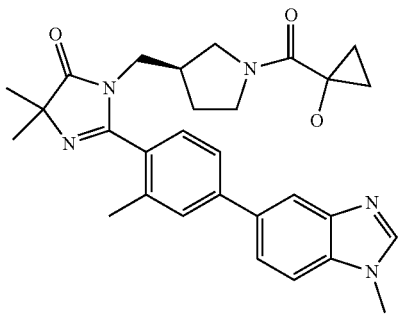 [SMILES: Cc1cc(-c2ccc3c(c2)ncn3C)ccc1C1=NC(C)(C)C(=O)N1C[C@@H]1CCN(C(=O)C2(O)CC2)C1]

¹H NMR (300 MHz, CHLOROFORM-d) δ ppm 0.77 (br. s., 3H), 0.88-0.98 (m, 1H), 1.38 (s, 6H), 1.74 (br. s., 1H), 2.20-2.25 (m 1H), 2.30 (s, 3H), 2.92 (br. s., 1H), 3.15-3.45 (m, 5H), 3.49-3.74 (m, 2H), 3.81 (s, 3H), 7.29 (d, J=7.7 Hz, 1H), 7.40 (d, J=7.7 Hz, 1H), 7.45-7.60 (m, 3H), 7.87 (br. s., 1H), 7.94 (br. s., 1H). MS m/z 500 (M+H)⁺

Example 95: 2-(2-fluoro-4-(1-methyl-1H-benzo[d]imidazol-5-yl)phenyl)-4,4-dimethyl-1-((1-(1-methylcyclopropanecarbonyl)azetidin-3-yl)methyl)-1H-imidazol-5(4H)-one (Compound #93)

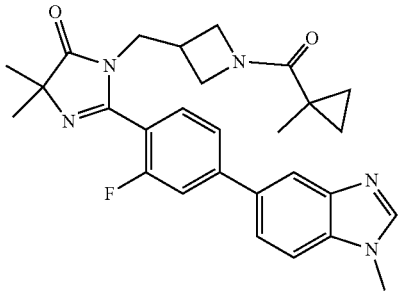 [SMILES: Cn1cnc2cc(-c3ccc(C4=NC(C)(C)C(=O)N4CC4CN(C(=O)C5(C)CC5)C4)c(F)c3)ccc21]

¹H NMR (300 MHz, CHLOROFORM-d) δ ppm 0.20 (br. s., 2H), 0.74 (br. s., 2H), 0.95 (br. s., 3H), 1.22 (br. s., 6H), 1.58 (br. s., 1H), 2.53 (br. s., 1H), 3.25 (br. s., 1H), 3.45-3.57 (m, 2H), 3.68 (br. s., 3H), 3.89 (br. s., 2H), 7.26 (br. s., 2H), 7.38 (br. s., 3H), 7.72 (br. s., 1H), 7.82 (br. s., 1H). MS m/z 488 (M+H)⁺

Example 96: 2-(2-fluoro-4-(1-methyl-1H-benzo[d]imidazol-5-yl)phenyl)-1-((1-(1-hydroxycyclopropanecarbonyl)azetidin-3-yl)methyl)-4,4-dimethyl-1H-imidazol-5(4H)-one (Compound #94)

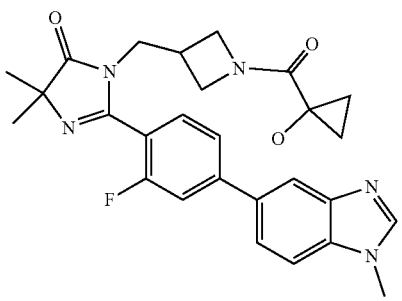 [SMILES: Cn1cnc2cc(-c3ccc(C4=NC(C)(C)C(=O)N4CC4CN(C(=O)C5(O)CC5)C4)c(F)c3)ccc21]

¹H NMR (300 MHz, CHLOROFORM-d) δ ppm 0.74-0.85 (m, 2H), 1.12 (br. s., 2H), 1.35 (s, 6H), 2.56-2.75 (m, 1H), 3.49 (br. s., 1H), 3.55-3.77 (m, 3H), 3.83 (s, 3H), 4.01 (br. s., 2H), 4.37 (br. s., 1H), 7.35-7.45 (m, 2H), 7.47-7.58 (m, 3H), 7.88 (s, 1H), 7.93 (s, 1H). MS m/z 490 (M+H)⁺

Example 97: (R)-2-(3-fluoro-4'-(1-methyl-1H-pyrazol-4-yl)-[1,1'-biphenyl]-4-yl)-1-((1-(1-hydroxycyclopropanecarbonyl)pyrrolidin-3-yl)methyl)-4,4-dimethyl-1H-imidazol-6(4H)-one (Compound #95)

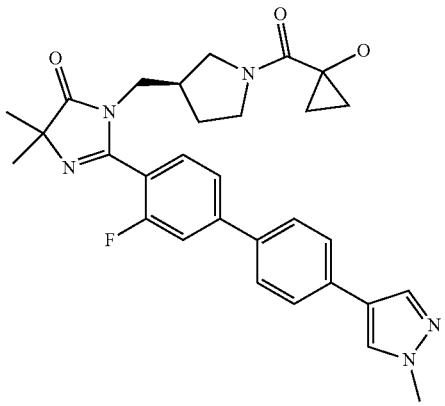 [SMILES: Cn1cc(-c2ccc(-c3ccc(C4=NC(C)(C)C(=O)N4C[C@@H]4CCN(C(=O)C5(O)CC5)C4)c(F)c3)cc2)cn1]

¹H NMR (300 MHz, CHLOROFORM-d) δ ppm 0.78 (br. s., 2H), 0.90-1.01 (m, 1H), 1.04 (br. s., 1H), 1.38 (s, 6H), 1.80 (br. s., 2H), 2.28 (dt, J=14.3, 7.2 Hz, 1H), 2.93 (br. s., 0.5H), 3.27 (br. s., 1.5H), 3.42-3.60 (m, 3H), 3.74 (br. s., 2H), 3.89 (s, 3H), 7.37 (d, J=11.3 Hz, 1H), 7.44-7.57 (m, 6H), 7.60 (s, 1H), 7.74 (s, 1H). MS m/z 530 (M+H)⁺

Example 98: 6-(4-(1-((1-(cyclopropanecarbonyl)azetidin-3-yl)methyl)-4,4-dimethyl-5-oxo-4,5-dihydro-1H-imidazol-2-yl)-3-methylphenyl)-2-naphthonitrile (Compound #96)

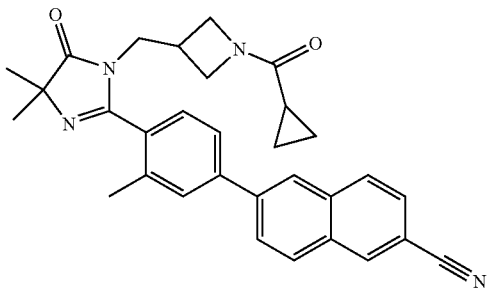 [SMILES: Cc1cc(-c2ccc3cc(C#N)ccc3c2)ccc1C1=NC(C)(C)C(=O)N1CC1CN(C(=O)C2CC2)C1]

¹H NMR (300 MHz, CHLOROFORM-d) δ ppm 0.45 (br. s., 2H), 0.66 (br. s., 2H), 1.23 (br. s., 6H), 2.21 (br. s., 3H), 2.47 (br. s., 1H), 3.26 (br. s., 3H), 3.43-3.57 (m, 1H), 3.66 (br. s., 2H), 3.97 (br. s., 1H), 7.12-7.30 (m, 1H), 7.46 (br. s., 3H), 7.66 (br. s., 1H), 7.76 (br. s., 2H), 7.88 (br. s., 1H), 8.04 (br. s., 1H). MS m/z 491 (M+H)⁺

Example 99: 6-(4-(1-((1-(cyclopropanecarbonyl)azetidin-3-yl)methyl)-4,4-dimethyl-5-oxo-4,5-dihydro-1H-imidazol-2-yl)-3-fluorophenyl)-2-naphthonitrile (Compound #97)

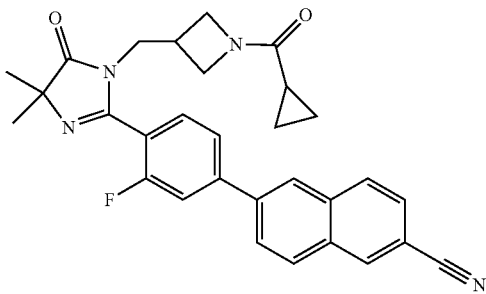 [SMILES: CC1(C)N=C(c2ccc(-c3ccc4cc(C#N)ccc4c3)cc2F)N(CC2CN(C(=O)C3CC3)C2)C1=O]

$^1$H NMR (300 MHz, CHLOROFORM-d) δ ppm 0.72 (br. s., 2H), 0.92 (br. s., 2H), 1.48 (br. s., 6H), 2.03 (br. s., 1H), 2.83 (br. s., 1H), 3.55 (br. s., 1H), 3.65-3.80 (m, 1H), 3.85 (d, J=8.0 Hz, 1H), 3.96 (d, J=7.4 Hz, 2H), 4.26 (br. s., 1H), 7.61 (d, J=10.6 Hz, 1H), 7.70 (br. s., 3H), 7.90 (br. s., 1H), 7.98-8.11 (m, 2H), 8.15 (br. s., 1H), 8.31 (br. s., 1H). MS m/z 495 (M+H)$^+$ Biological Example 1

Fatty Acid Synthase (FASN) Inhibition Scintillation Proximity Assay

In this assay, inhibition of FASN activity is measured using $^3$H-acetyl-CoA and malonyl-CoA as substrates. $^3$H-Acetyl CoA is converted to $^3$H-palmitate through a series of reactions by the FASN protein, which contains 7 functional domains and carries out 7 enzymatic reactions to ultimately produce $^3$H-palmitate. The assay principle is based upon the fact that $^3$H-acetyl-CoA is hydrophilic and the end product, $^3$H-palmitate is hydrophobic. The hydrophobic $^3$H-palmitate binds to scintillation proximity assay (SPA) imaging beads (resulting in light emission from the imaging beads) whereas the hydrophilic $^3$H-acetyl-CoA does not bind to the imaging beads (and therefore does not result in light emission from the imaging beads).

10 μL assay buffer (100 mM KH$_2$PO$_4$ pH 7.5, 1 mM DTT) (20 μL in blanks) was added to a 384-well white OptiPlate plate (Perkin Elmer). 0.9 μL test compound (at concentrations of 30 μM, 10 μM, 3 μM, 1 μM, 0.30 μM, 0.10 μM, 0.03 μM and 0.01 μM)/DMSO and 10 μL hFASN enzyme (full length, 300 ng, purified in house) or 10 μL assay buffer was added to the wells. Then 10 μL 450 μM NADPH (Sigma N7505), 18.75 μM [$^3$H]-acetyl-CoA (Perkin Elmer NET-290L), 150 μM malonyl-CoA (Sigma M4263) were added, mixed and incubated at room temperature for 60 minutes. The reaction was stopped by adding 20 μL Streptavidin coupled imaging beads (25 mg/ml). After incubation for 30 minutes at room temperature in the dark, the 384 well plate was centrifuged at 1500 rpm for 3 minutes and was measured after at least 24 hrs by the LEADseeker™, measuring emission using a 610±20 nm pass filter. (Bays, N. W., et al., "A simplified scintillation proximity assay for fatty acid synthase activity: development and comparison with other FAS activity assays", *J. Biomol. Screen.*, 2009, pp 636-642, Vol. 14(6).)

Raw data generated by the instrument were normalized to % Controlmin values, which were calculated as:

$$\% \text{ Control}_{min} = 100*(x-\text{mLC})/(\text{mHC}-\text{mLC})$$

where mLC and mHC were the means of the low control wells and high control wells on the plate, after manual exclusion of outliers. A plot of Control$_{min}$ versus test compound concentration was fitted to a 4-parameter logistic curve using a non-linear least squares regression method. From the plot, an IC$_{50}$ (concentration at which 50% inhibition is achieved) was calculated. pIC$_{50}$ values were calculated as −log(IC$_{50}$), when IC$_{50}$ is expressed in molar units.

Representative compounds of formula (I) the present invention were tested according to the procedure as described in Biological Example 1 above, with results as listed in Table BIO-1, below. Where a compound was tested more than once, the pIC$_{50}$ value listed below represents the mean of the measurements. Wherein the results listed below, the pIC$_{50}$ value is preceded with a "~", the "~" indicates that the standard error of the pIC$_{50}$ value, as estimated by the non-linear regression algorithm, is larger than 0.5. This corresponds to a factor of uncertainly on the pIC$_{50}$ that is larger than square root of 10 (>3.162).

TABLE BIO-1

| Human FASN pIC$_{50}$ | |
|---|---|
| Compound No. | pIC$_{50}$ |
| 1 | 7.32 |
| 2 | 6.85 |
| 3 | 7.09 |
| 4 | 6.92 |
| 5 | 6.81 |
| 6 | 6.79 |
| 7 | 7.14 |
| 8 | 6.62 |
| 9 | 6.48 |
| 10 | 6.31 |
| 11 | 6.20 |
| 12 | ~5.37 |
| 13 | 6.20 |
| 14 | 5.74 |
| 15 | 7.40 |
| 16 | 6.99 |
| 17 | 6.26 |
| 18 | ~5.25 |
| 19 | 5.38 |
| 20 | 5.70 |
| 21 | 5.87 |
| 22 | 6.80 |
| 23 | 7.25 |
| 24 | 6.69 |
| 25 | 6.15 |
| 26 | ~6.22 |
| 27 | 6.72 |
| 28 | 7.23 |
| 29 | 7.02 |
| 30 | 7.26 |
| 31 | 6.72 |
| 32 | 6.29 |
| 33 | 6.74 |
| 34 | 6.38 |
| 35 | ~5.19 |
| 36 | 5.43 |
| 37 | 5.86 |
| 38 | 5.05 |
| 39 | 7.05 |
| 40 | 6.75 |
| 41 | 7.34 |
| 42 | 6.65 |
| 43 | 6.11 |
| 44 | 6.79 |
| 45 | 7.20 |
| 46 | 7.28 |

TABLE BIO-1-continued

Human FASN pIC$_{50}$

| Compound No. | pIC$_{50}$ |
|---|---|
| 47 | 6.78 |
| 48 | 6.64 |
| 49 | 7.34 |
| 50 | 6.94 |
| 51 | 6.72 |
| 52 | 6.25 |
| 53 | 7.03 |
| 54 | 7.55 |
| 55 | 7.46 |
| 56 | 7.17 |
| 57 | 6.48 |
| 58 | 6.00 |
| 59 | ~5.79 |
| 60 | 5.32 |
| 61 | 6.10 |
| 62 | 6.69 |
| 63 | 7.16 |
| 64 | 5.67 |
| 65 | 6.64 |
| 66 | 7.48 |
| 67 | 7.37 |
| 68 | 7.26 |
| 69 | 6.96 |
| 70 | 7.18 |
| 71 | 5.23 |
| 72 | 7.45 |
| 73 | 7.18 |
| 74 | 7.26 |
| 75 | 7.26 |
| 76 | 7.07 |
| 77 | 6.82 |
| 78 | 6.61 |
| 79 | 7.52 |
| 80 | 7.20 |
| 81 | 6.28 |
| 82 | 7.47 |
| 83 | 6.99 |
| 84 | 7.27 |
| 85 | 7.10 |
| 86 | 7.37 |
| 87 | 7.12 |
| 88 | 7.69 |
| 89 | 7.22 |
| 90 | 7.10 |
| 91 | 6.37 |
| 92 | 7.04 |
| 93 | 7.00 |
| 94 | 6.49 |
| 95 | 7.52 |
| 96 | 7.39 |
| 97 | NT$^a$ |
| 98 | <5 |
| 99 | 5.26 |

$^a$The notation "NT" indicates that the listed compound was not tested.

Biological Example 2

Fatty Acid Synthase Keto-Reductase Domain (FASN KR) Inhibition

10 µL assay buffer (100 mM KH$_2$PO$_4$ pH 7.5) was added to a 384-well clear plate (costar 3702), 0.3 µL compound (at concentrations of 30 µM, 10 µM, 3 µM, 1 µM, 0.30 µM, 0.10 µM, 0.03 µM and 0.01 µM)/DMSO, 10 µL hFASN enzyme (full length, 300 ng, purified in house) and 360 µM NADPH (except in blank) were then added. Then, 10 µL 180 mM ethyl acetoacetate (Aldrich 688983) was added, mixed and immediately thereafter, the absorbance at 340 nm (T1) by Multiscan (Labsystems) was measured. After 20 minutes incubation at room temperature the plate was measured again (T2).

Enzymatic activity of FASN KR was measured as the oxidation of NADPH to NADP$^+$ (a decrease in NADPH signal was observed at OD 340 nm). The decrease in absorbance was calculated as (Absorbance before incubation T1)−(Absorbance following incubation T2).

Raw data generated by the instrument were normalized to % Controlmin values, which were calculated as:

% Control$_{min}$=100*(x−mLC)/(mHC−mLC)

where mLC and mHC were the means of the low control wells and high control wells on the plate, after manual exclusion of outliers. A plot of Control$_{min}$ versus test compound concentration was fitted to a 4-parameter logistic curve using a non-linear least squares regression method. From the plot, an IC$_{50}$ (concentration at which 50% inhibition is achieved) was calculated. pIC$_{50}$ values were calculated as −log(IC$_{50}$), when IC$_{50}$ is expressed in molar units.

Representative compounds of the present invention were tested according to the procedure as described in Biological Example 2 above, with results as listed in Table BIO-2, below. Where a compound was tested more than once, the pIC$_{50}$ value listed below represents the mean of the measurements.

TABLE BIO-2

FASN Keto-reductase Domain pIC$_{50}$

| Compound No. | pIC$_{50}$ |
|---|---|
| 1 | 6.86 |
| 2 | 6.15 |
| 3 | 6.33 |
| 4 | 6.22 |
| 5 | 6.27 |
| 6 | 6.38 |
| 7 | 6.89 |
| 8 | 6.41 |
| 9 | 6.22 |
| 10 | 5.95 |
| 11 | 5.41 |
| 12 | NT$^a$ |
| 13 | 5.94 |
| 14 | NT$^a$ |
| 15 | 6.75 |
| 16 | 6.20 |
| 17 | 5.57 |
| 18 | NT$^a$ |
| 19 | NT$^a$ |
| 20 | NT$^a$ |
| 21 | NT$^a$ |
| 22 | 6.57 |
| 23 | 7.25 |
| 24 | 6.45 |
| 25 | 6.17 |
| 26 | 6.08 |
| 27 | 6.41 |
| 28 | 7.14 |
| 29 | 6.62 |
| 30 | 7.17 |
| 31 | 6.33 |
| 32 | 5.86 |
| 33 | 6.38 |
| 34 | 5.95 |
| 35 | NT$^a$ |
| 36 | NT$^a$ |
| 37 | NT$^a$ |
| 38 | NT$^a$ |
| 39 | 6.81 |
| 40 | 6.46 |
| 41 | 7.13 |
| 42 | 6.32 |
| 43 | 5.93 |
| 44 | 6.65 |
| 45 | 6.95 |
| 46 | 6.90 |

TABLE BIO-2-continued

FASN Keto-reductase Domain $pIC_{50}$

| Compound No. | $pIC_{50}$ |
|---|---|
| 47 | 6.52 |
| 48 | 6.17 |
| 49 | 7.20 |
| 50 | 6.45 |
| 51 | 6.36 |
| 52 | 5.77 |
| 53 | 6.49 |
| 54 | 6.55 |
| 55 | 6.60 |
| 56 | 6.33 |
| 57 | 5.56 |
| 58 | NT[a] |
| 59 | NT[a] |
| 60 | NT[a] |
| 61 | 5.74 |
| 62 | 6.26 |
| 63 | 6.73 |
| 64 | NT[a] |
| 65 | 6.14 |
| 66 | 7.28 |
| 67 | 7.27 |
| 68 | 7.32 |
| 69 | 6.67 |
| 70 | 6.97 |
| 71 | NT[a] |
| 72 | 7.23 |
| 73 | 7.17 |
| 74 | 7.38 |
| 75 | NT[a] |
| 76 | NT[a] |
| 77 | 6.44 |
| 78 | 6.19 |
| 79 | 6.92 |
| 80 | 6.96 |
| 81 | 6.10 |
| 82 | 7.30 |
| 83 | 6.76 |
| 84 | 7.27 |
| 85 | 6.80 |
| 86 | 7.60 |
| 87 | 7.06 |
| 88 | NT[a] |
| 89 | NT[a] |
| 90 | NT[a] |
| 91 | NT[a] |
| 92 | NT[a] |
| 93 | NT[a] |
| 94 | NT[a] |
| 95 | NT[a] |
| 96 | NT[a] |
| 97 | NT[a] |
| 98 | NT[a] |
| 99 | NT[a] |

[a]The notation "NT" indicates that the listed compound was not tested.

Biological Example 3

A2780 Ovarian Cell Proliferation Assay in Lipid Reduced Medium, with and without Palmitate The biological assays described below correspond to comparative assays for ovarian cell proliferation. The assay procedure described below which includes addition of added palmitate correspond to the control relative to the assay procedure which does not include addition of the palmitate. Compounds active in the absence of palmitate would not be expected to be active in the control.

With Palmitate:

2500 cells were seeded in a 96-well clear well plate in 200 μL RPM11640 with 10% Fetal Calf Serum (Hyclone), and incubated at 37° C., 5% $CO_2$. Blanks were wells without cells. The next day the culture medium was aspirated and replaced by 160 μL culture medium with 10% Lipid-Reduced Serum (LRS, Hyclone). 20 μL test compound (at concentrations of 30 μM, 10 μM, 3 μM, 1 μM, 0.30 μM, 0.10 μM, 0.03 μM and 0.01 μM)/DMSO dilution followed by 20 μL palmitate-BSA solution were added to a final concentrations of 0.2% DMSO, 25 μM palmitate (Sigma, P0500, 10 mM stock solution in ethanol) 0.2% fatty-acid-free BSA, 0.25% ethanol. After 96 h incubation, an MTT assay was performed. The absorbance was measured at 544 nm on a SPECTRAMAX.

A best fit curve was fitted by a minimum sum of squares method, plotting $Control_{min}$ versus test compound concentration. From the plot, an $IC_{50}$ (concentration at which 50% inhibition is achieved) was calculated. $pIC_{50}$ values, presented in the Table below, were calculated as $-\log(IC_{50})$.

Without Palmitate:

2500 cells were seeded in a 96-well clear well plate in 200 μL RPM11640 with 10% Fetal Calf Serum (Hyclone), and incubated at 37° C., 5% $CO_2$. Blanks were wells without cells. The next day the culture medium was aspirated and replaced by 160 μL culture medium with 10% Lipid-Reduced Serum (LRS, Hyclone). 20 μL test compound (at concentrations of 30 μM, 10 μM, 3 μM, 1 μM, 0.30 μM, 0.10 μM, 0.03 μM and 0.01 μM)/DMSO dilution followed by 20 μL ethanol-BSA solution were added to a final concentrations of 0.2% DMSO, 0.2% fatty-acid-free BSA, 0.25% ethanol. After 96 h incubation an MTT assay was performed. The absorbance was measured at 544 nm on a SPECTRAMAX.

Raw data generated by the instrument were normalized to % Controlmin values, which were calculated as:

% $Control_{min}=100*(x-\text{mLC})/(\text{mHC}-\text{mLC})$ where mLC and mHC were the means of the low control wells and high control wells on the plate, after manual exclusion of outliers. A plot of $Control_{min}$ versus test compound concentration was fitted to a 4-parameter logistic curve using a non-linear least squares regression method. From the plot, an $IC_{50}$ (concentration at which 50% inhibition is achieved) was calculated. $pIC_{50}$ values were calculated as $-\log(IC_{50})$, when $IC_{50}$ is expressed in molar units.

Representative compounds of the present invention were tested according to the procedure as described in Biological Example 3 above, with results as listed in Table BIO-3, below. Where a compound was tested more than once, the $pIC_{50}$ value listed below represents the mean of the measurements. Wherein the results listed below, the $pIC_{50}$ value is preceded with a "~", the "~" the "~" indicates that the standard error of the $pIC_{50}$ value, as estimated by the non-linear regression algorithm, is larger than 0.5. This corresponds to a factor of uncertainly on the $pIC_{50}$ that is larger than square root of 10 (>3.162).

TABLE BIO-3 pIC50 Ovarian Cell, Reduced Medium With and Without Palmitate

| Compound No. | $pIC_{50}$ With Palmitate | $pIC_{50}$ Without Palmitate |
|---|---|---|
| 1 | <5 | 7.13 |
| 2 | <5 | 6.28 |
| 3 | <5 | 5.83 |
| 4 | <5 | 5.56 |
| 5 | <5 | 5.70 |
| 6 | <5 | 6.44 |
| 7 | <5 | 6.88 |

TABLE BIO-3-continued pIC50 Ovarian Cell, Reduced Medium With and Without Palmitate

| Compound No. | pIC$_{50}$ With Palmitate | pIC$_{50}$ Without Palmitate |
|---|---|---|
| 8 | <5 | 5.94 |
| 9 | <5 | ~5.72 |
| 10 | <5 | ~6.13 |
| 11 | <5 | 5.43 |
| 12 | NT$^a$ | NT$^a$ |
| 13 | <5 | 5.47 |
| 14 | NT$^a$ | NT$^a$ |
| 15 | <5 | 6.75 |
| 16 | <5 | 6.73 |
| 17 | <5 | 5.60 |
| 18 | NT$^a$ | NT$^a$ |
| 19 | NT$^a$ | NT$^a$ |
| 20 | NT$^a$ | NT$^a$ |
| 21 | NT$^a$ | NT$^a$ |
| 22 | <5 | ~6.57 |
| 23 | <5 | 7.12 |
| 24 | <5 | ~6.44 |
| 25 | <5 | 5.93 |
| 26 | <5 | 5.71 |
| 27 | <5 | ~6.5 |
| 28 | <5 | 7.23 |
| 29 | <5 | 5.91 |
| 30 | <5 | 5.91 |
| 31 | <5 | ~6 |
| 32 | <5 | 6.01 |
| 33 | <5 | 6.61 |
| 34 | <5 | 6.00 |
| 35 | NT$^a$ | NT$^a$ |
| 36 | NT$^a$ | NT$^a$ |
| 37 | NT$^a$ | NT$^a$ |
| 38 | NT$^a$ | NT$^a$ |
| 39 | <5 | ~7.04 |
| 40 | 5.25 | 6.33 |
| 41 | <5 | ~6.46 |
| 42 | <5 | ~6.72 |
| 43 | NT$^a$ | NT$^a$ |
| 44 | <5 | 7.33 |
| 45 | <5 | 7.58 |
| 46 | 5.02 | 7.28 |
| 47 | ~5 | ~6.03 |
| 48 | <5 | 6.27 |
| 49 | <5 | 7.85 |
| 50 | <5 | 6.22 |
| 51 | <5 | 6.54 |
| 52 | <5 | 6.15 |
| 53 | NT$^a$ | NT$^a$ |
| 54 | NT$^a$ | NT$^a$ |
| 55 | NT$^a$ | NT$^a$ |
| 56 | NT$^a$ | NT$^a$ |
| 57 | NT$^a$ | NT$^a$ |
| 58 | NT$^a$ | NT$^a$ |
| 59 | NT$^a$ | NT$^a$ |
| 60 | NT$^a$ | NT$^a$ |
| 61 | NT$^a$ | NT$^a$ |
| 62 | NT$^a$ | NT$^a$ |
| 63 | NT$^a$ | NT$^a$ |
| 64 | <5 | 5.35 |
| 65 | <5 | 6.58 |
| 66 | <5 | ~6.37 |
| 67 | <5 | ~6.71 |
| 68 | <5 | 7.76 |
| 69 | <5 | 7.19 |
| 70 | <5 | 7.61 |
| 71 | <5 | ~5.03 |
| 72 | 5.11 | ~7.59 |
| 73 | <5 | 7.87 |
| 74 | <5 | 8.41 |
| 75 | 5.48 | 7.96 |
| 76 | <5 | 7.63 |
| 77 | <5 | 6.50 |
| 78 | <5 | 6.27 |
| 79 | <5 | 6.91 |
| 80 | <5 | 7.34 |
| 81 | <5 | 6.64 |
| 82 | 5.36 | 7.84 |
| 83 | <5 | 7.59 |
| 84 | 5.36 | 8.48 |
| 85 | <5 | 8.41 |
| 86 | ~5.11 | 8.40 |
| 87 | ~5 | 7.93 |
| 88 | <5 | ~7.83 |
| 89 | <5 | 8.17 |
| 90 | <5 | ~8.53 |
| 91 | <5 | 6.89 |
| 92 | <5 | ~8.26 |
| 93 | <5 | 7.51 |
| 94 | <5 | 7.00 |
| 95 | <5 | ~8.27 |
| 96 | <5 | ~7.65 |
| 97 | NT$^a$ | NT$^a$ |
| 98 | <5 | <5 |
| 99 | <5 | <5 |

$^a$The notation "NT" indicates that the listed compound was not tested.

Biological Example 4

Example 4a: In Vitro LNCaP Vancouver Prostate Cell Proliferation Assay in Lipid Reduced Medium LNCaP_Vancouver prostate cells were obtained from the Vancouver Prostate Cancer Centre. Cells were maintained in RPMI-1640, 10% Fetal Calf Serum (FCS, Hyclone), 2 mM glutamine and 50 µg/ml Gentamicin.

For the proliferation experiment 1500 LNCaP_Vancouver cells per well were seeded in a 384-well black with clear bottom plate (costar 3712BC) in 40 µl RPM1-1640, 10% Lipid reduced serum (LRS, Hyclone), 50 µg/ml Gentamicin and 2 mM Glutamine and incubated at 37° C., 5% $CO_2$. The next day 10 µl of test compound/DMSO diluted in medium was added (3E-5M, 1E-5M, 3E-6M, 1E-6M, 3E-7M, 1E-7M, 3E-8M, 1E-8M final concentration). Compounds were tested in duplicate. After 96 h incubation at 37° C., 5% $CO_2$ 25 µl ATP-glow mix was added. The plate was incubated for 30 min at 37° C. and luminescence was measured with the Envision.

Example 4b: In Vitro PC-3M-Luc-C6 Prostate Cell Proliferation Assay in Lipid Reduced Medium PC-3M-Luc-C6 prostate cells were obtained from Xenogen Corporation. Cells were maintained in MEM supplemented with 10% Fetal Calf Serum (FCS, Hyclone), 2 mM glutamine, 1 mM sodium pyruvate, 1% BME vitamins (available from for example, Sigma Aldrich), 0.1 mM non Essential Amino Acid and 50 µg/ml Gentamicin. The cells were passaged twice a week.

1000 PC-3M-Luc-C6 prostate cells (Xenogen) were seeded in a 384-well black with clear bottom plate (costar 3712BC) in 40 µl MEM, 10% LRS (Hyclone), 50 µg/ml Gentamicin, 2 mM Glutamine, 1 mM Sodium pyruvaat, 1% BME vitamins and 0.1 mM non Essential Amino Acid and incubated at 37° C., 5% $CO_2$. The next day 10 µl test compound/DMSO diluted in medium was added (3E-5M, 1E-5M, 3E-6M, 1E-6M, 3E-7M, 1E-7M, 3E-8M, 1E-8M final concentration). Compounds were tested in duplicate. After 96 h incubation at 37° C., 5% $CO_2$ 25 µl ATP-glow mix was added. The plate was incubated for 30 min at 37° C. and luminescence was measured with the Envision.

Analysis: Determination of pIC50 Values $pIC_{50}$ values were calculated as follows. Raw data generated by the instruments were normalized to % $Control_{min}$ values, which were calculated as:

% $Control_{min}=100*(x\text{-mLC})/(\text{mHC-mLC})$, where mLC and mHC are the means of the low control wells and high control wells on the plate, after manual exclusion of outliers. The relation between the % $Control_{min}$ values and concentration was fitted to a 4-parameter logistic curve using a non-linear least squares regression method to determine the $pIC_{50}$ value. Outlying data points were excluded manually to get a correct fit. The $pIC_{50}$ corresponds to $-\log 10(IC_{50})$, if the $IC_{50}$ is expressed in molar units (http://www.ncbi.nlm.nih.qovibooks/NBK91994). The $IC_{50}$ parameter was always determined by non-linear regression, but one or more of the other parameters may have been held fixed on a relevant input value, such as 0 for the bottom values.

For dose response curves with FASN inhibitors in LNCaP_Vancouver or PC-3M-Luc_C6 cells the curves bottom out around 30 to 40% of the control value. A standard fit PL2, forcing the lower bound to this level was used. For those test compounds which did not exhibit FASN related toxicities (but other non-target related cellular toxicity), the % control value may go to 0, and curve fit was calculated using 0% as lower bound.

Representative compounds of the present invention were tested according to the procedure as described in Biological Example 4a and 4b above, with results as listed in Table BIO-4, below. Where a compound was tested more than once, the $pIC_{50}$ value listed below represents the mean of the measurements. Wherein the results listed below, the $pIC_{50}$ value is preceded with a "~", the "~" the "~" indicates that the standard error of the $pIC_{50}$ value, as estimated by the non-linear regression algorithm, is larger than 0.5. This corresponds to a factor of uncertainly on the $pIC_{50}$ that is larger than square root of 10 (>3.162).

TABLE BIO-4

| | $pIC_{50}$ Prostate Cell Proliferation, Reduced Medium | |
|---|---|---|
| Compound No. | $pIC_{50}$ LNCaP_Vancouver prostate cell | $pIC_{50}$ PC-3M-Luc-C6 prostate cell |
| 1 | NT[a] | NT[a] |
| 2 | NT[a] | NT[a] |
| 3 | NT[a] | NT[a] |
| 4 | NT[a] | NT[a] |
| 5 | 5.36 | ~5.73 |
| 6 | 5.74 | 6.30 |
| 7 | 6.63 | 7.13 |
| 8 | 5.59 | 5.89 |
| 9 | 5.69 | 5.79 |
| 10 | 5.44 | 6.03 |
| 11 | ~5 | ~5.7 |
| 12 | NT[a] | NT[a] |
| 13 | 5.20 | 5.68 |
| 14 | NT[a] | NT[a] |
| 15 | 6.12 | 6.80 |
| 16 | 6.48 | 6.76 |
| 17 | 5.05 | 5.74 |
| 18 | NT[a] | NT[a] |
| 19 | NT[a] | NT[a] |
| 20 | NT[a] | NT[a] |
| 21 | NT[a] | NT[a] |
| 22 | 6.09 | 6.65 |
| 23 | 6.66 | 7.27 |
| 24 | 5.84 | 6.35 |
| 25 | 5.54 | 6.05 |
| 26 | 5.47 | 6.00 |
| 27 | 5.86 | 6.49 |
| 28 | 5.80 | 7.20 |
| 29 | ~5.55 | 5.89 |
| 30 | 5.47 | 6.31 |
| 31 | 6.04 | ~6.21 |
| 32 | 5.33 | 5.83 |
| 33 | 5.69 | NT[a] |
| 34 | 5.58 | 6.08 |
| 35 | NT[a] | NT[a] |
| 36 | NT[a] | NT[a] |
| 37 | NT[a] | NT[a] |
| 38 | NT[a] | NT[a] |
| 39 | 6.57 | 7.02 |
| 40 | 5.69 | NT[a] |
| 41 | 5.94 | 6.38 |
| 42 | 6.00 | 6.38 |
| 43 | 5.63 | 6.06 |
| 44 | 6.41 | 7.32 |
| 45 | 6.93 | 7.17 |
| 46 | 6.39 | NT[a] |
| 47 | 5.45 | NT[a] |
| 48 | 5.40 | NT[a] |
| 49 | 6.70 | ~7.62 |
| 50 | 5.99 | 6.41 |
| 51 | 6.10 | 6.49 |
| 52 | 5.89 | 6.11 |
| 53 | 6.14 | 6.88 |
| 54 | 6.39 | 6.89 |
| 55 | 6.92 | 7.36 |
| 56 | 6.47 | 7.20 |
| 57 | 5.75 | 6.19 |
| 58 | NT[a] | NT[a] |
| 59 | NT[a] | NT[a] |
| 60 | NT[a] | NT[a] |
| 61 | 5.30 | 5.75 |
| 62 | 6.11 | 5.92 |
| 63 | 6.28 | NT[a] |
| 64 | NT[a] | NT[a] |
| 65 | 5.90 | ~6.04 |
| 66 | 6.16 | 6.23 |
| 67 | 6.39 | 6.84 |
| 68 | 6.69 | NT[a] |
| 69 | 6.87 | 7.04 |
| 70 | 6.87 | 7.96 |
| 71 | NT[a] | NT[a] |
| 72 | 6.53 | 7.57 |
| 73 | 6.40 | 7.73 |
| 74 | 7.94 | ~8.08 |
| 75 | NT[a] | NT[a] |
| 76 | NT[a] | NT[a] |
| 77 | 5.93 | 6.95 |
| 78 | 5.51 | 6.35 |
| 79 | NT[a] | 7.15 |
| 80 | NT[a] | 7.77 |
| 81 | NT[a] | 6.18 |
| 82 | NT[a] | 7.19 |
| 83 | NT[a] | 7.37 |
| 84 | NT[a] | 8.11 |
| 85 | NT[a] | ~7.97 |
| 86 | NT[a] | 8.21 |
| 87 | 6.75 | ~7.15 |
| 88 | NT[a] | NT[a] |
| 89 | NT[a] | NT[a] |
| 90 | NT[a] | NT[a] |
| 91 | NT[a] | NT[a] |
| 92 | NT[a] | NT[a] |
| 93 | NT[a] | NT[a] |
| 94 | NT[a] | NT[a] |
| 95 | NT[a] | NT[a] |
| 96 | NT[a] | NT[a] |
| 97 | NT[a] | NT[a] |
| 98 | NT[a] | NT[a] |
| 99 | NT[a] | NT[a] |

[a] The notation "NT" indicates that the listed compound was not tested.

Biological Example 5—Prophetic Example

$^{14}$C-Acetate Incorporation in HEPG2 Liver Cells

HepG2 liver cells are obtained from the American Type Culture Collection. Cells are seeded in a 24-well plate at $7.10^5$ cells/well in 400 µL MEM with 10% FCS (Hyclone). 100 µL of test compound dilution (25 µM to 5 µM final) is added and plates are incubated for 4 hours at 37° C. in 5% $CO_2$. 50 µL of $^{14}$C-acetic acid (Acetic acid, sodium salt (1,2-14C): Amersham CFA13; 50-62 mCi/mMol, 200 µCi/ml (7.4 mBq/ml)) diluted 1/50 in medium is added and plates are incubated for another 2 h at 37° C. in 5% $CO_2$. Medium is aspirated, and lipids are extracted from the cells by 3 rounds of chloroform:methanol:$MgSO_4$ mixture and centrifugation steps (2 min at 10000 rpm). Each time the upper layer is removed. Finally the remaining organic layer is evaporated under nitrogen gas, the pellet are dissolved in 500 µL heptanes and in 3 ml of scintillation fluid added to scintillation tubes. Incorporated $^{14}$C-labelled is counted in a Pachard, Tri-Carb Liquid scintillation counter. (2 minutes)

Biological Example 6—Prophetic Example

Analysis of Intact Phospholipid Species by Electrospray Ionization Tandem Mass Spectrometry PC-3 prostate and A2780 ovarian cells are obtained from the American Type Culture Collection. Cells are cultured in HamF12 or RPMI 1640 respectively, supplemented with 10% FCS (Invitrogen). Palmitic acid (Sigma) is complexed to fatty acid-free bovine serum albumin (Invitrogen). Cells are cultured for 72 hours in the presence or absence of test compound (10 µM to 0.1 µM). Xenografts are collected after 21 days treatment with or without compound (100-10 mg/kg).

Tissue or cells are homogenized in 1 N HCl/$CH_3OH$ (1:8, v/v). $CHCl_3$, 200 µg/mL of the antioxidant 2,6-di-tert-butyl-4-methylphenol (Sigma; ref. 29), and lipid standards are added. The organic fractions are evaporated and reconstituted in $CH_3OH$/$CHCl_3$/$NH_4OH$ (90:10:1.25, v/v/v). Phospholipids are analyzed by electrospray ionization tandem mass spectrometry (ESI-MS/MS) on a hybrid quadrupole linear ion trap mass spectrometer (4000 QTRAP system, Applied Biosystems) equipped with a robotic nanoflow/ion source (Advion Biosciences). The collision energy is varied as follows: precursor ion m/z 184, 50 eV; neutral loss of 141, 35 eV; neutral loss of 87, −40 eV; precursor ion m/z 241, −55 eV. The system is operated in the multiple reaction monitoring (MRM) mode for quantification of individual species. Typically, a 3-minute period of signal averaging is used for each spectrum. Data are corrected for $^{13}$C isotope effects if the contribution is >10%. Corrected data were presented as heat maps using the HeatMap Builder software (Clifton Watt, Stanford University).

Biological Example 7–Prophetic Example

Xenograft Hematological Assay

Animals:

Male NMRI-nude mice (obtained from Janvier) are used for the study. Mice with an initial weight of approximately 20 to 25 g are obtained. The animals are habituated for one week prior to any experimental protocols/procedures being performed.

All animals are maintained under SPF (specific pathogen-free) "full barrier" conditions with free access to food and water. Mice are group housed under a 12-h light:dark cycle (lights on at 06:00 h) at a temperature of 19 to 22° C. and 35 to 40% humidity in Techniplast type-3 IVC cages. Mice are fed a standard Laboratory chow. All experiments are carried out in accordance with the European Communities Council Directives (86/609/EEC) and are approved by the local ethical committee.

Prostate Tumor Cells:

The human PC3 prostate tumor cells are cultured at 37° C. in a humidified atmosphere (5% $CO_2$, 95% air), in F12-Ham medium supplemented with 2 mM Sodium Pyruvate, 50 µg/ml Gentamycin, 1.5 g/l Sodium Bicarbonate, 0.1 mM Non Essential Amino Acids and 10% fetal bovine calf serum. Cells are maintained as cell monolayer cultures, passaged twice weekly at $3\times10^6$ cells per T175 flask, according to the following procedure. Cells are washed with PBS (w/o $Mg^{2+}$, $Ca^{2+}$), before addition of trypsin-EDTA to the culture flasks. After detachment of cells, the trypsin-EDTA is inactivated by addition of complete medium. The cell suspension is then transferred to 50 ml Falcon tube and centrifuged for 3 min at 1200 rpm. Medium is aspirated, with the cells being re-suspended in an appropriate volume of complete medium. The cells are counted in a haemocytometer and their viability is assessed by 0.25% trypan blue exclusion. An appropriate volume of cell suspension is then added to either a new T175 culture flask(s) or roller bottle containing fresh medium. For large scale-up growth of PC3 prostate tumor cells, an appropriate number of roller bottles are seeded with $1.2\times10^7$ cells 1 week prior to inoculation of the mice. The medium is changed twice during this period, with the last change being the day prior to cell injection. Cells are collected as described above, with the exception that after centrifugation, the cells are re-suspended in cold (4° C.) serum free medium at $5\times10^7$ cells/ml.

Experimental Design:

Human PC3 prostate tumor cells are injected directly into the inguinal region of the male NMRI Nude mice ($1\times10^7$ cells/200 µl/animal) on day 0. Approximately 35 days after inoculation, when tumor volumes reach an approximate average of 200 $mm^3$, mice are randomized into test groups according to tumor volume, and treated for 21 days with either control (no test compound) or test compound at one of three dosage levels: 10 mg/kg, 30 mg/kg or 100 mg/kg.

Data Analysis:

For each individual animal, body weight and tumor size [using the commonly accepted formula: Tumor Volume $(mm^3)=(a\times b^2/2)$; where 'a' represents the length, and 'b' the width of the tumor as determined by caliper measurements], are monitored twice weekly throughout the study. A sustained body weight loss greater than 15% of the initial body weight is considered as clinical toxicity, with the animal removed from the study and sacrificed. Clinical signs of toxicity include, but are not limited to, persistent anorexia or dehydration, posture, moribund, lethargy, hypothermia and/or labored respiration (according to the UKCCCR guidelines for welfare of animals in preclinical in vivo tumor models)

A time-course of tumor growth is expressed as median values, or normalized to initial tumor volume on the day treatment started and expressed as mean±SEM (8 to 10 animals per group). For pre-established tumors, relative tumor volumes is calculated for each mouse (treated tumor volume/tumor volume on day 0) and expressed as mean±SEM for each treatment group. Twenty-four hours after the last treatment, animals are sacrificed, tumors excised and weighed. The anti-tumor effect of test compound versus control is determined and represented by a bar chart of median values±25/75 and 10/90 percentiles. Statistical significance is indicated by one-sided p-values from Wilcoxon-Mann-Whitney analysis (Wilcoxon rank sum test), with p<0.05 considered statistically significant. Treatment/control (T/C) ratios are calculated based on final relative tumor volumes, using the NCI criteria—"The effective criteria for T/C ratios is 42%".

Biological Example 8

In Vivo MaCoA Determination in NCI-H460 Xenografts

Test System

All experiments will be carried out in accordance with the European Communities Council Directives (86/609/EEC) and were approved by the local ethical committee.

Human NCI-H460 tumor cells (ATCC) were cultured at 37° C. in a humidified atmosphere (5% CO2, 95% air), in RPMI 1640 Medium supplemented with 10 mM HEPES, Glucose 4.5 g/I, 50 µg/ml Gentamycin, 1 mM Sodium Pyruvate, L-glutamine 2 mM and 10% fetal bovine calf serum (FBS). Cells were maintained as adherent epithelial cells being passaged once weekly at 10×10E6 cells per T300 using the following procedure. Briefly cells were washed with PBS (w/o Mg2+, Ca2+), before addition of trypsin-EDTA to the culture flasks. After detachment of cells the trypsin-EDTA was inactivated by addition of complete medium. Cell suspension was transferred to 50 ml Falcon tube and centrifuged for 3 min at 1200 rpm. Medium was aspirated, with the cells re-suspended in an appropriate volume of complete medium. The cells were counted in a cell counter (haemocytometer) and their viability assessed by 0.25% trypan blue exclusion. Last change of medium was performed 24 hours before cell collection. Cells were collected as described above except re-suspending after centrifugation in cold (4° C.) serum free medium at $5 \times 10^7$ cells/ml.

Male NMRI-nude mice (obtained from Janvier) were injected subcutaneously with $1 \times 10^7$ cells total in a 200 µl volume. Mice were dosed when tumors reach an average size of 300 mm$^3$, with 3 and 30 mg/kg compound, orally, BID1.5× (n=3 per condition). 4 hours after the last dose tumors were excised and divided in two pieces of about 100 to 150 mg. One portion was used for MaCoA determination, the other portion was used for compound concentration. MaCoA induction was determined as fold induction versus the solvent treatment.

Analytical Procedure for the Quantification of Malonyl Coenzyme A in Tumor Tissue by LC/MS/MS (Calibration Range 5-5000 ng/mL in Tissue Homogenate)

The raw tissue samples were kept on dry ice at all times. Tumor tissue was weighed and homogenized with 2.0 mL of 5% trifluoroacetic acid (TFA) in water with an automated homogenizer (Bertin Precellys 24 tissue homogenizer). After centrifugation, a portion of the supernatant was combined with the internal standard (Malonyl CoA $^{13}C_3$ Lithium Salt).

The supernatant was subjected to solid-phase extraction (SPE). Samples were eluted with 0.1% TFA in methanol into a clean round-bottom plastic tubes. The eluent was evaporated under nitrogen, and the residue reconstituted and transferred in an HPLC vial. The standards were neat standards and the concentration applied was the final concentration for the standards in the HPLC vial.

The samples were analyzed by LC/MS/MS using a Zorbax Eclipse XDB-C8 column coupled with a triple quadrupole mass spectrometer (MDS Sciex API 5000 with TurboIonSpray™, Negative Polarity mode). Instrument was run in MRM mode choosing appropriate transitions for analyte and internal standard.

Chromatogram peaks were integrated using the Analyst version 1.4.2 software package. A weighted ($1/x^2$ where x equals concentration) linear regression analysis was used. The peak area ratio of malonyl CoA to the internal standard versus the nominal concentration was plotted. The slope, intercept and the correlation coefficient were calculated. The unknown concentration (x) was then calculated with the following formula:

$$x=(y-b)/m$$

where y is the peak area ratio of unknown malonyl CoA to internal standard, b is the y intercept and m is the slope.

Compound #72 was dissolved in a 9:1 mixture of PEG400:ethanol at a concentration of 3 mg/mL, and tested according to the procedure as described above, with results as listed in Table BIO-8, below.

TABLE BIO-8

| Human NCI-H460 tumor cells PD Assay | |
| --- | --- |
| Dosage | MaCoA Fold Induction |
| 3 mg/kg | 3.3 |
| 30 mg/kg | 67.8 |

Formulation Example 1—Prophetic Example

Solid, Oral Dosage Form

As a specific embodiment of an oral composition, 100 mg of the Compound #1, prepared as in Example 1, above is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A method of treating a disorder mediated by inhibition of fatty acid synthase (FASN) enzyme comprising administering to a subject in need thereof a therapeutically effective amount of a compound of formula (I)

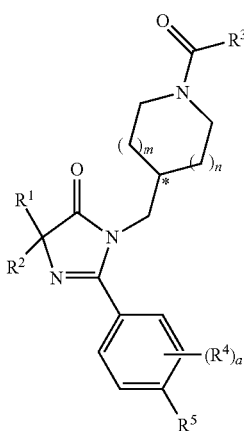

(I)

wherein
R$^1$ is C$_{1-4}$alkyl and fluorinated C$_{1-2}$alkyl;
R$^2$ is selected from the group consisting of C$_{1-4}$alkyl, fluorinated C$_{1-2}$alkyl, —(C$_{1-4}$alkyl)-O—(C$_{1-4}$alkyl), C$_{3-6}$cycloalkyl, phenyl and 5 to 6 membered heteroaryl; wherein the phenyl or 5 to 6 membered heteroaryl is optionally substituted with one to two substituents independently selected from the group consisting of halogen, C$_{1-4}$alkyl, fluorinated C$_{1-2}$alkyl, C$_{1-4}$alkoxy, fluorinated C$_{1-2}$alkoxy and cyano;
m is an integer from 0 to 1; and n is an integer from 0 to 1; provided that each of m and n are not 1;

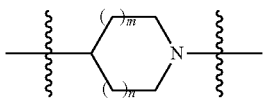

is selected from the group consisting of azetidin-3-yl, pyrrolidin-3-yl and piperidin-4-yl;
R$^3$ is selected from the group consisting of C$_{1-4}$alkyl, fluorinated C$_{1-4}$alkyl, C$_{2-4}$alkenyl, C$_{3-6}$cycloalkyl, —(C$_{1-4}$alkyl)-(C$_{3-6}$cycloalkyl), 4 to 6 membered, saturated heterocyclyl, —(C$_{1-4}$alkyl)-(4 to 6 membered, saturated heterocyclyl), 5 to 6 membered heteroaryl and —(C$_{1-4}$alkyl)-(5 to 6 membered heteroaryl); wherein the C$_{3-6}$cycloalkyl, 4 to 6 membered, saturated heterocyclyl or 5 to 6 membered heteroaryl, whether alone or as part of a substituent group, is optionally substituted with one to two substituents independently selected from the group consisting of halogen, hydroxy, cyano, C$_{1-4}$alkyl, fluorinated C$_{1-4}$alkyl, C$_{1-4}$alkoxy, fluorinated C$_{1-4}$alkoxy and NR$^A$R$^B$; wherein R$^A$ and R$^B$ are each independently selected from the group consisting of hydrogen and C$_{1-4}$alkyl;
a is an integer from 0 to 2;
each R$^4$ is independently selected from the group consisting of hydroxy, halogen, C$_{1-4}$alkyl, fluorinated C$_{1-4}$alkyl, C$_{1-4}$alkoxy, fluorinated C$_{1-4}$alkoxy, cyano, and NR$^C$R$^D$; wherein R$^C$ and R$^D$ are each independently selected from the group consisting of hydrogen and C$_{1-4}$alkyl;
R$^5$ is selected from the group consisting of aryl and heteroaryl; wherein the aryl or heteroaryl is optionally substituted with one to two substituents independently selected from the group consisting of hydroxy, halogen, cyano, nitro, C$_{1-4}$alkyl, fluorinated C$_{1-4}$alkyl, hydroxy substituted C$_{1-4}$alkyl, C$_{1-4}$alkoxy, fluorinated C$_{1-4}$alkoxy, NR$^E$R$^F$, —(C$_{1-4}$alkyl)-NR$^E$R$^F$, —C(O)—(C$_{1-4}$alkyl), —C(O)—NR$^E$R$^F$, —C(O)OH, —C(O)O—(C$_{1-4}$alkyl), —NR$^E$—C(O)—(C$_{1-4}$alkyl) and —NR$^E$—SO$_2$—(C$_{1-4}$alkyl); wherein R$^E$ and R$^F$ are each independently selected from the group consisting of hydrogen and C$_{1-4}$alkyl;
alternatively, R$^5$ is

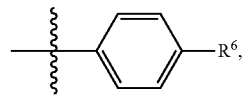

wherein R$^6$ is selected from the group consisting of phenyl and 5 to 6 membered heteroaryl; wherein the phenyl or 5 to 6 membered heteroaryl is optionally substituted with one to two substituents independently selected from the group consisting of hydroxy, halogen, cyano, nitro, C$_{1-4}$alkyl, fluorinated C$_{1-4}$alkyl, hydroxy substituted C$_{1-4}$alkyl, C$_{1-4}$alkoxy, fluorinated C$_{1-4}$alkoxy, NR$^G$R$^H$, —C(O)—NR$^G$R$^H$, —C(O)OH, —C(O)O—(C$_{1-4}$alkyl) and —(C$_{1-4}$alkyl)-NR$^G$R$^H$; wherein R$^G$ and R$^H$ are each independently selected from the group consisting of hydrogen and C$_{1-4}$alkyl;
or a stereoisomer, tautomer or pharmaceutically acceptable salt thereof;
wherein the disorder mediated by inhibition of fatty acid synthase (FASN) enzyme is selected from the group consisting of
(a) cancer selected from the group consisting of breast, prostate, head, neck, skin, lung, ovary, endometrium, thyroid, colon, rectum, esophagus, stomach, kidney, liver, bladder, pancreas, brain, spinal cord, blood, and bone; wherein the treatment of cancer consists essentially of inducing apoptosis in or inhibiting proliferation of cancer cells;
(b) obesity; and
(c) Type II diabetes mellitus.
2. The method of claim 1, wherein the disorder mediated by inhibition of fatty acid synthase (FASN) enzyme is cancer of the breast, prostate, head, neck, skin, lung, ovary, endometrium, thyroid, colon, rectum, esophagus, stomach, kidney, liver, bladder, pancreas, brain, spinal cord, blood or bone.
3. The method of claim 1, wherein the disorder mediated by inhibition of fatty acid synthase (FASN) enzyme is selected from the group consisting of obesity and Type II diabetes mellitus.
4. A method of treating a disorder selected from the group consisting of
(a) cancer of the breast, prostate, head, neck, skin, lung, ovary, endometrium, thyroid, colon, rectum, esophagus, stomach, kidney, liver, bladder, pancreas, brain, spinal cord, blood or bone; wherein the treatment of cancer consists essentially of inducing apoptosis in or inhibiting proliferation of cancer cells;
(b) obesity;
(c) Type II diabetes mellitus;
comprising administering to a subject in need thereof a therapeutically effective amount of a pharmaceutical composition comprising a pharmaceutically acceptable carrier and a compound a compound of formula (I)

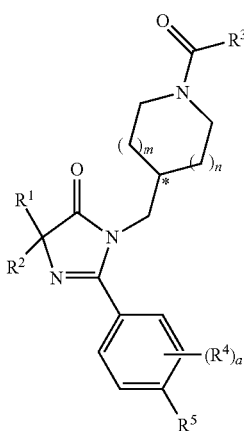

(I)

wherein
$R^1$ is $C_{1-4}$alkyl and fluorinated $C_{1-2}$alkyl;
$R^2$ is selected from the group consisting of $C_{1-4}$alkyl, fluorinated $C_{1-2}$alkyl, —($C_{1-2}$alkyl)-O—($C_{1-4}$alkyl), $C_{3-6}$cycloalkyl, phenyl and 5 to 6 membered heteroaryl; wherein the phenyl or 5 to 6 membered heteroaryl is optionally substituted with one to two substituents independently selected from the group consisting of halogen, $C_{1-4}$alkyl, fluorinated $C_{1-2}$alkyl, $C_{1-4}$alkoxy, fluorinated $C_{1-2}$alkoxy and cyano;
m is an integer from 0 to 1; and n is an integer from 0 to 1; provided that each of m and n are not 1;

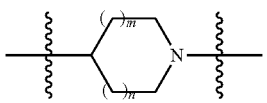

is selected from the group consisting of azetidin-3-yl, pyrrolidin-3-yl and piperidin-4-yl;
$R^3$ is selected from the group consisting of $C_{1-4}$alkyl, fluorinated $C_{1-4}$alkyl, $C_2$-4alkenyl, $C_{3-6}$cycloalkyl, —($C_{1-4}$alkyl)-($C_{3-6}$cycloalkyl), 4 to 6 membered, saturated heterocyclyl, —($C_{1-4}$alkyl)-(4 to 6 membered, saturated heterocyclyl), 5 to 6 membered heteroaryl and —($C_{1-4}$alkyl)-(5 to 6 membered heteroaryl); wherein the $C_{3-6}$cycloalkyl, 4 to 6 membered, saturated heterocyclyl or 5 to 6 membered heteroaryl, whether alone or as part of a substituent group, is optionally substituted with one to two substituents independently selected from the group consisting of halogen, hydroxy, cyano, $C_{1-4}$alkyl, fluorinated $C_{1-4}$alkyl, $C_{1-4}$alkoxy, fluorinated $C_{1-4}$alkoxy and $NR^AR^B$; wherein $R^A$ and $R^B$ are each independently selected from the group consisting of hydrogen and $C_{1-4}$alkyl;
a is an integer from 0 to 2;
each $R^4$ is independently selected from the group consisting of hydroxy, halogen, $C_{1-4}$alkyl, fluorinated $C_{1-4}$alkyl, $C_{1-4}$alkoxy, fluorinated $C_{1-4}$alkoxy, cyano, and $NR^CR^D$; wherein $R^C$ and $R^D$ are each independently selected from the group consisting of hydrogen and $C_{1-4}$alkyl;
$R^5$ is selected from the group consisting of aryl and heteroaryl; wherein the aryl or heteroaryl is optionally substituted with one to two substituents independently selected from the group consisting of hydroxy, halogen, cyano, nitro, $C_{1-4}$alkyl, fluorinated $C_{1-4}$alkyl, hydroxy substituted $C_{1-4}$alkyl, $C_{1-4}$alkoxy, fluorinated $C_{1-4}$alkoxy, $NR^ER^F$, —($C_{1-4}$alkyl)-$NR^ER^F$, —C(O)—($C_{1-4}$alkyl), —C(O)—$NR^ER^F$, —C(O)OH, —C(O)O—($C_{1-4}$alkyl), —$NR^E$—C(O)—($C_{1-4}$alkyl) and —$NR^E$—$SO_2$—($C_{1-4}$alkyl); wherein $R^E$ and $R^F$ are each independently selected from the group consisting of hydrogen and $C_{1-4}$alkyl;
alternatively, $R^5$ is

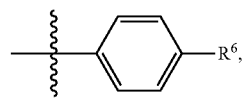

wherein $R^6$ is selected from the group consisting of phenyl and 5 to 6 membered heteroaryl; wherein the phenyl or 5 to 6 membered heteroaryl is optionally substituted with one to two substituents independently selected from the group consisting of hydroxy, halogen, cyano, nitro, $C_{1-4}$alkyl, fluorinated $C_{1-4}$alkyl, hydroxy substituted $C_{1-4}$alkyl, $C_{1-4}$alkoxy, fluorinated $C_{1-4}$alkoxy, $NR^GR^H$, —C(O)—$NR^GR^H$, —C(O)OH, —C(O)O—($C_{1-4}$alkyl) and —($C_{1-4}$alkyl)-$NR^GR^H$; wherein $R^G$ and $R^H$ are each independently selected from the group consisting of hydrogen and $C_{1-4}$alkyl;
or a stereoisomer, tautomer or pharmaceutically acceptable salt thereof.

* * * * *